(12) United States Patent
Mammen et al.

(10) Patent No.: US 8,247,564 B2
(45) Date of Patent: Aug. 21, 2012

(54) COMPOUNDS HAVING BETA2 ADRENERGIC RECEPTOR AGONIST AND MUSCARINIC RECEPTOR ANTAGONIST ACTIVITY

(75) Inventors: Mathai Mammen, Menlo Park, CA (US); Sarah Dunham, San Anselmo, CA (US)

(73) Assignee: Theravance, Inc., South San Francisco, CA (US)

( * ) Notice: Subject to any disclaimer, the term of this patent is extended or adjusted under 35 U.S.C. 154(b) by 43 days.

(21) Appl. No.: 12/903,365

(22) Filed: Oct. 13, 2010

(65) Prior Publication Data

US 2011/0034694 A1 Feb. 10, 2011

Related U.S. Application Data

(62) Division of application No. 12/001,363, filed on Dec. 11, 2007, now Pat. No. 7,838,535, which is a division of application No. 10/992,927, filed on Nov. 19, 2004, now Pat. No. 7,345,060.

(60) Provisional application No. 60/524,234, filed on Nov. 21, 2003.

(51) Int. Cl.
C07D 409/00 (2006.01)
(52) U.S. Cl. ........................................ 546/202
(58) Field of Classification Search .............. 546/202, 546/200
See application file for complete search history.

(56) References Cited

U.S. PATENT DOCUMENTS

| | | | |
|---|---|---|---|
| 5,621,010 A | 4/1997 | Sueda et al. | |
| 5,648,370 A | 7/1997 | Bonnert et al. | |
| 5,763,465 A | 6/1998 | Bonnert et al. | |
| 5,846,989 A | 12/1998 | Bonnert et al. | |
| 5,929,100 A | 7/1999 | Bonnert et al. | |
| 5,973,167 A | 10/1999 | Bonnert et al. | |
| 5,977,384 A | 11/1999 | Bonnert et al. | |
| 6,008,365 A | 12/1999 | Bonnert et al. | |
| 6,080,869 A | 6/2000 | Bonnert et al. | |
| 6,433,027 B1 | 8/2002 | Bozung et al. | |
| 6,635,764 B2 | 10/2003 | Mammen et al. | |
| 6,693,202 B1 | 2/2004 | Aggen et al. | |
| 7,094,790 B2 | 8/2006 | Cowart et al. | |
| 7,345,060 B2 | 3/2008 | Mammen et al. | |
| 7,838,535 B2 * | 11/2010 | Mammen et al. ............ | 514/323 |
| 2003/0018019 A1 | 1/2003 | Meade et al. | |
| 2004/0029919 A1 | 2/2004 | Mammen et al. | |
| 2004/0167167 A1 | 8/2004 | Mammen et al. | |
| 2004/0209860 A1 | 10/2004 | Mammen et al. | |
| 2004/0209915 A1 | 10/2004 | Mammen et al. | |

FOREIGN PATENT DOCUMENTS

| | | |
|---|---|---|
| EP | 0 005 610 A2 | 11/1979 |
| EP | 0 419 397 A1 | 3/1991 |
| EP | 0 747 355 A1 | 12/1996 |
| EP | 0 863 141 A1 | 9/1998 |
| EP | 0 930 298 A1 | 7/1999 |
| WO | WO 92/08708 A1 | 5/1992 |
| WO | WO 93/20071 A1 | 10/1993 |
| WO | WO 93/23385 A1 | 11/1993 |
| WO | WO 93/24473 A1 | 12/1993 |
| WO | WO 95/06635 A1 | 3/1995 |
| WO | WO 97/10227 A1 | 3/1997 |
| WO | WO 97/23470 A1 | 7/1997 |
| WO | WO 99/09018 A1 | 2/1999 |
| WO | WO 99/31086 A1 | 6/1999 |
| WO | WO 99/64043 A1 | 12/1999 |
| WO | WO 00/50413 A1 | 8/2000 |
| WO | WO 01/11933 A2 | 2/2001 |
| WO | WO 01/12167 A2 | 2/2001 |
| WO | WO 01/12191 A2 | 2/2001 |
| WO | WO 01/12192 A2 | 2/2001 |
| WO | WO 01/42212 A1 | 6/2001 |
| WO | WO 01/42213 A1 | 6/2001 |
| WO | WO 02/06255 A2 | 1/2002 |
| WO | WO 02/051841 A1 | 7/2002 |
| WO | WO 2004/012684 A2 | 2/2004 |
| WO | WO 2004/016601 A1 | 2/2004 |

OTHER PUBLICATIONS

Austin et al., "QSAR and the Rational Design of Long-Acting Dual $D_2$-Receptor/$\beta_2$—Adrenoceptor Agonists", J. Med. Chem., 46, pp. 3210-3220 (2003).
Birrell et al., "Effect of dopamine receptor agonists on sensory nerve activity: possible therapeutic targets for the treatment of asthma and COPD", British Journal of Pharmacology, 136, pp. 620-628 (2002).
Bonnert et al., "Dual $D_2$-Receptor and $\beta_2$—Adrenoceptor Agonists for the Treatment of Airway Diseases. 1. Discovery and Biological Evaluation of Some 7-(2-Aminoethyl)-4-hydroxybenzothiazol-2(3H)-one Analogues", J. Med. Chem. 41, pp. 4915-4917 (1998).

(Continued)

*Primary Examiner* — Rei-tsang Shiao
(74) *Attorney, Agent, or Firm* — Jeffrey A. Hagenah

(57) ABSTRACT

The invention is directed to compounds of formula I:

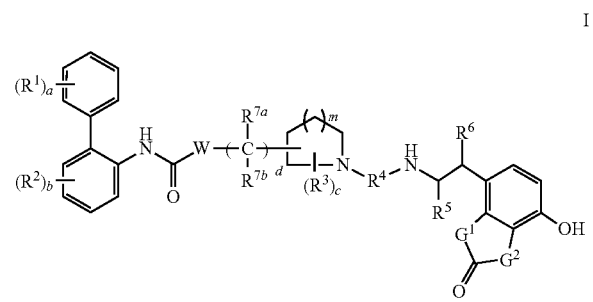

wherein $R^1$, $R^2$, $R^3$, $R^4$, $R^5$, $R^6$, $R^{7a}$, $R^{7b}$, W, $G^1$, $G^2$, a, b, c, d and m are as defined in the specification, or a pharmaceutically acceptable salt or solvate or stereoisomer thereof. The invention is also directed to pharmaceutical compositions comprising such compounds; methods of using such compounds; and process and intermediates for preparing such compounds.

15 Claims, No Drawings

OTHER PUBLICATIONS

Fozard et al., "Inhibition by viozan of extravasation induced in rat trachea by capsaicin is mediated exclusively by $\beta_2$-Adrenoceptors", Naunyn-Schmiedeberg's Arch Pharmacol 364: pp. 570-572 (2001).

Graul et al., Viozan™, Drugs of the Future 2000, 25(2): pp. 165-169.

Naito et al., "Selective Muscarinic Antagonists. II. [1)]Synthesis and Antimuscarinic Properties of Biphenylylcarbamate Derivatives", Chem. Pharm. Bull. 46(8), pp. 1286-1294 (1998).

Newbold et al., "Dual $D_2$ Dopamine Receptor and $\beta_2$-Adrenoceptor Agonists for the Modulation of Sensory Nerves in COPD", Hansel TT, Barnes PJ (eds): New Drugs for Asthma, Allergy and COPD, Prog Respir Res. Basel, Karger, vol. 31, pp. 68-71 (2001).

Suzuki et al., "S1319: A Novel $\beta_2$-Adrenoceptor Agonist From a Marine Sponge *Dysidea* SP.", Bioorganic & Medicinal Chemistry Letters 9, pp. 1361-1364 (1999).

Suzuki et al., "The effects of S1319, a novel marine sponge-derived $\beta_2$-adrenoceptor agonist, on IgE-mediated activation of human cultured mast cells", Inflamm. res. 49, pp. 086-094 (2000).

Suzuki et al., "Tracheal relaxing effects and $\beta_2$ adrenoceptor selectivity of S1319, a novel sponge-derived bronchodilator agent, in isolated guinea-pig tissues", British Journal of Pharmacology, 128, pp. 716-720 (1999).

Weinstock et al., "Synthesis and Evaluation of Non-Catechol D-1 and D-2 Dopamine Receptor Agonists: Benzimidazol-2-one, Benzoxazol-2-one, and the Highly Potent Benzothiazol-2-one 7-Ethylamines", J. Med. Chem., 30, pp. 1166-1176 (1987).

Office Action dated Apr. 24, 2007, for U.S. Appl. No. 10/992,927 (now U.S. 7,345,060 B2).

* cited by examiner

COMPOUNDS HAVING BETA2 ADRENERGIC RECEPTOR AGONIST AND MUSCARINIC RECEPTOR ANTAGONIST ACTIVITY

CROSS-REFERENCE TO RELATED APPLICATIONS

This application is a divisional application of U.S. application Ser. No. 12/001,363, filed Dec. 11, 2007; which application is a divisional application of U.S. application Ser. No. 10/992,927, filed Nov. 19, 2004 (now U.S. Pat. No. 7,345,060 B2); which application claims the benefit of U.S. Provisional Application No. 60/524,234, filed on Nov. 21, 2003; the entire disclosures of which are incorporated herein by reference in their entirety.

BACKGROUND OF THE INVENTION

1. Field of the Invention

The present invention relates to novel compounds having $\beta_2$ adrenergic receptor agonist and a muscarinic receptor antagonist activity. This invention also relates to pharmaceutical compositions comprising such compounds, processes and intermediates for preparing such compounds and methods of using such compounds to treat pulmonary disorders.

2. State of the Art

Pulmonary disorders, such as asthma and chronic obstructive pulmonary disease (COPD), are commonly treated with bronchodilators. One class of bronchodilator in widespread use consists of $\beta_2$ adrenergic receptor (adrenoceptor) agonists, such as albuterol, formoterol and salmeterol. These compounds are generally administered by inhalation. Another class of bronchodilator consists of muscarinic receptor antagonists (anticholinergic compounds), such as ipratropium and tiotropium. These compounds are also typically administered by inhalation.

Pharmaceutical compositions containing both a $\beta_2$ adrenergic receptor agonist and a muscarinic receptor antagonist are also known in the art for use in treating pulmonary disorders. For example, U.S. Pat. No. 6,433,027 discloses medicament compositions containing a muscarinic receptor antagonist, such as tiotropium bromide, and a $\beta_2$ adrenergic receptor agonist, such as formoterol fumarate.

Although compositions containing both a $\beta_2$ adrenergic receptor agonist and a muscarinic receptor antagonist are known, it would be highly desirable to provide compounds having both $\beta_2$ adrenergic receptor agonist and muscarinic receptor antagonist activity in the same molecule. Compounds possessing both $\beta_2$ adrenergic receptor agonist and muscarinic receptor antagonist activity are expected to be particularly useful as therapeutic agents since such bifunctional compounds would provide bronchodilation through two independent modes of action while having single molecule pharmacokinetics.

SUMMARY OF THE INVENTION

The present invention provides novel compounds that have been found to possess both $\beta_2$ adrenergic receptor agonist and muscarinic receptor antagonist activity. Such compounds are expected to be useful as therapeutic agents for treating pulmonary disorders. Certain compounds of this invention have also been found to possess affinity for dopamine $D_2$ receptors.

Accordingly, in one of its composition aspects, the present invention is directed to a compound of formula I:

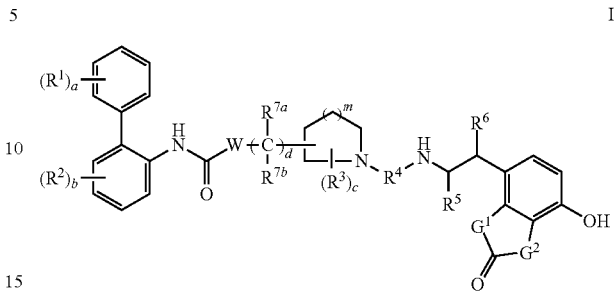

wherein
one of $G^1$ and $G^2$ represents NH and the other represents S, NH, O or $CH_2$;
W represents O or $NW^a$; where $W^a$ is hydrogen or (1-4C)alkyl;
each $R^1$ is independently selected from (1-4C)alkyl, (2-4C)alkenyl, (2-4C)alkynyl, (3-6C)cycloalkyl, cyano, halo, $-OR^{1a}$, $-C(O)OR^{1b}$, $-SR^{1c}$, $-S(O)R^{1d}$, $-S(O)_2R^{1e}$ and $-NR^{1f}R^{1g}$; where each of $R^{1a}$, $R^{1b}$, $R^{1c}$, $R^{1d}$, $R^{1e}$, $R^{1f}$ and $R^{1g}$ is independently hydrogen, (1-4C)alkyl or phenyl-(1-4C)alkyl;
each $R^2$ is independently selected from (1-4C)alkyl, (2-4C)alkenyl, (2-4C)alkynyl, (3-6C)cycloalkyl, cyano, halo, $-OR^{2a}$, $-C(O)OR^{2b}$, $-SR^{2c}$, $-S(O)R^{2d}$, $-S(O)_2R^{2e}$ and $-R^{2f}R^{2g}$; where each of $R^{2a}$, $R^{2b}$, $R^{2c}$, $R^{2d}$, $R^{2e}$, $R^{2f}$ and $R^{2g}$ is independently hydrogen, (1-4C)alkyl or phenyl-(1-4C)alkyl;
each $R^3$ is independently selected from (1-4C)alkyl, (2-4C)alkenyl, (2-4C)alkynyl, (3-6C)cycloalkyl, cyano, halo, $-OR^{3a}$, $-C(O)OR^{3b}$, $-SR^{3c}$, $-S(O)R^{3d}$, $-S(O)_2R^{3e}$ and $-NR^{3f}R^{3g}$; or two $R^3$ groups are joined to form (1-3C)alkylene, (2-3C)alkenylene or oxiran-2,3-diyl; where each of $R^{3a}$, $R^{3b}$, $R^{3c}$, $R^{3d}$, $R^{3e}$, $R^{3f}$ and $R^{3g}$ is independently hydrogen or (1-4C)alkyl;
$R^4$ represents a divalent hydrocarbon group containing from 4 to 28 carbon atoms and optionally containing from 1 to 10 heteroatoms selected independently from halo, oxygen, nitrogen and sulfur, provided that the number of contiguous atoms in the shortest chain between the two nitrogen atoms to which $R^4$ is attached is in the range of from 4 to 16;
$R^5$ represents hydrogen or (1-4C)alkyl;
$R^6$ represents hydrogen or hydroxyl;
each $R^{7a}$ and $R^{7b}$ is independently selected from hydrogen, (1-4C)alkyl, hydroxy and fluoro;
a is 0 or an integer of from 1 to 3;
b is 0 or an integer of from 1 to 3;
c is 0 or an integer of from 1 to 4;
d is 0 or an integer of from 1 to 5; and
m is 0 or an integer of from 1 to 3;
or a pharmaceutically acceptable salt or solvate or stereoisomer thereof.

Among the compounds of formula I, compounds of particular interest are those having an inhibitory constant ($K_i$) for the $M_3$ muscarinic receptor less than about 100 nM and a half maximal effective concentration $EC_{50}$ for agonism at the $\beta_2$ adrenergic receptor of less than about 100 nM. In particular, compounds of special interest are those in which the ratio of the inhibitory constant ($K_i$) for the $M_3$ muscarinic receptor to the $EC_{50}$ for agonism of the $\beta_2$ adrenergic receptor ranges from about 30:1 to about 1:30.

In another of its composition aspects, this invention is directed to a compound of formula Ia:

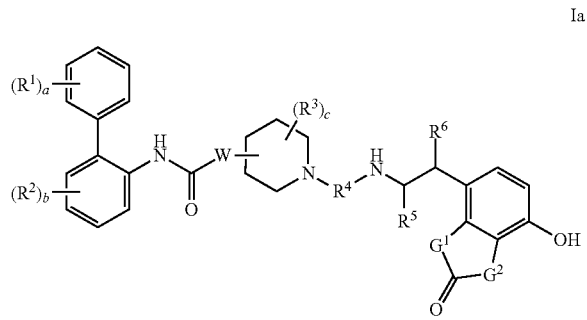

wherein
$R^1$, $R^2$, $R^3$, $R^4$, $R^5$, $R^6$, $G^1$, $G^2$, W, a, b and c is as defined herein (including any specific or preferred embodiments);
or a pharmaceutically acceptable salt or solvate or stereoisomer thereof.

In another of its composition aspects, this invention is directed to a compound of formula Ib:

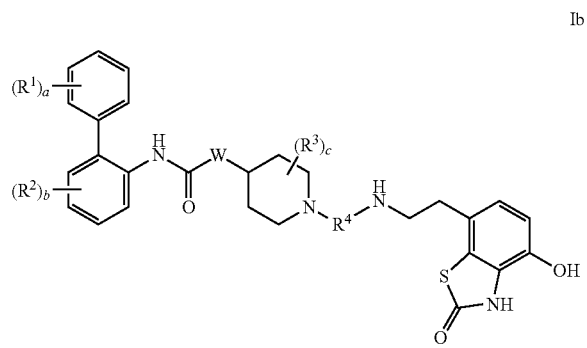

wherein
$R^1$, $R^2$, $R^3$, $R^4$, W, a, b and c is as defined herein (including any specific or preferred embodiments);
or a pharmaceutically acceptable salt or solvate or stereoisomer thereof.

In yet another of its composition aspects, this invention is directed to a compound of formula Ic:

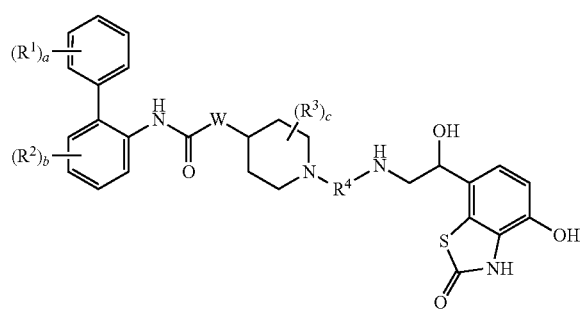

wherein
$R^1$, $R^2$, $R^3$, $R^4$, W, a, b and c is as defined herein (including any specific or preferred embodiments);
or a pharmaceutically acceptable salt or solvate or stereoisomer thereof.

In still another of its composition aspects, this invention is directed to a compound of formula Id:

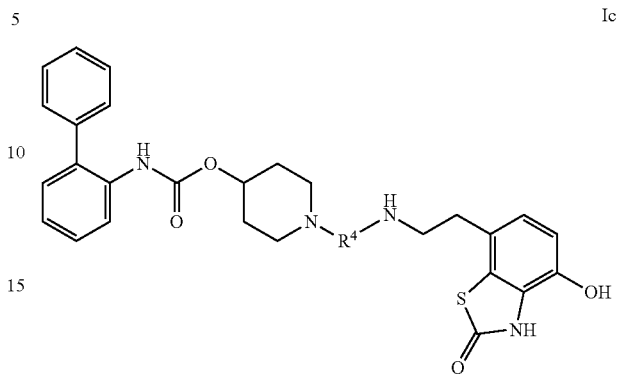

wherein
$R^4$ is as defined herein (including any specific or preferred embodiments);
or a pharmaceutically acceptable salt or solvate or stereoisomer thereof.

In another of its composition aspects, this invention is directed to a pharmaceutical composition comprising a pharmaceutically acceptable carrier and a therapeutically effective amount of a compound of this invention or a pharmaceutically acceptable salt or solvate or stereoisomer thereof. Such pharmaceutical compositions may optionally contain other therapeutic agents.

Accordingly, in one embodiment, this invention is directed to a pharmaceutical composition comprising a pharmaceutically acceptable carrier and a therapeutically effective amount of a compound of this invention or a pharmaceutically acceptable salt or solvate or stereoisomer thereof; and a therapeutically effective amount of a steroidal anti-inflammatory agent, such as a corticosteroid, or a pharmaceutically acceptable salt or solvate or stereoisomer thereof.

In another embodiment, this invention is directed to a pharmaceutical composition comprising a pharmaceutically acceptable carrier and a therapeutically effective amount of a compound of this invention or a pharmaceutically acceptable salt or solvate or stereoisomer thereof; and a therapeutically effective amount of a phosphodiesterase-4 (PDE4) inhibitor or a pharmaceutically acceptable salt or solvate or stereoisomer thereof.

Compounds of this invention possess both $\beta_2$ adrenergic receptor agonist activity and muscarinic receptor antagonist activity. Accordingly, the compounds of this invention are expected to be useful for treating pulmonary disorders, such as asthma and chronic obstructive pulmonary disease.

Accordingly, in one of its method aspects, this invention is directed to a method for treating a pulmonary disorder, the method comprising administering to a patient in need of treatment a therapeutically effective amount of a compound of this invention or a pharmaceutically acceptable salt or solvate or stereoisomer thereof.

Additionally, in another of its method aspects, this invention is directed to a method of producing bronchodilation in a patient, the method comprising administering to the patient a bronchodilation-producing amount of a compound of this invention or a pharmaceutically acceptable salt or solvate or stereoisomer thereof.

This invention is also directed to a method of treating chronic obstructive pulmonary disease or asthma, the method comprising administering to a patient in need of treatment a therapeutically effective amount of a compound of this invention or a pharmaceutically acceptable salt or solvate or stereoisomer thereof.

This invention is also directed to processes and novel intermediates useful for preparing compounds of formula I or a pharmaceutically acceptable salt or solvate or stereoisomer thereof. Accordingly, in another of its method aspects, this invention is directed to a process of preparing a compound of formula I, the process comprising:

(a) reacting a compound of formula 1 or a salt thereof, with a compound of formula 2;

(b) reacting a compound of formula 3 or a salt thereof, with a compound of formula 4;

(c) coupling a compound of formula 5 with a compound of formula 6;

(d) for a compound of formula I wherein $R^5$ represents a hydrogen atom, reacting a compound of formula 3 with a compound of formula 7a or 7b or a hydrate thereof, in the presence of a reducing agent;

(e) reacting a compound of formula 1 with a compound of formula 8 or a hydrate thereof, in the presence of a reducing agent;

(f) reacting a compound of formula 9, with a compound of formula 10; or (g) reacting a compound of formula 11 or a hydrate thereof, with a compound of formula 10, in the presence of a reducing agent;

and then removing any protecting groups to form a compound of formula I; wherein the compounds of formula 1-11 are as defined therein.

In one embodiment, the above process further comprises the step of forming a pharmaceutically acceptable salt of a compound of formula I. In other embodiments, this invention is directed to the other processes described herein; and to the product prepared by any of the processes described herein.

This invention is also directed to a compound of this invention or a pharmaceutically acceptable salt or solvate or stereoisomer thereof, for use in therapy or as a medicament.

Additionally, this invention is directed to the use of a compound of this invention or a pharmaceutically acceptable salt or solvate or stereoisomer thereof, for the manufacture of a medicament; especially for the manufacture of a medicament for the treatment of a pulmonary disorder.

DETAILED DESCRIPTION OF THE INVENTION

In one of its composition aspects, this invention is directed to novel compounds of formula I or pharmaceutically acceptable salts or solvates or stereoisomers thereof. These compounds may contain one or more chiral centers and therefore, when such chiral centers are present, this invention is directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions of this invention unless otherwise indicated, provided that the utility of the composition as a whole is not eliminated by the presence of such other isomers.

In particular, compounds of formula I in which $R^6$ represents a hydroxyl group contain a chiral center at the carbon atom indicated by the symbol * in the following formula:

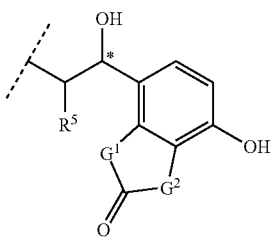

In one embodiment of this invention, the carbon atom identified by the symbol * has the (R) configuration. In this embodiment, it is preferred for compounds of formula I to have the (R) configuration at the carbon atom identified by the symbol * or to be enriched in a stereoisomeric form having the (R) configuration at this carbon atom. In another embodiment of this invention, the carbon atom identified by the symbol * has the (S) configuration. In this embodiment, it is preferred for compounds of formula I to have the (S) configuration at the carbon atom identified by the symbol * or to be enriched in a stereoisomeric form having the (S) configuration at this carbon atom. In some cases, in order to optimize the $\beta_2$ adrenergic agonist activity of the compounds of this invention, it is preferred that the carbon atom identified by the symbol * has the (R) configuration.

The compounds of this invention also contain several basic groups (e.g., amino groups) and therefore, such compounds can exist as the free base or in various salt forms. All such salt forms are included within the scope of this invention. Furthermore, solvates of compounds of this invention or salts thereof are included within the scope of this invention.

Additionally, where applicable, all cis-trans or E/Z isomers (geometric isomers), tautomeric forms and topoisomeric forms of the compounds of this invention are included within the scope of this invention unless otherwise specified.

The nomenclature used herein to name the compounds of this invention and intermediates thereof has generally been derived using the commercially-available AutoNom software (MDL, San Leandro, Calif.). For example, compounds of formula I wherein W is O have typically been named as ester derivatives of biphenyl-2-ylcarbamic acid; and compounds of formula I wherein W is $NW^a$ have been named as urea derivatives.

Representative Embodiments

The following substituents and values are intended to provide representative examples of various aspects and embodiments of this invention. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

In particular embodiments of the compounds of formula I, a and b are independently 0, 1 or 2; including 0 or 1. In one embodiment, both a and b are both 0.

When present, each $R^1$ may be at the 2, 3, 4, 5 or 6-position of the phenyl ring to which it is attached. In one embodiment, each $R^1$ is independently selected from (1-4C)alkyl, halo, $-OR^{1a}$ and $-NR^{1f}R^{1g}$; such as methyl, fluoro, chloro, bromo, hydroxy, methoxy, amino, methylamino, dimethylamino and the like. Particular values for $R^1$ are fluoro or chloro.

When present, each $R^2$ may be at the 3, 4, 5 or 6-position on the phenylene ring to which it is attached (where the carbon atom on the phenylene ring attached to the nitrogen atom is position 1). In one embodiment, each $R^2$ is independently selected from (1-4C)alkyl, halo, $-OR^{2a}$ and $-NR^{2f}R^{2g}$;

such as methyl, fluoro, chloro, bromo, hydroxy, methoxy, amino, methylamino, dimethylamino and the like. Particular values for $R^2$ are fluoro or chloro.

Each $R^{1a}$, $R^{1b}$, $R^{1c}$, $R^{1d}$, $R^{1e}$, $R^{1f}$ and $R^{1g}$ and $R^{2a}$, $R^{2b}$, $R^{2c}$, $R^{2d}$, $R^{2e}$, $R^{2f}$ and $R^{2g}$ as used in $R^1$ and $R^2$, respectively, is independently hydrogen, (1-4C)alkyl or phenyl-(1-4C)alkyl; such as hydrogen, methyl, ethyl, n-propyl, isopropyl, n-butyl, sec-butyl, isobutyl, tert-butyl and benzyl. In one embodiment, these groups are independently hydrogen or (1-3C)alkyl. In another embodiment, these groups are independently hydrogen, methyl or ethyl.

In one embodiment of this invention, W is O. In another embodiment, W is $NW^a$.

Generally, it has been found that compounds in which W represents O exhibit particularly high affinity for muscarinic and $\beta_2$ adrenergic receptors. Accordingly, in a particular embodiment of this invention, W preferably represents O.

When W is $NW^a$, $W^a$ is hydrogen or (1-4C)alkyl; such as hydrogen, methyl, ethyl, n-propyl, isopropyl, n-butyl, sec-butyl, isobutyl and tert-butyl. In one embodiment, $W^a$ is hydrogen or (1-3C)alkyl. In another embodiment, $W^a$ is hydrogen, methyl or ethyl; such as hydrogen or methyl. In yet another embodiment, $W^a$ is hydrogen and $NW^a$ is NH.

When b is 0 and m is 2 (such that W is attached to a piperidine ring), a particular embodiment of interest are compounds wherein W is attached to the piperidine ring at the 4-position with respect to the nitrogen atom of the piperidine ring.

In a particular embodiment of the compounds of formula I, c is 0, 1 or 2; including 0 or 1. In one embodiment, c is 0.

In a particular embodiment of the compounds of formula I, d is 0, 1 or 2; including 0 or 1. In one embodiment, d is 0. In another embodiment, d is 1.

In one embodiment, $R^{7a}$ and $R^{7b}$ are independently selected from hydrogen, methyl or ethyl. A particular value for $R^{7a}$ and $R^{7b}$ is hydrogen.

In a particular embodiment of the compounds of formula I, m is 0, 1 or 2; including 1 or 2. In one embodiment, m is 2. When m is 1, the resulting ring is a pyrrolidine ring; and when m is 2, the resulting ring is a piperidine ring.

In a particular embodiment of the compounds of formula I, c is 0, 1 or 2; including 0 or 1. In one embodiment, c is 0.

In a particular embodiment, each $R^3$ is independently selected from (1-4C)alkyl; such as methyl, ethyl, n-propyl, isopropyl, n-butyl, sec-butyl, isobutyl and tert-butyl. In another aspect, each $R^3$ is independently methyl or ethyl.

When m is 2, in one embodiment, each $R^3$ is at the 3, 4 or 5-position on the piperidine ring (where the nitrogen atom of the piperidine ring is position 1). In another embodiment, $R^3$ is at 4-position on the piperidine ring. In yet another embodiment, each $R^3$ is at the 2 or 6-position of the piperidine ring.

In another embodiment, $R^3$ is at the 1-position of the piperidine ring, i.e., on the nitrogen atom of the piperidine ring thus forming a quaternary amine salt. In a particular aspect of this embodiment, each $R^3$ is independently selected from (1-4C)alkyl; such as methyl, ethyl, n-propyl, isopropyl, n-butyl, sec-butyl, isobutyl and tert-butyl. In another aspect, each $R^3$ is independently methyl or ethyl.

In yet another embodiment, two $R^3$ groups are joined to form a (1-3C)alkylene or (2-3C)alkenylene group. For example, two $R^3$ groups at the 2 and 6-positions on the piperidine ring can be joined to form an ethylene bridge (i.e., the piperidine ring and the $R^3$ groups form an 8-azabicyclo[3.2.1]octane ring); or two $R^3$ groups at the 1 and 4-positions on the piperidine ring can be joined to form an ethylene bridge (i.e., the piperidine ring and the $R^3$ groups form an 1-azabicyclo[2.2.2]octane ring); or two $R^3$ groups at the 2 and 6-positions on the piperidine ring can be joined to form an ethenylene bridge (i.e., the piperidine ring and the $R^3$ groups form an 8-azabicyclo[3.2.1]oct-6-ene ring). In this embodiment, other $R^3$ groups as defined herein may also be present.

In still another embodiment, two $R^3$ groups are joined to form a oxiran-2,3-diyl group. For example, two $R^3$ groups at the 2 and 6-positions on the piperidine ring can be joined to form a 3-oxatricyclo[3.3.1.0$^{2,4}$]nonane ring). In this embodiment, other $R^3$ groups as defined herein may also be present.

Each $R^{3a}$, $R^{3b}$, $R^{3c}$, $R^{3d}$, $R^{3e}$, $R^{3f}$ and $R^{3g}$ as used in $R^3$ is independently hydrogen or (1-4C)alkyl; such as hydrogen, methyl, ethyl, n-propyl, isopropyl, n-butyl, sec-butyl, isobutyl and tert-butyl. In one embodiment, these groups are independently hydrogen or (1-3C)alkyl. In another embodiment, these groups are independently hydrogen, methyl or ethyl.

In one embodiment of the compounds of formula I, $R^5$ is hydrogen or (1-4C)alkyl; such as hydrogen, methyl, ethyl, n-propyl, isopropyl, n-butyl, sec-butyl, isobutyl and tert-butyl. In another embodiment, each $R^5$ is independently hydrogen, methyl or ethyl. In a particular embodiment, $R^5$ is hydrogen.

In one embodiment of this invention, $R^6$ is hydrogen. In another embodiment, $R^6$ is hydroxyl.

In separate embodiments, $G^1$ and $G^2$ are selected from:
$G^1$ is NH and $G^2$ is S;
$G^1$ is NH and $G^2$ is NH;
$G^1$ is NH and $G^2$ is O;
$G^1$ is NH and $G^2$ is $CH_2$;
$G^1$ is S and $G^2$ is NH;
$G^1$ is O and $G^2$ is NH; and
$G^1$ is $CH_2$ and $G^2$ is NH.

The divalent hydrocarbon group of this invention, $R^4$, contains from 4 to 28 carbon atoms and optionally contains from 1 to 10 heteroatoms selected independently from halo, oxygen, nitrogen and sulfur, provided that the number of contiguous atoms in the shortest chain between the two nitrogen atoms to which $R^4$ is attached is in the range of from 4 to 16. In one embodiment, this group contains from 4 to 24 carbon atoms, including from 6 to 20 carbon atoms, such as from 8 to 18 carbon atoms; and optionally contains from 1 to 8 heteroatoms, including from 1 to 6 heteroatoms.

The divalent hydrocarbon may contain any arrangement of atoms including alkylene, cycloalkylene, arylene, heteroarylene and heterocyclene groups or combinations thereof. The hydrocarbon group may be interrupted by one or more heteroatoms or combinations of heteroatoms and carbon atoms to form various functional groups, such as ethers, thioethers, amines, amides, esters, carbamates, ureas, sulfones, sulfoxides, sulfonamides and the like.

When determining the number of contiguous atoms in the shortest chain between the two nitrogen atoms to which divalent hydrocarbon group is attached, each contiguous atom of the chain is counted consecutively starting from the first atom in the divalent hydrocarbon group, i.e., the atom adjacent to the nitrogen atom of the azacycloalkyl group (i.e., a piperidinyl group when m is 2) in formula I, and ending with the last atom in the divalent hydrocarbon group, i.e., the atom adjacent to nitrogen atom the —NHCH($R^5$)— group in formula I. Where two or more chains are possible, the shortest chain is used to determine the number of contiguous atoms. As shown below, for example, when the divalent hydrocarbon group is —($CH_2$)$_2$—NHC(O)—$CH_2$-(phen-1,4-ylene)-$CH_2$—, there are 10 contiguous atoms in the shortest chain as shown below:

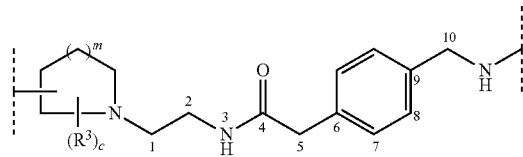

In a particular aspect of this invention, the divalent hydrocarbon group of the compounds of this invention (e.g., $R^4$ in formula I) is a divalent group of the formula:

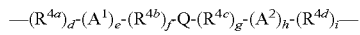

wherein d, e, f, g, h and i are each independently selected from 0 and 1;

$R^{4a}$, $R^{4b}$, $R^{4c}$ and $R^{4d}$ are each independently selected from (1-10C)alkylene, (2-10C)alkenylene and (2-10C)alkynylene, wherein each alkylene, alkenylene or alkynylene group is unsubstituted or substituted with from 1 to 5 substituents independently selected from (1-4C)alkyl, fluoro, hydroxy, phenyl and phenyl-(1-4C)alkyl;

$A^1$ and $A^2$ are each independently selected from (3-7C)cycloalkylene, (6-10C)arylene, —O-(6-10C)arylene, (6-10C)arylene-O—, (2-9C)heteroarylene, —O-(2-9C)heteroarylene, (2-9C)heteroarylene-O— and (3-6C)heterocyclene, wherein each cycloalkylene is unsubstituted or substituted with from 1 to 4 substitutents selected independently from (1-4C)alkyl, and each arylene, heteroarylene or heterocyclene group is unsubstituted or substituted with from 1 to 4 substituents independently selected from halo, (1-4C)alkyl, (1-4C)alkoxy, —S-(1-4C)alkyl, —S(O)-(1-4C)alkyl, —S(O)$_2$-(1-4C)alkyl, —C(O)O(1-4C)alkyl, carboxy, cyano, hydroxy, nitro, trifluoromethyl and trifluoromethoxy;

Q is selected from a bond, —O—, —C(O)O—, —OC(O)—, —S—, —S(O)—, —S(O)$_2$—, —N($Q^a$)C(O)—, —C(O)N($Q^b$)-, —N($Q^c$)S(O)$_2$—, —S(O)$_2$N($Q^d$)-, —N($Q^e$)C(O)N($Q^f$)-, —N($Q^g$)S(O)$_2$N($Q^h$)-, —OC(O)N($Q^i$)-, —N($Q^j$)C(O)O— and —N($Q^k$);

$Q^a$, $Q^b$, $Q^c$, $Q^d$, $Q^e$, $Q^f$, $Q^g$, $Q^h$, $Q^i$, $Q^j$, and $Q^k$ are each independently selected from hydrogen, (1-6C)alkyl, $A^3$ and (1-4C)alkylene-$A^4$, wherein the alkyl group is unsubstituted or substituted with from 1 to 3 substituents independently selected from fluoro, hydroxy and (1-4C)alkoxy; or together with the nitrogen atom and the group $R^{4b}$ or $R^{4c}$ to which they are attached, form a 4-6 membered azacycloalkylene group;

$A^3$ and $A^4$ are each independently selected from (3-6C)cycloalkyl, (6-10C)aryl, (2-9C)heteroaryl and (3-6C)heterocyclyl, wherein each cycloalkyl is unsubstituted or substituted with from 1 to 4 substitutents selected independently from (1-4C)alkyl and each aryl, heteroaryl or heterocyclyl group is unsubstituted or substituted with from 1 to 4 substituents independently selected from halo, (1-4C)alkyl and (1-4C)alkoxy.

In this embodiment, the values of each of the components $R^{4a}$, $A^1$, $R^{4b}$, Q, $R^{4c}$, $A^2$ and $R^{4d}$ are selected such that the number of contiguous atoms in the shortest chain between the two nitrogen atoms to which divalent hydrocarbon group is attached is in the range of from 4 to 16, (specifically, 4, 5, 6, 7, 8, 9, 10, 11, 12, 13, 14, 15 or 16); including 8, 9, 10, 11, 12, 13 or 14; such as 8, 9, 10 or 11; or 9 or 10. When selecting values for each variable, it will be appreciated by those skilled in the art that values should be selected such that a chemically stable group is formed.

In one embodiment, $R^{4a}$ is selected from (1-10C)alkylene, (2-10C)alkenylene and (2-10C)alkynylene wherein the alkylene group is unsubstituted or substituted with 1 or 2 substituents independently selected from (1-4C)alkyl, hydroxy and phenyl. Representative examples of particular values for $R^{4a}$ are —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)CH(CH$_3$)—, —(CH$_2$)C(CH$_3$)$_2$—, and —(CH$_2$)$_2$C(phenyl)$_2$-. In another aspect, $R^{4a}$ is —(CH$_2$)C(=CH$_2$)—.

In one embodiment, d is 1.

In one embodiment, $A^1$ is an optionally substituted (3-7C)cycloalkylene group; including a cyclohexylene group, such as cyclohex-1,4-ylene and cyclohex-1,3-ylene; and a cyclopentylene group, such as cyclopent-1,3-ylene.

In another embodiment, $A^1$ is an optionally substituted (6-10C)arylene group, including a phenylene group, such as phen-1,4-ylene, phen-1,3-ylene and phen-1,2-ylene; and a naphthylene group, such as naphth-1,4-ylene and napth-1,5-ylene.

In yet another embodiment, $A^1$ is an optionally substituted (2-9C)heteroarylene group, including a pyridylene group, such as pyrid-1,4-ylene; a furylene group, such as fur-2,5-ylene and fur-2,4-ylene; a thienylene group, such as thien-2,5-ylene and thien-2,4-ylene; and a pyrrolylene, such as pyrrol-2,5-ylene and pyrrol-2,4-ylene.

In still another embodiment, $A^1$ is an optionally substituted (3-6C)heterocyclene group, including a piperidinylene group, such as piperidin-1,4-ylene; and a pyrrolidinylene group, such as pyrrolidin-2,5-ylene.

In a particular embodiment, $A^1$ is an optionally substituted phenylene, thienylene, cyclopentylene, cyclohexylene or piperidinylene.

In one embodiment, e is 0.

In a particular embodiment, $R^{4b}$ is (1-5C)alkylene. Representative examples of particular values for $R^{4b}$ are —CH$_2$—, —(CH$_2$)$_2$—, —(CH$_2$)$_3$—, —(CH$_2$)$_4$—, —(CH$_2$)$_5$—; including methylene, ethylene and propylene.

In one embodiment, f is 0.

In a particular embodiment, Q is selected from a bond, —N($Q^a$)C(O)—, —C(O)N($Q^b$)-, —N($Q^c$)S(O)$_2$—, —S(O)$_2$N($Q^d$)-, —N($Q^e$)C(O)N($Q^f$)-, —OC(O)N($Q^i$)-, —N($Q^j$)C(O)O— or —N($Q^k$); such as where Q is a bond, —N($Q^a$)C(O)— or —C(O)N($Q^b$)-. Representative examples of particular values for Q are a bond, O, NH, —C(O)NH—, —C(O)N(CH$_3$)—, —NHC(O)—, —N(CH$_3$)C(O)—, —S(O)$_2$NH—, —S(O)$_2$N(CH$_3$)—, —NHS(O)$_2$—, —N(CH$_3$)S(O)$_2$— and —NHC(O)NH—. Another example of a value for Q, together with $R^{4c}$, is —C(O)(piperidin-1,4-ylene).

In one embodiment, $Q^a$, $Q^b$, $Q^c$, $Q^d$, $Q^e$, $Q^f$, $Q^g$, $Q^h$, $Q^i$, $Q^j$ and $Q^k$ are each independently selected from hydrogen and (1-6C)alkyl, wherein the alkyl group is unsubstituted or substituted with from 1 to 3 substituents independently selected from fluoro, hydroxy and (1-4C)alkoxy. For example, $Q^a$, $Q^b$, $Q^c$, $Q^d$, $Q^e$, $Q^f$, $Q^g$, $Q^h$, $Q^i$, $Q^j$ and $Q^k$ are each independently selected from hydrogen, and (1-3C)alkyl, including hydrogen, methyl, ethyl, n-propyl and isopropyl. An example of a value for each of $Q^a$, $Q^b$, $Q^c$, $Q^d$, $Q^e$, $Q^f$, $Q^g$, $Q^h$, $Q^i$, $Q^j$ and $Q^k$ is hydrogen.

In another embodiment, $Q^a$, $Q^b$, $Q^c$, $Q^d$, $Q^e$, $Q^f$, $Q^g$, $Q^h$, $Q^i$, $Q^j$ and $Q^k$ together with the nitrogen atom and the group $R^{4b}$ or $R^{4c}$ to which they are attached, form a 4-6 membered azacycloalkylene group. For example, $Q^a$ and $Q^h$ together with the nitrogen atom and the group $R^{4b}$ or $R^{4c}$ to which they are attached, form a piperidin-4-ylene group. By way of illustration, when Q represents —N($Q^a$)C(O)— and $Q^a$ together with the nitrogen atom and the group $R^{4b}$ to which it is attached, forms a piperidin-4-ylene group, $R^4$ is a group of formula:

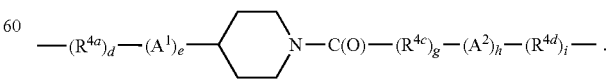

Similarly, when Q represents —C(O)N($Q^b$)- and $Q^b$ together with the nitrogen atom and the group $R^{4c}$ to which it is attached, forms a piperidin-4-ylene group, $R^4$ is a group of formula:

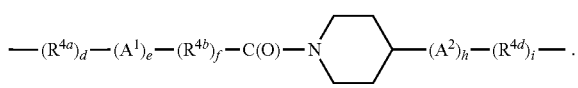

In a particular embodiment, $R^{4c}$ is (1-5C)alkylene. Representative examples of particular values for $R^{4c}$ are —$CH_2$—, —$(CH_2)_2$—, —$(CH_2)_3$—, —$(CH_2)_4$—, —$(CH_2)_5$—; including methylene, ethylene and propylene.

In one embodiment, $A^2$ is an optionally substituted (3-7C) cycloalkylene group; including a cyclohexylene group, such as cyclohex-1,4-ylene and cyclohex-1,3-ylene; and a cyclopentylene group, such as cyclopent-1,3-ylene.

In another embodiment, $A^2$ is an optionally substituted (6-10C)arylene group, including a phenylene group, such as phen-1,4-ylene, phen-1,3-ylene and phen-1,2-ylene; and a naphthylene group, such as naphth-1,4-ylene and napth-1,5-ylene.

In yet another embodiment, $A^2$ is an optionally substituted (2-9C)heteroarylene group, including a pyridylene group, such as pyrid-1,4-ylene; a furylene group, such as fur-2,5-ylene and fur-2,4-ylene; a thienylene group, such as thien-2,5-ylene and thien-2,4-ylene; and a pyrrolylene, such as pyrrol-2,5-ylene and pyrrol-2,4-ylene.

In still another embodiment, $A^2$ is an optionally substituted (3-6C)heterocyclene group, including a piperidinylene group, such as piperidin-1,4-ylene; and a pyrrolidinylene group, such as pyrrolidin-2,5-ylene.

In a particular embodiment, $A^2$ is optionally substituted phenylene, thienylene, cyclopentylene, cyclohexylene or piperidinylene.

By way of illustration, either $A^1$ or $A^2$ or both can be phenylene, such as phen-1,4-ylene or phen-1,3-ylene, where the phenylene group is unsubstituted or substituted with from 1 to 4 substituents independently selected from halo, (1-4C) alkyl, (1-4C)alkoxy, —S-(1-4C)alkyl, —S(O)-(1-4C)alkyl, —S(O)$_2$-(1-4C)alkyl, —C(O)O(1-4C)alkyl, carboxy, cyano, hydroxy, nitro, trifluoromethyl and trifluoromethoxy. Representative examples include phen-1,3-ylene, phen-1,4-ylene, 4-chlorophen-1,3-ylene, 6-chlorophen-1,3-ylene, 4-methylphen-1,3-ylene, 2-fluorophen-1,4-ylene, 2-chlorophen-1,4-ylene, 2-bromophen-1,4-ylene, 2-iodophen-1,4-ylene, 2-methylphen-1,4-ylene, 2-methoxyphen-1,4-ylene, 2-trifluoromethoxyphen-1,4-ylene, 3-nitrophen-1,4-ylene, 3-chlorophen-1,4-ylene, 2,5-difluorophen-1,4-ylene, 2,6-dichlorophen-1,4-ylene, 2,6-diiodophen-1,4-ylene, 2-chloro-6-methylphen-1,4-ylene, 2-chloro-5-methoxyphen-1,4-ylene, 2,3,5,6-tetrafluorophen-1,4-ylene.

Alternatively, $A^1$ or $A^2$ or both can be cyclopentylene or cyclohexylene; wherein the cyclopentylene or cyclohexylene group is unsubstituted or substituted with (1-4C)alkyl. Representative examples include cis-cyclopent-1,3-ylene, trans-cyclopent-1,3-ylene, cis-cyclohex-1,4-ylene and trans-cyclohex-1,4-ylene. $A^1$ or $A^2$ or both can also be optionally substituted thienylene or piperidinylene, for example, thien-2,5-ylene or piperidin-1,4-ylene.

In one embodiment, $R^{4d}$ is selected from (1-10C)alkylene, (2-10C)alkenylene and (2-10C)alkynylene wherein the alkylene is unsubstituted or substituted with 1 or 2 substituents independently selected from (1-4C)alkyl, hydroxy and phenyl. Representative examples of particular values for $R^{4d}$ are —$(CH_2)$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$— and —$(CH_2)CH(CH_3)$—$(CH_2)$—$C(CH_3)_2$—$(CH_2)_2$—.

In a particular embodiment, the divalent hydrocarbon group is a divalent group of the formula: —$(R^{4a})_d$— where $R^{4a}$ is (4-10C)alkylene. In one aspect of this embodiment, the divalent hydrocarbon group is a divalent group of the formula: —$(CH_2)_j$— where j is 8, 9 or 10. Examples of particular values for the divalent hydrocarbon group in this embodiment are —$(CH_2)_4$—, —$(CH_2)_5$—, —$(CH_2)_6$—, —$(CH_2)_7$—, —$(CH_2)_8$—, —$(CH_2)_9$—, and —$(CH_2)_{10}$—; including —$(CH_2)_8$—, —$(CH_2)_9$—, and —$(CH_2)_{10}$—.

In another particular embodiment, the divalent hydrocarbon group is a divalent group of the formula:

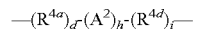

where $R^{4a}$ is (1-10C)alkylene, such as —$(CH_2)$—, —$(CH_2)_2$—, —$(CH_2)_3$—; $A^2$ is (6-10C)arylene, such as phen-1,4-ylene or phen-1,3-ylene, or (2-9C)heteroarylene, such as thien-2,5-ylene or thien-2,4-ylene; and $R^{4d}$ is (1-10C) alkylene, such as —$(CH_2)$—, —$(CH_2)_2$—, —$(CH_2)_3$—. Examples of particular values for the divalent hydrocarbon group in this embodiment are —$(CH_2)$-(phen-1,4-ylene)-$(CH_2)$—; —$(CH_2)$-(phen-1,4-ylene)-$(CH_2)_2$—; $(CH_2)$-(phen-1,4-ylene)-$(CH_2)_3$—; —$(CH_2)$-2-(phen-1,4-ylene)-$(CH_2)$—; —$(CH_2)$-2-(phen-1,4-ylene)-$(CH_2)_2$—; —$(CH_2)$-2-(phen-1,4-ylene)-$(CH_2)_3$—; —$(CH_2)$-3-(phen-1,4-ylene)-$(CH_2)$—; —$(CH_2)$-3-(phen-1,4-ylene)-$(CH_2)_2$—, —$(CH_2)$-3-(phen-1,4-ylene)-$(CH_2)_3$—, —$(CH_2)$-4-(phen-1,4-ylene)-$(CH_2)$—; —$(CH_2)$-4-(phen-1,4-ylene)-$(CH_2)_2$— and —$(CH_2)$-4-(phen-1,4-ylene)-$(CH_2)_3$—.

In yet another particular embodiment, the divalent hydrocarbon group is a divalent group of the formula:

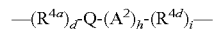

where Q is —O— or —$N(Q^k)$-; $Q^k$ is hydrogen or (1-3C) alkyl, such as methyl or ethyl; $R^{4a}$ is (1-10C)alkylene, such as —$(CH_2)$—, —$(CH_2)_2$—, —$(CH_2)_3$—; $A^2$ is (6-10C)arylene, such as phen-1,4-ylene or phen-1,3-ylene, or (2-9C)heteroarylene, such as thien-2,5-ylene or thien-2,4-ylene; and $R^{4d}$ is (1-10C)alkylene, such as —$(CH_2)$—, —$(CH_2)_2$—, —$(CH_2)_3$—. Examples of particular values for the divalent hydrocarbon group in this embodiment are —$(CH_2)_2$—O-(phen-1,4-ylene)-$(CH_2)$—; —$(CH_2)_2$—O-(phen-1,4-ylene)-$(CH_2)_2$—; —$(CH_2)_2$—O-(phen-1,4-ylene)-$(CH_2)_3$—; —$(CH_2)_3$—O-(phen-1,4-ylene)-$(CH_2)$—; —$(CH_2)_3$—O-(phen-1,4-ylene)-$(CH_2)_2$—; —$(CH_2)_3$—O-(phen-1,4-ylene)-$(CH_2)_3$—; —$(CH_2)_2$—NH-(phen-1,4-ylene)-$(CH_2)$—; —$(CH_2)_2$—NH-(phen-1,4-ylene)-$(CH_2)_2$—; —$(CH_2)_2$—NH-(phen-1,4-ylene)-$(CH_2)_3$—; —$(CH_2)_3$—NH-(phen-1,4-ylene)-$(CH_2)$—; —$(CH_2)_3$—NH-(phen-1,4-ylene)-$(CH_2)_2$— and —$(CH_2)_3$—NH-(phen-1,4-ylene)-$(CH_2)_3$—.

In yet another particular embodiment, the divalent hydrocarbon group is a divalent group of the formula:

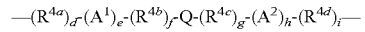

where Q is —$N(Q^a)C(O)$— or —$C(O)N(Q^b)$-. A particular value for the divalent hydrocarbon group in this embodiment is the formula:

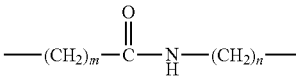

where m is an integer from 2 to 10; and n is an integer from 2 to 10; provided that m+n is an integer from 4 to 12. In this formula for $R^4$, d and g are 1 and e, f, h and i are 0; and $R^{4a}$ is —$(CH_2)_m$—, $R^{4c}$ is —$(CH_2)_n$— and Q is —$C(O)NH$—. Particular values for m are 2 or 3; and for n, 4, 5 or 6.

Another particular value for the divalent hydrocarbon group is the formula:

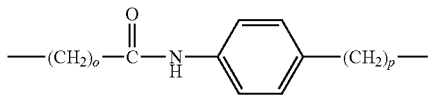

where o is an integer from 2 to 7; and p is an integer from 1 to 6; provided that o+p is an integer from 3 to 8. In this formula for $R^4$, d, h and i are 1 and e, f and g are 0; and $R^{4a}$ is —$(CH_2)_o$—, $A^2$ is phen-1,4-ylene, $R^{4d}$ is —$(CH_2)_p$— and Q is —C(O)NH—. Particular values for o are 2 or 3; and for p, 1 or 2. In this embodiment, the phen-1,4-ylene group may be optionally substituted as defined herein for $A^2$.

Another particular value for the divalent hydrocarbon group is the formula:

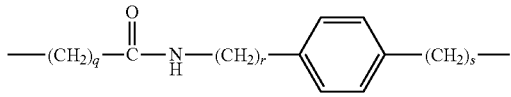

where q is an integer from 2 to 6; r is an integer from 1 to 5; and s is an integer from 1 to 5; provided that q+r+s is an integer from 4 to 8. In this formula for $R^4$, d, g, h and i are 1 and e and f are 0; and $R^{4a}$ is —$(CH_2)_q$—, $R^{4c}$ is —$(CH_2)_r$—, $A^2$ is 1,4-phenylene, $R^{4d}$ is —$(CH_2)_s$— and Q is —C(O)NH—. Particular values for q are 2 or 3; for r, 1 or 2; and for s, 1 or 2. In this embodiment, the phen-1,4-ylene group may be optionally substituted as defined herein for $A^2$.

Another particular value for the divalent hydrocarbon group is the formula:

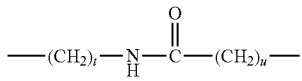

where t is an integer from 2 to 10; and u is an integer from 2 to 10; provided that t+u is an integer from 4 to 12. In this formula for $R^4$, d and g are 1 and e, f, h and i are 0; and $R^{4a}$ is —$(CH_2)_t$—, $R^{4c}$ is —$(CH_2)_u$— and Q is —NHC(O)—. Particular values for t are 2 or 3; and for u, 4, 5 or 6.

Another particular value for the divalent hydrocarbon group is the formula:

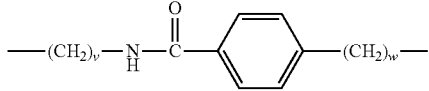

where v is an integer from 2 to 7; and w is an integer from 1 to 6; provided that v+w is an integer from 3 to 8. In this formula for $R^4$, d, h and i are 1 and e, f and g are 0; and $R^{4a}$ is —$(CH_2)_v$—, $A^2$ is 1,4-phenylene, $R^{4d}$ is —$(CH_2)_w$— and Q is —NHC(O)—. Particular values for v are 2 or 3; and for w, 1 or 2. In this embodiment, the phen-1,4-ylene group may be optionally substituted as defined herein for $A^2$.

Another particular value for the divalent hydrocarbon group is the formula:

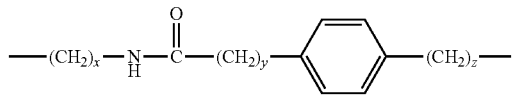

where x is an integer from 2 to 6; y is an integer from 1 to 5; and z is an integer from 1 to 5; provided that x+y+z is an integer from 4 to 8. In this formula for $R^4$, d, g, h and i are 1 and e and f are 0; and $R^{4a}$ is —$(CH_2)_x$—, $R^{4c}$ is —$(CH_2)_y$—, $A^2$ is 1,4-phenylene, $R^{4d}$ is —$(CH_2)_z$— and Q is —NHC(O)—. Particular values for x are 2 or 3; for y, 1 or 2; and for z, 1 or 2. In this embodiment, the phen-1,4-ylene group may be optionally substituted as defined herein for $A^2$.

By way of further illustration, the divalent hydrocarbon group can be a group selected from:
—$(CH_2)_7$—;
—$(CH_2)_8$—;
—$(CH_2)_9$—;
—$(CH_2)_{10}$—;
—$(CH_2)_{11}$—;
—$(CH_2)_2C(O)NH(CH_2)_5$—;
—$(CH_2)_2N(CH_3)C(O)(CH_2)_5$—;
—$(CH_2)_2C(O)NH(phen-1,4-ylene)CH_2$—;
—$(CH_2)_2NHC(O)(phen-1,4-ylene)CH_2$—;
—$(CH_2)_2NHC(O)NH(CH_2)_5$—;
—$(CH_2)_3NHC(O)NH(CH_2)_5$—;
—$(CH_2)_2C(O)NHCH_2(cyclohex-1,3-ylene)CH_2$—;
—$(CH_2)_2NHC(O)(cyclopent-1,3-ylene)$-;
—$(CH_2)_2NHC(O)NH(phen-1,4-ylene)(CH_2)_2$—;
1-[—$(CH_2)_2C(O)$](piperidin-4-yl)$(CH_2)_2$—;
—$(CH_2)_2NHC(O)(trans-cyclohex-1,4-ylene)CH_2$—;
—$(CH_2)_2NHC(O)(cis-cyclopent-1,3-ylene)$-;
—$(CH_2)_2NH(phen-1,4-ylene)(CH_2)_2$—;
1-[—$(CH_2)_2NHC(O)$](piperidin-4-yl)$(CH_2)_2$—;
—$CH_2$(phen-1,4-ylene)NH(phen-1,4-ylene)$CH_2$—;
—$(CH_2)_2C(O)NHCH_2$(phen-1,3-ylene)$CH_2$—;
—$(CH_2)_2C(O)NHCH_2$(pyrid-2,6-ylene)$CH_2$—;
—$(CH_2)_2C(O)NH(cis-cyclohex-1,4-ylene)CH_2$—;
—$(CH_2)_2C(O)NH(trans-cyclohex-1,4-ylene)CH_2$—;
—$(CH_2)_2NHC(O)(cis-cyclopent-1,3-ylene)CH_2$—;
—$(CH_2)_2N(CH_3)C(O)(phen-1,3-ylene)CH_2$—;
—$(CH_2)_2N(CH_3)C(O)(trans-cyclohex-1,4-ylene)CH_2$—;
—$(CH_2)_2C(O)NH(phen-1,4-ylene)CH_2$—;
—$(CH_2)_2C(O)NH(phen-1,4-ylene)C^*H(CH_3)$—((S)-isomer);
—$(CH_2)_2C(O)NH(phen-1,4-ylene)C^*H(CH_3)$—((R)-isomer);
2-[(S)—(—$CH_2$-](pyrrolidin-1-yl)C(O)$(CH_2)_4$—;
2-[(S)—(—$CH_2$-](pyrrolidin-1-yl)C(O)(phen-1,4-ylene)$CH_2$—;
—$(CH_2)_2C(O)NH(4-chlorophen-1,3-ylene)CH_2$—;
—$CH_2$(2-fluorophen-1,3-ylene)$CH_2$—;
—$(CH_2)_2C(O)NH(4-methylphen-1,3-ylene)CH_2$—;
—$(CH_2)_2C(O)NH(6-chlorophen-1,3-ylene)CH_2$—;
—$(CH_2)_2C(O)NH(2-chlorophen-1,4-ylene)CH_2$—;
—$(CH_2)_2C(O)NH(2,6-dichlorophen-1,4-ylene)CH_2$—;
—$(CH_2)_2NHC(O)NHCH_2$(phen-1,3-ylene)$CH_2$—;
4-[—$CH_2$-](piperidin-1-yl)C(O)(phen-1,4-ylene)$CH_2$—;
—$(CH_2)_2C(O)N(CH_2CH_3)$(phen-1,4-ylene)$CH_2$—;
1-[—$(CH_2)_2NHC(O)$](piperidin-4-yl)-;
—$(CH_2)_2C(O)NH(phen-1,4-ylene)(CH_2)_2$—;
—$(CH_2)_2NHC(O)(thien-2,5-ylene)CH_2$—;
—$(CH_2)_2N(CH_3)C(O)(3-nitrophen-1,4-ylene)CH_2$—;
—$(CH_2)_2N(CH_3)C(O)(trans-cyclohex-1,4-ylene)$-;
1-[—$CH_2$(2-fluorophen-1,3-ylene)$CH_2$](piperidin-4-yl)-;
5-[—$(CH_2)_2NHC(O)$](pyrid-2-yl)$CH_2$—;
—$(CH_2)_2$(phen-1,4-ylene)$(CH_2)_2$—;
—$(CH_2)_3$(thien-2,5-ylene)$(CH_2)_3$—;
—$(CH_2)_2$(phen-1,4-ylene)NH(phen-1,4-ylene)$(CH_2)_2$—;

—CH₂(phen-1,2-ylene)NH(phen-1,4-ylene)(CH₂)₂—;
1-[—CH₂(2-fluorophen-1,3-ylene)CH₂](piperidin-4-yl)(CH₂)₂—;
1-[—CH₂(2-fluorophen-1,3-ylene)CH₂](piperidin-4-yl)CH₂—;
—(CH₂)₂C(O)NH(3-chlorophen-1,4-ylene)CH₂—;
—(CH₂)₂C(O)NH(2-(CF₃O-)phen-1,4-ylene)CH₂—;
—(CH₂)₃(phen-1,3-ylene)NH(phen-1,4-ylene)(CH₂)₂—;
—(CH₂)₂S(O)₂NH(CH₂)₅—;
—CH₂(phen-1,3-ylene)NH(phen-1,4-ylene)(CH₂)₂—;
—(CH₂)₂C(O)NH(2-iodophen-1,4-ylene)CH₂—;
—(CH₂)₂C(O)NH(2-chloro-5-methoxyphen-1,4-ylene)CH₂—;
—(CH₂)₂C(O)NH(2-chloro-6-methylphen-1,4-ylene)CH₂—;
—(CH₂)₂N(CH₃)S(O)₂(phen-1,4-ylene)CH₂—;
—(CH₂)₂C(O)NH(2-bromophen-1,4-ylene)CH₂—;
—(CH₂)₃(phen-1,4-ylene)NH(phen-1,4-ylene)(CH₂)₂—;
—(CH₂)₃(phen-1,2-ylene)NH(phen-1,4-ylene)(CH₂)₂—;
1-[—CH₂(2-fluorophen-1,3-ylene)CH₂](piperidin-4-yl)(CH₂)₃—;
—(CH₂)₂C(O)NH(2-methoxyphen-1,4-ylene)CH₂—;
—(CH₂)₅NH(phen-1,4-ylene)(CH₂)₂—;
4-[—(CH₂)₂-](piperidin-1-yl)(phen-1,4-ylene)(CH₂)₂—;
—(CH₂)₂C(O)NH(phen-1,4-ylene)CH(CH₃)CH₂—;
—(CH₂)-2-(trans-cyclohex-1,4-ylene)NH(phen-1,4-ylene)(CH₂)₂—;
—(CH₂)₂C(O)NH(2-fluorophen-1,4-ylene)CH₂—;
—(CH₂)₂(phen-1,3-ylene)NH(phen-1,4-ylene)(CH₂)₂—;
—(CH₂)₂C(O)NH(2,5-difluorophen-1,4-ylene)CH₂—;
—(CH₂)₂NHC(O)(phen-1,4-ylene)(CH₂)₂—;
1-[—CH₂(pyrid-2,6-ylene)CH₂](piperidin-4-yl)CH₂—;
—(CH₂)₃NH(phen-1,4-ylene)(CH₂)₂—;
—(CH₂)₂NH(naphth-1,4-ylene)(CH₂)₂—;
—(CH₂)₃O(phen-1,4-ylene)CH₂—;
1-[—(CH₂)₃](piperidin-4-yl)CH₂—;
4-[—(CH₂)₂](piperidin-1-yl)C(O)(phen-1,4-ylene)CH₂—;
—(CH₂)₃(phen-1,4-ylene)NHC(O)(CH₂)₂—;
—(CH₂)₃O(phen-1,4-ylene)(CH₂)₂—;
2-[—(CH₂)₂](benzimidazol-5-yl)CH₂—;
—(CH₂)-2-(trans-cyclohex-1,4-ylene)NHC(O)(CH₂)₂—;
—(CH₂)-2-(trans-cyclohex-1,4-ylene)NHC(O)(CH₂)₄—;
—(CH₂)-2-(trans-cyclohex-1,4-ylene)NHC(O)(CH₂)₅—;
4-[—(CH₂)₂](piperidin-1-yl)C(O)(CH₂)₂—;
—(CH₂)₂NHC(O)NH(phen-1,4-ylene)CH₂—;
—(CH₂)₂N(CH₃)(CH₂)₂(cis-cyclohex-1,4-ylene)-;
—(CH₂)₂C(O)NH(2,3,5,6-tetrafluorophen-1,4-ylene)CH₂—;
—(CH₂)₂C(O)NH(2,6-diiodophen-1,4-ylene)CH₂—;
4-[—(CH₂)₂](piperidin-1-yl)C(O)(CH₂)₃—;
4-[—(CH₂)₂](piperidin-1-yl)C(O)(CH₂)₄—;
4-[—(CH₂)₂](piperidin-1-yl)C(O)(CH₂)₅—;
—(CH₂)₂C(O)NHCH₂(phen-1,4-ylene)CH₂—;
—(CH₂)₂NHC(O)NHCH₂(phen-1,4-ylene)CH₂—;
—(CH₂)₂C(O)NH(2-methylphen-1,4-ylene)CH₂—;
1-[—(CH₂)₃O(phen-1,4-ylene)(CH₂)₂](piperidin-4-yl)CH₂—;
—(CH₂)₂C(O)NHCH₂(phen-1,3-ylene)(CH₂)₂—;
—(CH₂)₂O(phen-1,3-ylene)CH₂—;
—(CH₂)₂N(CH₃)C(O)CH₂O(phen-1,4-ylene)CH₂—;
—(CH₂)₂N(CH₃)C(O)CH₂O(phen-1,3-ylene)CH₂—;
—(CH₂)₂N(CH₃)C(O)(fur-2,5-ylene)CH₂—;
—(CH₂)₂N(CH₃)C(O)(thien-2,5-ylene)CH₂—;
—(CH₂)₂O(phen-1,4-ylene)O(CH₂)₂—;
—(CH₂)₂(trans-cyclohex-1,4-ylene)NHC(O)(phen-1,4-ylene)CH₂—;
—(CH₂)₂(trans-cyclohex-1,4-ylene)NHC(O)CH₂O(phen-1,2-ylene)CH₂—;
—(CH₂)₂(trans-cyclohex-1,4-ylene)NHC(O)CH₂O(phen-1,3-ylene)CH₂—;
—(CH₂)₂(trans-cyclohex-1,4-ylene)NHC(O)CH₂O(phen-1,4-ylene)CH₂—;
—(CH₂)₂(trans-cyclohex-1,4-ylene)NHC(O)(fur-2,5-ylene)CH₂—;
—(CH₂)₂(trans-cyclohex-1,4-ylene)NHC(O)(thien-2,5-ylene)CH₂—;
4-[—(CH₂)₂](piperidin-1-yl)C(O)CH₂O(phen-1,2-ylene)CH₂—;
4-[—(CH₂)₂](piperidin-1-yl)C(O)CH₂O(phen-1,3-ylene)CH₂—;
4-[—(CH₂)₂](piperidin-1-yl)C(O)CH₂O(phen-1,4-ylene)CH₂—;
4-[—(CH₂)₂](piperidin-1-yl)C(O)(fur-2,5-ylene)CH₂—;
4-[—(CH₂)₂](piperidin-1-yl)C(O)(thien-2,5-ylene)CH₂—;
—(CH₂)₂(phen-1,4-ylene)NHC(O)(phen-1,3-ylene)CH₂—;
—(CH₂)₂(phen-1,4-ylene)NHC(O)(phen-1,4-ylene)CH₂—;
—(CH₂)₂(phen-1,4-ylene)NHC(O)CH₂O(phen-1,2-ylene)CH₂—;
—(CH₂)₂(phen-1,4-ylene)NHC(O)CH₂O(phen-1,3-ylene)CH₂—;
—(CH₂)₂(phen-1,4-ylene)NHC(O)CH₂O(phen-1,4-ylene)CH₂—;
—(CH₂)₂(phen-1,4-ylene)NHC(O)(fur-2,5-ylene)CH₂—;
—(CH₂)₂(phen-1,4-ylene)NHC(O)(thien-2,5-ylene)CH₂—;
—(CH₂)₂(trans-cyclohex-1,4-ylene)NHC(O)(phen-1,3-ylene)CH₂—;
—(CH₂)₃O(phen-1,3-ylene)CH₂—;
—CH₂CH(OH)CH₂NH(phen-1,4-ylene)(CH₂)₂—;
—(CH₂)₄NH(phen-1,4-ylene)(CH₂)₂—;
—(CH₂)₂C(O)NH(phen-1,4-ylene)CH₂NHC(O)CH₂—;
—(CH₂)₂C(O)NH(phen-1,4-ylene)(CH₂)₂NHC(O)CH₂—;
—(CH₂)₂C(O)NHCH₂(trans-cyclohex-1,4-ylene)CH₂—;
—(CH₂)₂NHC(O)(CH₂)₅—;
—(CH₂)₂O(phen-1,3-ylene)O(CH₂)₂—;
—(CH₂)₂O(phen-1,2-ylene)O(CH₂)₂—;
—CH₂(phen-1,2-ylene)O(phen-1,2-ylene)CH₂—;
—(CH₂)₂C(O)NH(CH₂)₆—;
—(CH₂)₃(phen-1,4-ylene)(CH₂)₃—;
—(CH₂)₃(phen-1,4-ylene)(CH₂)₂—;
—(CH₂)₄(phen-1,4-ylene)(CH₂)₂—;
—(CH₂)₃(furan-2,5-ylene)(CH₂)₃—;
—(CH₂)₂N(CH₃)C(O)NH(phen-1,4-ylene)(CH₂)₂—;
4-[—(CH₂)₂](piperidin-1-yl)C(O)NH(phen-1,4-ylene)(CH₂)₂—;
—(CH₂)₃(phen-1,3-ylene)(CH₂)₃—;
—(CH₂)₃(tetrahydrofuran-2,5-ylene)(CH₂)₃—; and
—(CH₂)₂O(phen-1,4-ylene)C(O)(CH₂)₂—.

Representative Subgeneric Groupings

The following subgeneric formulae and groupings are intended to provide representative examples of various aspects and embodiments of this invention and as such, they are not intended to exclude other embodiments or to limit the scope of this invention unless otherwise indicated.

A particular group of compounds of formula I are those disclosed in U.S. Provisional Application No. 60/524,234, filed on Nov. 21, 2003. This group includes compounds of formula Ia; wherein:

a is 0 or an integer of from 1 to 3;

each $R^1$ is independently selected from the group consisting of (1-4C)alkyl, (2-4C)alkenyl, (2-4C)alkynyl, (3-6C)cycloalkyl, cyano, halo, —$OR^{1a}$, —$C(O)OR^{1b}$, $SR^{1c}$, —$S(O)R^{1d}$, —$S(O)_2R^{1e}$, and —$NR^{1f}R^{1g}$;

each of $R^{1a}$, $R^{1b}$, $R^{1c}$, $R^{1d}$, $R^{1e}$, $R^{1f}$ and $R^{1g}$ is independently hydrogen or (1-4C)alkyl;

b is 0 or an integer of from 1 to 3;

each $R^2$ is independently selected from the group consisting of (1-4C)alkyl, (2-4C)alkenyl, (2-4C)alkynyl, (3-6C)cycloalkyl, cyano, halo, —$OR^{2a}$, —$C(O)OR^{2b}$, $SR^{2c}$, —$S(O)R^{2d}$, —$S(O)_2R^{2e}$, and —$NR^{2f}R^{2g}$;

each of $R^{2a}$, $R^{2b}$, $R^{2c}$, $R^{2d}$, $R^{2e}$, $R^{2f}$ and $R^{2g}$ is independently hydrogen or (1-4C)alkyl;

W is attached to the 3- or 4-position with respect to the nitrogen atom in the piperidine ring, and represents O or $NW^a$;

$W^a$ is hydrogen or (1-4C)alkyl;

c is 0 or an integer of from 1 to 4;

each $R^3$ is a substituent on carbon independently selected from the group consisting of (1-4C)alkyl, (2-4C)alkenyl, (2-4C)alkynyl, (3-6C)cycloalkyl, cyano, halo, —$OR^{3a}$, —$C(O)OR^{3b}$, $SR^{3c}$, —$S(O)R^{3d}$, —$S(O)_2R^{3e}$, and —$NR^{3f}R^{3g}$;

each of $R^{3a}$, $R^{3b}$, $R^{3c}$, $R^{3d}$, $R^{3e}$, $R^{3f}$ and $R^{3g}$ is independently hydrogen or (1-4C)alkyl;

$R^4$ is a divalent group of the formula:

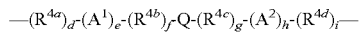

—$(R^{4a})_d$-$(A^1)_e$-$(R^{4b})_f$-Q-$(R^{4c})_g$-$(A^2)_h$-$(R^{4d})_i$— wherein d, e, f, g, h and i are each independently selected from 0 and 1;

$R^{4a}$, $R^{4b}$, $R^{4c}$ and $R^4$d are each independently selected from the group consisting of (1-10C)alkylene, (2-10C)alkenylene and (2-10C)alkynylene wherein each alkylene, alkenylene or alkynylene group is unsubstituted or substituted with from 1 to 5 substituents independently selected from the group consisting of (1-4C)alkyl, fluoro, hydroxy, phenyl and phenyl(1-4C)-alkyl;

$A^1$ and $A^2$ are each independently selected from (3-7C)cycloalkylene, (6-10C)arylene, (2-9C)heteroarylene and (3-6C)heterocyclene; wherein each cycloalkylene is unsubstituted or substituted with from 1 to 4 substitutents selected independently from (1-4C)alkyl and each arylene, heteroarylene or heterocyclene group is unsubstituted or substituted with from 1 to 4 substituents independently selected from the group consisting of halogen, (1-4C)alkyl and (1-4C)alkoxy;

Q is selected from the group consisting of a bond, —O—, —C(O)O—, —OC(O)—, —S—, —S(O)—, —$S(O)_2$—, —$N(Q^a)C(O)$—, —$C(O)N(Q^b)$—, —$N(Q^c)S(O)_2$—, —$S(O)_2N(Q^d)$-, —$N(Q^e)C(O)N(Q^f)$-, —$N(Q^g)S(O)_2N$ $(Q^h)$-, —$OC(O)N(Q^i)$-, —$N(Q^j)C(O)O$— and —$N(Q^k)$-;

$Q^a$, $Q^b$, $Q^c$, $Q^d$, $Q^e$, $Q^f$, $Q^g$, $Q^h$, $Q^i$, $Q^j$ and $Q^k$ are each independently selected from the group consisting of hydrogen, (1-6C)alkyl, $A^3$ and (1-4C)alkylene-$A^4$; wherein the alkyl group is unsubstituted or substituted with from 1 to 3 substituents independently selected from fluoro, hydroxy and (1-4C)alkoxy; or together with the nitrogen atom and the group $R^{4b}$ or $R^{4c}$ to which they are attached, form a 4-6 membered azacycloalkylene group;

$A^3$ and $A^4$ are each independently selected from (3-6C)cycloalkyl, (6-10C)aryl, (2-9C)heteroaryl and (3-6C)heterocyclyl; wherein each cycloalkyl is unsubstituted or substituted with from 1 to 4 substitutents selected independently from (1-4C)alkyl and each aryl, heteroaryl or heterocyclyl group is unsubstituted or substituted with from 1 to 4 substituents independently selected from the group consisting of halogen, (1-4C)alkyl and (1-4C)alkoxy;

provided that the number of contiguous atoms in the shortest chain between the two nitrogen atoms to which $R^4$ is attached is in the range of from 4 to 14;

$R^5$ represents hydrogen or (1-4C)alkyl;

$R^6$ represents hydrogen or hydroxyl; and one of $G^1$ and $G^2$ represents NH and the other represents S, NH, O or $CH_2$;

or a pharmaceutically-acceptable salt or solvate or stereoisomer thereof.

Another particular group of compounds of formula I are those where: a is 0; b is 0; c is 0; d is 0; m is 2; W is 0; W is attached at the 4-position of the piperidinyl ring; $R^5$ is hydrogen; and $R^4$, $R^6$, $G^1$ and $G^2$ are as defined herein; or a pharmaceutically acceptable salt or solvate or stereoisomer thereof.

Another particular group of compounds of formula I are those where: a is 0; b is 0; c is 0; d is 1; m is 2; W is 0; W is attached at the 4-position of the piperidinyl ring; $R^5$ is hydrogen; $R^{7a}$ and $R^{7b}$ are hydrogen; and $R^4$, $R^6$, $G^1$ and $G^2$ are as defined herein; or a pharmaceutically acceptable salt or solvate or stereoisomer thereof.

Still another particular group of compounds of formula I are those wherein: a is 0; b is 0; c is 0; d is 0; m is 2; W is NH; W is attached at the 4-position of the piperidinyl ring; $R^5$ is hydrogen; and $R^4$, $R^6$, $G^1$ and $G^2$ are as defined herein; or a pharmaceutically acceptable salt or solvate or stereoisomer thereof.

Another particular group of compounds of formula I are those of formula Ia as defined herein; or a pharmaceutically acceptable salt or solvate or stereoisomer thereof.

Another particular group of compounds of formula I are those of formula Ib as defined herein; or a pharmaceutically acceptable salt or solvate or stereoisomer thereof.

Another particular group of compounds of formula I are those of formula Ic as defined herein; or a pharmaceutically acceptable salt or solvate or stereoisomer thereof.

Another particular group of compounds of formula I are those of formula Id as defined herein; or a pharmaceutically acceptable salt or solvate or stereoisomer thereof.

Another particular group of compounds of formula I are those of formula Ia, Ib, Ic or Id as defined herein, wherein the piperidinyl ring is substituted at the 4-position with a methyl group; or a pharmaceutically acceptable salt or solvate or stereoisomer thereof.

Further examples of representative compounds of this invention are compounds of formula Ie:

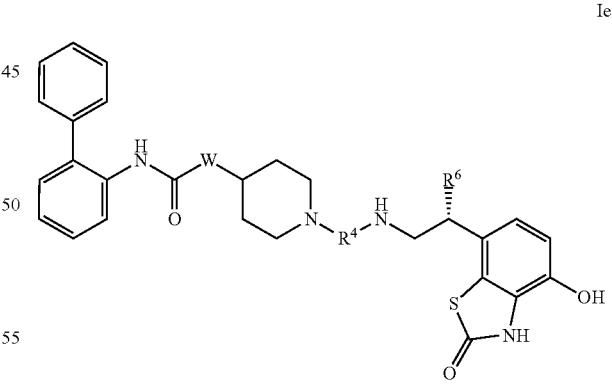

wherein W, $R^4$ and $R^6$ are as defined in Table I; or a pharmaceutically acceptable salt or solvate thereof.

TABLE I

| Ex. | W | $R^4$ | $R^6$ |
|---|---|---|---|
| 1 | O | —$(CH_2)_9$— | H |
| 2 | O | —$(CH_2)_2C(O)NH(phen-1,4-ylene)CH_2$— | H |
| 3 | NH | —$(CH_2)_2C(O)NH(phen-1,4-ylene)CH_2$— | H |

TABLE I-continued

| Ex. | W | R⁴ | R⁶ |
|---|---|---|---|
| 4 | O | —(CH$_2$)$_2$C(O)NH(phen-1,4-ylene)CH$_2$CH$_2$— | H |
| 5 | O | —(CH$_2$)$_2$(phen-1,3-ylene)NH(phen-1,4-ylene)(CH$_2$)$_2$— | H |
| 6 | O | —(CH$_2$)$_2$(phen-1,4-ylene)(CH$_2$)$_2$— | H |
| 7 | O | —(CH$_2$)$_2$(phen-1,4-ylene)NHC(O)(fur-2,5-ylene)CH$_2$— | H |
| 8 | O | —(CH$_2$)$_2$(phen-1,4-ylene)NHC(O)(phen-1,3-ylene)CH$_2$— | H |
| 9 | O | —(CH$_2$)$_2$(phen-1,4-ylene)NHC(O)(phen-1,4-ylene)CH$_2$— | H |
| 10 | O | —(CH$_2$)$_2$(phen-1,4-ylene)NHC(O)(thien-2,5-ylene)CH$_2$— | H |
| 11 | O | —(CH$_2$)$_2$(phen-1,4-ylene)NHC(O)CH$_2$O(phen-1,2-ylene)CH$_2$— | H |
| 12 | O | —(CH$_2$)$_2$(phen-1,4-ylene)NHC(O)CH$_2$O(phen-1,3-ylene)CH$_2$— | H |
| 13 | O | —(CH$_2$)$_2$(phen-1,4-ylene)NHC(O)CH$_2$O(phen-1,4-ylene)CH$_2$— | H |
| 14 | O | —(CH$_2$)$_2$-(trans-cyclohex-1,4-ylene)NH(phen-1,4-ylene)(CH$_2$)$_2$— | H |
| 15 | O | —(CH$_2$)$_2$-(trans-cyclohex-1,4-ylene)NHC(O)(CH$_2$)$_2$— | H |
| 16 | O | —(CH$_2$)$_2$-(trans-cyclohex-1,4-ylene)NHC(O)(CH$_2$)$_4$— | H |
| 17 | O | —(CH$_2$)$_2$-(trans-cyclohex-1,4-ylene)NHC(O)(CH$_2$)$_5$— | H |
| 18 | O | —(CH$_2$)$_2$(trans-cyclohex-1,4-ylene)NHC(O)(fur-2,5-ylene)CH$_2$— | H |
| 19 | O | —(CH$_2$)$_2$(trans-cyclohex-1,4-ylene)NHC(O)(phen-1,3-ylene)CH$_2$— | H |
| 20 | O | —(CH$_2$)$_2$(trans-cyclohex-1,4-ylene)NHC(O)(phen-1,4-ylene)CH$_2$— | H |
| 21 | O | —(CH$_2$)$_2$(trans-cyclohex-1,4-ylene)NHC(O)(thien-2,5-ylene)CH$_2$— | H |
| 22 | O | —(CH$_2$)$_2$(trans-cyclohex-1,4-ylene)NHC(O)CH$_2$O(phen-1,2-ylene)CH$_2$— | H |
| 23 | O | —(CH$_2$)$_2$(trans-cyclohex-1,4-ylene)NHC(O)CH$_2$O(phen-1,3-ylene)CH$_2$— | H |
| 24 | O | —(CH$_2$)$_2$(trans-cyclohex-1,4-ylene)NHC(O)CH$_2$O(phen-1,4-ylene)CH$_2$— | H |
| 25 | O | —(CH$_2$)$_2$C(O)N(CH$_2$CH$_3$)(phen-1,4-ylene)CH$_2$— | H |
| 26 | O | —(CH$_2$)$_2$C(O)NH(2-(CF$_3$O-)phen-1,4-ylene)CH$_2$— | H |
| 27 | O | —(CH$_2$)$_2$C(O)NH(2,3,5,6-tetrafluorophen-1,4-ylene)CH$_2$— | H |
| 28 | O | —(CH$_2$)$_2$C(O)NH(2,5-difluorophen-1,4-ylene)CH$_2$— | H |
| 29 | O | —(CH$_2$)$_2$C(O)NH(2,6-dichlorophen-1,4-ylene)CH$_2$— | H |
| 30 | O | —(CH$_2$)$_2$C(O)NH(2,6-diiodophen-1,4-ylene)CH$_2$— | H |
| 31 | O | —(CH$_2$)$_2$C(O)NH(2-bromophen-1,4-ylene)CH$_2$— | H |
| 32 | O | —(CH$_2$)$_2$C(O)NH(2-chloro-5-methoxyphen-1,4-ylene)CH$_2$— | H |
| 33 | O | —(CH$_2$)$_2$C(O)NH(2-chloro-6-methylphen-1,4-ylene)CH$_2$— | H |
| 34 | O | —(CH$_2$)$_2$C(O)NH(2-chlorophen-1,4-ylene)CH$_2$— | H |
| 35 | O | —(CH$_2$)$_2$C(O)NH(2-fluorophen-1,4-ylene)CH$_2$— | H |
| 36 | O | —(CH$_2$)$_2$C(O)NH(2-iodophen-1,4-ylene)CH$_2$— | H |
| 37 | O | —(CH$_2$)$_2$C(O)NH(2-methoxyphen-1,4-ylene)CH$_2$— | H |
| 38 | O | —(CH$_2$)$_2$C(O)NH(2-methylphen-1,4-ylene)CH$_2$— | H |
| 39 | O | —(CH$_2$)$_2$C(O)NH(3-chlorophen-1,4-ylene)CH$_2$— | H |
| 40 | O | —(CH$_2$)$_2$C(O)NH(4-chlorophen-1,3-ylene)CH$_2$— | H |
| 41 | O | —(CH$_2$)$_2$C(O)NH(4-methylphen-1,3-ylene)CH$_2$— | H |
| 42 | O | —(CH$_2$)$_2$C(O)NH(6-chlorophen-1,3-ylene)CH$_2$— | H |
| 43 | O | —(CH$_2$)$_2$C(O)NH(CH$_2$)$_5$— | H |
| 44 | O | —(CH$_2$)$_2$C(O)NH(CH$_2$)$_6$— | H |
| 45 | O | —(CH$_2$)$_2$C(O)NH(cis-cyclohex-1,4-ylene)CH$_2$— | H |
| 46 | O | —(CH$_2$)$_2$C(O)NH(phen-1,4-ylene)(CH$_2$)$_2$NHC(O)CH$_2$— | H |
| 47 | O | —(CH$_2$)$_2$C(O)NH(phen-1,4-ylene)C*H(CH$_3$)—((S)-isomer) | H |
| 48 | O | —(CH$_2$)$_2$C(O)NH(phen-1,4-ylene)C*H(CH$_3$)—((R)-isomer) | H |
| 49 | O | —(CH$_2$)$_2$C(O)NH(phen-1,4-ylene)CH(CH$_3$)CH$_2$— | H |
| 50 | O | —(CH$_2$)$_2$C(O)NH(phen-1,4-ylene)CH$_2$NHC(O)CH$_2$— | H |
| 51 | O | —(CH$_2$)$_2$C(O)NH(trans-cyclohex-1,4-ylene)CH$_2$— | H |
| 52 | O | —(CH$_2$)$_2$C(O)NHCH$_2$(cyclohex-1,3-ylene)CH$_2$— | H |
| 53 | O | —(CH$_2$)$_2$C(O)NHCH$_2$(phen-1,3-ylene)(CH$_2$)$_2$— | H |
| 54 | O | —(CH$_2$)$_2$C(O)NHCH$_2$(phen-1,3-ylene)CH$_2$— | H |
| 55 | O | —(CH$_2$)$_2$C(O)NHCH$_2$(phen-1,4-ylene)CH$_2$— | H |
| 56 | O | —(CH$_2$)$_2$C(O)NHCH$_2$(pyrid-2,6-ylene)CH$_2$— | H |
| 57 | O | —(CH$_2$)$_2$C(O)NHCH$_2$(trans-cyclohex-1,4-ylene)CH$_2$— | H |
| 58 | O | —(CH$_2$)$_2$N(CH$_3$)(CH$_2$)$_2$(cis-cyclohex-1,4-ylene)- | H |
| 59 | O | —(CH$_2$)$_2$N(CH$_3$)C(O)(3-nitrophen-1,4-ylene)CH$_2$— | H |
| 60 | O | —(CH$_2$)$_2$N(CH$_3$)C(O)(CH$_2$)$_5$— | H |
| 61 | O | —(CH$_2$)$_2$N(CH$_3$)C(O)(fur-2,5-ylene)CH$_2$— | H |
| 62 | O | —(CH$_2$)$_2$N(CH$_3$)C(O)(phen-1,3-ylene)CH$_2$— | H |
| 63 | O | —(CH$_2$)$_2$N(CH$_3$)C(O)(thien-2,5-ylene)CH$_2$— | H |
| 64 | O | —(CH$_2$)$_2$N(CH$_3$)C(O)(trans-cyclohex-1,4-ylene)- | H |
| 65 | O | —(CH$_2$)$_2$N(CH$_3$)C(O)(trans-cyclohex-1,4-ylene)CH$_2$— | H |
| 66 | O | —(CH$_2$)$_2$N(CH$_3$)C(O)CH$_2$O(phen-1,3-ylene)CH$_2$— | H |
| 67 | O | —(CH$_2$)$_2$N(CH$_3$)C(O)CH$_2$O(phen-1,4-ylene)CH$_2$— | H |
| 68 | O | —(CH$_2$)$_2$N(CH$_3$)C(O)NH(phen-1,4-ylene)(CH$_2$)$_2$— | H |
| 69 | O | —(CH$_2$)$_2$N(CH$_3$)S(O)$_2$(phen-1,4-ylene)CH$_2$— | H |
| 70 | O | —(CH$_2$)$_2$NH(naphth-1,4-ylene)(CH$_2$)$_2$— | H |
| 71 | O | —(CH$_2$)$_2$NH(phen-1,4-ylene)(CH$_2$)$_2$— | H |
| 72 | O | —(CH$_2$)$_2$NHC(O)(CH$_2$)$_5$— | H |
| 73 | O | —(CH$_2$)$_2$NHC(O)(cis-cyclopent-1,3-ylene)- | H |
| 74 | O | —(CH$_2$)$_2$NHC(O)(cis-cyclopent-1,3-ylene)CH$_2$— | H |
| 75 | O | —(CH$_2$)$_2$NHC(O)(phen-1,4-ylene)(CH$_2$)$_2$— | H |
| 76 | O | —(CH$_2$)$_2$NHC(O)(phen-1,4-ylene)CH$_2$— | H |
| 77 | O | —(CH$_2$)$_2$NHC(O)(thien-2,5-ylene)CH$_2$— | H |
| 78 | O | —(CH$_2$)$_2$NHC(O)(trans-cyclohex-1,4-ylene)CH$_2$— | H |

TABLE I-continued

| Ex. | W | R⁴ | R⁶ |
|---|---|---|---|
| 79 | O | —(CH₂)₂NHC(O)NH(CH₂)₅— | H |
| 80 | O | —(CH₂)₂NHC(O)NH(phen-1,4-ylene)(CH₂)₂— | H |
| 81 | O | —(CH₂)₂NHC(O)NH(phen-1,4-ylene)CH₂— | H |
| 82 | O | —(CH₂)₂NHC(O)NHCH₂(phen-1,3-ylene)CH₂— | H |
| 83 | O | —(CH₂)₂NHC(O)NHCH₂(phen-1,4-ylene)CH₂— | H |
| 84 | O | —(CH₂)₂O(phen-1,2-ylene)O(CH₂)₂— | H |
| 85 | O | —(CH₂)₂O(phen-1,3-ylene)CH₂— | H |
| 86 | O | —(CH₂)₂O(phen-1,3-ylene)O(CH₂)₂— | H |
| 87 | O | —(CH₂)₂O(phen-1,4-ylene)C(O)(CH₂)₂— | H |
| 88 | O | —(CH₂)₂O(phen-1,4-ylene)O(CH₂)₂— | H |
| 89 | O | —(CH₂)₂S(O)₂NH(CH₂)₅— | H |
| 90 | O | —(CH₂)₃(furan-2,5-ylene)(CH₂)₃— | H |
| 91 | O | —(CH₂)₃(phen-1,2-ylene)NH(phen-1,4-ylene)(CH₂)₂— | H |
| 92 | O | —(CH₂)₃(phen-1,3-ylene)(CH₂)₃— | H |
| 93 | O | —(CH₂)₃(phen-1,3-ylene)NH(phen-1,4-ylene)(CH₂)₂— | H |
| 94 | O | —(CH₂)₃(phen-1,4-ylene)(CH₂)₂— | H |
| 95 | O | —(CH₂)₃(phen-1,4-ylene)(CH₂)₃— | H |
| 96 | O | —(CH₂)₃(phen-1,4-ylene)NH(phen-1,4-ylene)(CH₂)₂— | H |
| 97 | O | —(CH₂)₃(phen-1,4-ylene)NHC(O)(CH₂)₂— | H |
| 98 | O | —(CH₂)₃(tetrahydrofuran-2,5-ylene)(CH₂)₃— | H |
| 99 | O | —(CH₂)₃(thien-2,5-ylene)(CH₂)₃— | H |
| 100 | O | —(CH₂)₃NH(phen-1,4-ylene)(CH₂)₂— | H |
| 101 | O | —(CH₂)₃NHC(O)NH(CH₂)₅— | H |
| 102 | O | —(CH₂)₃O(phen-1,3-ylene)CH₂— | H |
| 103 | O | —(CH₂)₃O(phen-1,4-ylene)(CH₂)₂— | H |
| 104 | O | —(CH₂)₃O(phen-1,4-ylene)CH₂— | H |
| 105 | O | —(CH₂)₄(phen-1,4-ylene)(CH₂)₂— | H |
| 106 | O | —(CH₂)₄NH(phen-1,4-ylene)(CH₂)₂— | H |
| 107 | O | —(CH₂)₅NH(phen-1,4-ylene)(CH₂)₂— | H |
| 108 | O | —(CH₂)₇— | H |
| 109 | O | —(CH₂)₈— | H |
| 110 | O | 1-[-(CH₂)₂C(O)](piperidin-4-yl)(CH₂)₂— | H |
| 111 | O | 1-[-(CH₂)₂NHC(O)](piperidin-4-yl)- | H |
| 112 | O | 1-[-(CH₂)₂NHC(O)](piperidin-4-yl)(CH₂)₂— | H |
| 113 | O | 1-[-(CH₂)₃](piperidin-4-yl)CH₂— | H |
| 114 | O | 1-[-(CH₂)₃O(phen-1,4-ylene)(CH₂)₂](piperidin-4-yl)CH₂— | H |
| 115 | O | 1-[-CH₂(2-fluorophen-1,3-ylene)CH₂](piperidin-4-yl)- | H |
| 116 | O | 1-[-CH₂(2-fluorophen-1,3-ylene)CH₂](piperidin-4-yl)(CH₂)₂— | H |
| 117 | O | 1-[-CH₂(2-fluorophen-1,3-ylene)CH₂](piperidin-4-yl)(CH₂)₃— | H |
| 118 | O | 1-[-CH₂(2-fluorophen-1,3-ylene)CH₂](piperidin-4-yl)CH₂— | H |
| 119 | O | 1-[-CH₂(pyrid-2,6-ylene)CH₂](piperidin-4-yl)CH₂— | H |
| 120 | O | 2-[-(CH₂)₂](benzimidazol-5-yl)CH₂— | H |
| 121 | O | 2-[(S)—(—CH₂-](pyrrolidin-1-yl)C(O)(CH₂)₄— | H |
| 122 | O | 2-[(S)—(—CH₂-](pyrrolidin-1-yl)C(O)(phen-1,4-ylene)CH₂— | H |
| 123 | O | 4-[-(CH₂)₂-](piperidin-1-yl)(phen-1,4-ylene)(CH₂)₂— | H |
| 124 | O | 4-[-(CH₂)₂](piperidin-1-yl)C(O)(CH₂)₂— | H |
| 125 | O | 4-[-(CH₂)₂](piperidin-1-yl)C(O)(CH₂)₃— | H |
| 126 | O | 4-[-(CH₂)₂](piperidin-1-yl)C(O)(CH₂)₄— | H |
| 127 | O | 4-[-(CH₂)₂](piperidin-1-yl)C(O)(CH₂)₅— | H |
| 128 | O | 4-[-(CH₂)₂](piperidin-1-yl)C(O)(fur-2,5-ylene)CH₂— | H |
| 129 | O | 4-[-(CH₂)₂](piperidin-1-yl)C(O)(phen-1,4-ylene)CH₂— | H |
| 130 | O | 4-[-(CH₂)₂](piperidin-1-yl)C(O)(thien-2,5-ylene)CH₂— | H |
| 131 | O | 4-[-(CH₂)₂](piperidin-1-yl)C(O)CH₂O(phen-1,2-ylene)CH₂— | H |
| 132 | O | 4-[-(CH₂)₂](piperidin-1-yl)C(O)CH₂O(phen-1,3-ylene)CH₂— | H |
| 133 | O | 4-[-(CH₂)₂](piperidin-1-yl)C(O)CH₂O(phen-1,4-ylene)CH₂— | H |
| 134 | O | 4-[-(CH₂)₂](piperidin-1-yl)C(O)NH(phen-1,4-ylene)(CH₂)₂— | H |
| 135 | O | 4-[-CH₂-](piperidin-1-yl)C(O)(phen-1,4-ylene)CH₂— | H |
| 136 | O | 5-[-(CH₂)₂NHC(O)](pyrid-2-yl)CH₂— | H |
| 137 | O | —CH₂(2-fluorophen-1,3-ylene)CH₂— | H |
| 138 | O | —CH₂(phen-1,2-ylene)NH(phen-1,4-ylene)(CH₂)₂— | H |
| 139 | O | —CH₂(phen-1,2-ylene)O(phen-1,2-ylene)CH₂— | H |
| 140 | O | —CH₂(phen-1,3-ylene)NH(phen-1,4-ylene)(CH₂)₂— | H |
| 141 | O | —CH₂(phen-1,4-ylene)NH(phen-1,4-ylene)(CH₂)₂— | H |
| 142 | O | —CH₂CH(OH)CH₂NH(phen-1,4-ylene)(CH₂)₂— | H |
| 143 | O | —(CH₂)₉— | OH |
| 144 | O | —(CH₂)₂C(O)NH(phen-1,4-ylene)CH₂— | OH |
| 145 | O | —(CH₂)₂C(O)NH(phen-1,4-ylene)CH₂CH₂— | OH |
| 146 | O | —(CH₂)₂(phen-1,3-ylene)NH(phen-1,4-ylene)(CH₂)₂— | OH |
| 147 | O | —(CH₂)₂(phen-1,4-ylene)(CH₂)₂— | OH |
| 148 | O | —(CH₂)₂(phen-1,4-ylene)NHC(O)(fur-2,5-ylene)CH₂— | OH |
| 149 | O | —(CH₂)₂(phen-1,4-ylene)NHC(O)(phen-1,3-ylene)CH₂— | OH |
| 150 | O | —(CH₂)₂(phen-1,4-ylene)NHC(O)(phen-1,4-ylene)CH₂— | OH |
| 151 | O | —(CH₂)₂(phen-1,4-ylene)NHC(O)(thien-2,5-ylene)CH₂— | OH |
| 152 | O | —(CH₂)₂(phen-1,4-ylene)NHC(O)CH₂O(phen-1,2-ylene)CH₂— | OH |
| 153 | O | —(CH₂)₂(phen-1,4-ylene)NHC(O)CH₂O(phen-1,3-ylene)CH₂— | OH |
| 154 | O | —(CH₂)₂(phen-1,4-ylene)NHC(O)CH₂O(phen-1,4-ylene)CH₂— | OH |
| 155 | O | —(CH₂)₂-(trans-cyclohex-1,4-ylene)NH(phen-1,4-ylene)(CH₂)₂— | OH |
| 156 | O | —(CH₂)₂-(trans-cyclohex-1,4-ylene)NHC(O)(CH₂)₂— | OH |

TABLE I-continued

| Ex. | W | $R^4$ | $R^6$ |
|---|---|---|---|
| 157 | O | —(CH$_2$)$_2$-(trans-cyclohex-1,4-ylene)NHC(O)(CH$_2$)$_4$— | OH |
| 158 | O | —(CH$_2$)$_2$-(trans-cyclohex-1,4-ylene)NHC(O)(CH$_2$)$_5$— | OH |
| 159 | O | —(CH$_2$)$_2$(trans-cyclohex-1,4-ylene)NHC(O)(fur-2,5-ylene)CH$_2$— | OH |
| 160 | O | —(CH$_2$)$_2$(trans-cyclohex-1,4-ylene)NHC(O)(phen-1,3-ylene)CH$_2$— | OH |
| 161 | O | —(CH$_2$)$_2$(trans-cyclohex-1,4-ylene)NHC(O)(phen-1,4-ylene)CH$_2$— | OH |
| 162 | O | —(CH$_2$)$_2$(trans-cyclohex-1,4-ylene)NHC(O)(thien-2,5-ylene)CH$_2$— | OH |
| 163 | O | —(CH$_2$)$_2$(trans-cyclohex-1,4-ylene)NHC(O)CH$_2$O(phen-1,2-ylene)CH$_2$— | OH |
| 164 | O | —(CH$_2$)$_2$(trans-cyclohex-1,4-ylene)NHC(O)CH$_2$O(phen-1,3-ylene)CH$_2$— | OH |
| 165 | O | —(CH$_2$)$_2$(trans-cyclohex-1,4-ylene)NHC(O)CH$_2$O(phen-1,4-ylene)CH$_2$— | OH |
| 166 | O | —(CH$_2$)$_2$C(O)N(CH$_2$CH$_3$)(phen-1,4-ylene)CH$_2$— | OH |
| 167 | O | —(CH$_2$)$_2$C(O)NH(2-(CF$_3$O-)phen-1,4-ylene)CH$_2$— | OH |
| 168 | O | —(CH$_2$)$_2$C(O)NH(2,3,5,6-tetrafluorophen-1,4-ylene)CH$_2$— | OH |
| 169 | O | —(CH$_2$)$_2$C(O)NH(2,5-difluorophen-1,4-ylene)CH$_2$— | OH |
| 170 | O | —(CH$_2$)$_2$C(O)NH(2,6-dichlorophen-1,4-ylene)CH$_2$— | OH |
| 171 | O | —(CH$_2$)$_2$C(O)NH(2,6-diiodophen-1,4-ylene)CH$_2$— | OH |
| 172 | O | —(CH$_2$)$_2$C(O)NH(2-bromophen-1,4-ylene)CH$_2$— | OH |
| 173 | O | —(CH$_2$)$_2$C(O)NH(2-chloro-5-methoxyphen-1,4-ylene)CH$_2$— | OH |
| 174 | O | —(CH$_2$)$_2$C(O)NH(2-chloro-6-methylphen-1,4-ylene)CH$_2$— | OH |
| 175 | O | —(CH$_2$)$_2$C(O)NH(2-chlorophen-1,4-ylene)CH$_2$— | OH |
| 176 | O | —(CH$_2$)$_2$C(O)NH(2-fluorophen-1,4-ylene)CH$_2$— | OH |
| 177 | O | —(CH$_2$)$_2$C(O)NH(2-iodophen-1,4-ylene)CH$_2$— | OH |
| 178 | O | —(CH$_2$)$_2$C(O)NH(2-methoxyphen-1,4-ylene)CH$_2$— | OH |
| 179 | O | —(CH$_2$)$_2$C(O)NH(2-methylphen-1,4-ylene)CH$_2$— | OH |
| 180 | O | —(CH$_2$)$_2$C(O)NH(3-chlorophen-1,4-ylene)CH$_2$— | OH |
| 181 | O | —(CH$_2$)$_2$C(O)NH(4-chlorophen-1,3-ylene)CH$_2$— | OH |
| 182 | O | —(CH$_2$)$_2$C(O)NH(4-methylphen-1,3-ylene)CH$_2$— | OH |
| 183 | O | —(CH$_2$)$_2$C(O)NH(6-chlorophen-1,3-ylene)CH$_2$— | OH |
| 184 | O | —(CH$_2$)$_2$C(O)NH(CH$_2$)$_5$— | OH |
| 185 | O | —(CH$_2$)$_2$C(O)NH(CH$_2$)$_6$— | OH |
| 186 | O | —(CH$_2$)$_2$C(O)NH(cis-cyclohex-1,4-ylene)CH$_2$— | OH |
| 187 | O | —(CH$_2$)$_2$C(O)NH(phen-1,4-ylene)(CH$_2$)$_2$NHC(O)CH$_2$— | OH |
| 188 | O | —(CH$_2$)$_2$C(O)NH(phen-1,4-ylene)C*H(CH$_3$)-((S)-isomer) | OH |
| 189 | O | —(CH$_2$)$_2$C(O)NH(phen-1,4-ylene)C*H(CH$_3$)-((R)-isomer) | OH |
| 190 | O | —(CH$_2$)$_2$C(O)NH(phen-1,4-ylene)CH(CH$_3$)CH$_2$— | OH |
| 191 | O | —(CH$_2$)$_2$C(O)NH(phen-1,4-ylene)CH$_2$NHC(O)CH$_2$— | OH |
| 192 | O | —(CH$_2$)$_2$C(O)NH(trans-cyclohex-1,4-ylene)CH$_2$— | OH |
| 193 | O | —(CH$_2$)$_2$C(O)NHCH$_2$(cyclohex-1,3-ylene)CH$_2$— | OH |
| 194 | O | —(CH$_2$)$_2$C(O)NHCH$_2$(phen-1,3-ylene)(CH$_2$)$_2$— | OH |
| 195 | O | —(CH$_2$)$_2$C(O)NHCH$_2$(phen-1,3-ylene)CH$_2$— | OH |
| 196 | O | —(CH$_2$)$_2$C(O)NHCH$_2$(phen-1,4-ylene)CH$_2$— | OH |
| 197 | O | —(CH$_2$)$_2$C(O)NHCH$_2$(pyrid-2,6-ylene)CH$_2$— | OH |
| 198 | O | —(CH$_2$)$_2$C(O)NHCH$_2$(trans-cyclohex-1,4-ylene)CH$_2$— | OH |
| 199 | O | —(CH$_2$)$_2$N(CH$_3$)(CH$_2$)$_2$(cis-cyclohex-1,4-ylene)- | OH |
| 200 | O | —(CH$_2$)$_2$N(CH$_3$)C(O)(3-nitrophen-1,4-ylene)CH$_2$— | OH |
| 201 | O | —(CH$_2$)$_2$N(CH$_3$)C(O)(CH$_2$)$_5$— | OH |
| 202 | O | —(CH$_2$)$_2$N(CH$_3$)C(O)(fur-2,5-ylene)CH$_2$— | OH |
| 203 | O | —(CH$_2$)$_2$N(CH$_3$)C(O)(phen-1,3-ylene)CH$_2$— | OH |
| 204 | O | —(CH$_2$)$_2$N(CH$_3$)C(O)(thien-2,5-ylene)CH$_2$— | OH |
| 205 | O | —(CH$_2$)$_2$N(CH$_3$)C(O)(trans-cyclohex-1,4-ylene)- | OH |
| 206 | O | —(CH$_2$)$_2$N(CH$_3$)C(O)(trans-cyclohex-1,4-ylene)CH$_2$— | OH |
| 207 | O | —(CH$_2$)$_2$N(CH$_3$)C(O)CH$_2$O(phen-1,3-ylene)CH$_2$— | OH |
| 208 | O | —(CH$_2$)$_2$N(CH$_3$)C(O)CH$_2$O(phen-1,4-ylene)CH$_2$— | OH |
| 209 | O | —(CH$_2$)$_2$N(CH$_3$)C(O)NH(phen-1,4-ylene)(CH$_2$)$_2$— | OH |
| 210 | O | —(CH$_2$)$_2$N(CH$_3$)S(O)$_2$(phen-1,4-ylene)CH$_2$— | OH |
| 211 | O | —(CH$_2$)$_2$NH(naphth-1,4-ylene)(CH$_2$)$_2$— | OH |
| 212 | O | —(CH$_2$)$_2$NH(phen-1,4-ylene)(CH$_2$)$_2$— | OH |
| 213 | O | —(CH$_2$)$_2$NHC(O)(CH$_2$)$_5$— | OH |
| 214 | O | —(CH$_2$)$_2$NHC(O)(cis-cyclopent-1,3-ylene)- | OH |
| 215 | O | —(CH$_2$)$_2$NHC(O)(cis-cyclopent-1,3-ylene)CH$_2$— | OH |
| 216 | O | —(CH$_2$)$_2$NHC(O)(phen-1,4-ylene)(CH$_2$)$_2$— | OH |
| 217 | O | —(CH$_2$)$_2$NHC(O)(phen-1,4-ylene)CH$_2$— | OH |
| 218 | O | —(CH$_2$)$_2$NHC(O)(thien-2,5-ylene)CH$_2$— | OH |
| 219 | O | —(CH$_2$)$_2$NHC(O)(trans-cyclohex-1,4-ylene)CH$_2$— | OH |
| 220 | O | —(CH$_2$)$_2$NHC(O)NH(CH$_2$)$_5$— | OH |
| 221 | O | —(CH$_2$)$_2$NHC(O)NH(phen-1,4-ylene)(CH$_2$)$_2$— | OH |
| 222 | O | —(CH$_2$)$_2$NHC(O)NH(phen-1,4-ylene)CH$_2$— | OH |
| 223 | O | —(CH$_2$)$_2$NHC(O)NHCH$_2$(phen-1,3-ylene)CH$_2$— | OH |
| 224 | O | —(CH$_2$)$_2$NHC(O)NHCH$_2$(phen-1,4-ylene)CH$_2$— | OH |
| 225 | O | —(CH$_2$)$_2$O(phen-1,2-ylene)O(CH$_2$)$_2$— | OH |
| 226 | O | —(CH$_2$)$_2$O(phen-1,3-ylene)CH$_2$— | OH |
| 227 | O | —(CH$_2$)$_2$O(phen-1,3-ylene)O(CH$_2$)$_2$— | OH |
| 228 | O | —(CH$_2$)$_2$O(phen-1,4-ylene)C(O)(CH$_2$)$_2$— | OH |
| 229 | O | —(CH$_2$)$_2$O(phen-1,4-ylene)O(CH$_2$)$_2$— | OH |
| 230 | O | —(CH$_2$)$_2$S(O)$_2$NH(CH$_2$)$_5$— | OH |
| 231 | O | —(CH$_2$)$_3$(furan-2,5-ylene)(CH$_2$)$_3$— | OH |

TABLE I-continued

| Ex. | W | R⁴ | R⁶ |
|---|---|---|---|
| 232 | O | —(CH₂)₃(phen-1,2-ylene)NH(phen-1,4-ylene)(CH₂)₂— | OH |
| 233 | O | —(CH₂)₃(phen-1,3-ylene)(CH₂)₃— | OH |
| 234 | O | —(CH₂)₃(phen-1,3-ylene)NH(phen-1,4-ylene)(CH₂)₂— | OH |
| 235 | O | —(CH₂)₃(phen-1,4-ylene)(CH₂)₂— | OH |
| 236 | O | —(CH₂)₃(phen-1,4-ylene)(CH₂)₃— | OH |
| 237 | O | —(CH₂)₃(phen-1,4-ylene)NH(phen-1,4-ylene)(CH₂)₂— | OH |
| 238 | O | —(CH₂)₃(phen-1,4-ylene)NHC(O)(CH₂)₂— | OH |
| 239 | O | —(CH₂)₃(tetrahydrofuran-2,5-ylene)(CH₂)₃— | OH |
| 240 | O | —(CH₂)₃(thien-2,5-ylene)(CH₂)₃— | OH |
| 241 | O | —(CH₂)₃NH(phen-1,4-ylene)(CH₂)₂— | OH |
| 242 | O | —(CH₂)₃NHC(O)NH(CH₂)₅— | OH |
| 243 | O | —(CH₂)₃O(phen-1,3-ylene)CH₂— | OH |
| 244 | O | —(CH₂)₃O(phen-1,4-ylene)(CH₂)₂— | OH |
| 245 | O | —(CH₂)₃O(phen-1,4-ylene)CH₂— | OH |
| 246 | O | —(CH₂)₄(phen-1,4-ylene)(CH₂)₂— | OH |
| 247 | O | —(CH₂)₄NH(phen-1,4-ylene)(CH₂)₂— | OH |
| 248 | O | —(CH₂)₅NH(phen-1,4-ylene)(CH₂)₂— | OH |
| 249 | O | —(CH₂)₇— | OH |
| 250 | O | —(CH₂)₈— | OH |
| 251 | O | 1-[-(CH₂)₂C(O)](piperidin-4-yl)(CH₂)₂— | OH |
| 252 | O | 1-[-(CH₂)₂NHC(O)](piperidin-4-yl)- | OH |
| 253 | O | 1-[-(CH₂)₂NHC(O)](piperidin-4-yl)(CH₂)₂— | OH |
| 254 | O | 1-[-(CH₂)₃](piperidin-4-yl)CH₂— | OH |
| 255 | O | 1-[-(CH₂)₃O(phen-1,4-ylene)(CH₂)₂](piperidin-4-yl)CH₂— | OH |
| 256 | O | 1-[-CH₂(2-fluorophen-1,3-ylene)CH₂](piperidin-4-yl)- | OH |
| 257 | O | 1-[-CH₂(2-fluorophen-1,3-ylene)CH₂](piperidin-4-yl)(CH₂)₂— | OH |
| 258 | O | 1-[-CH₂(2-fluorophen-1,3-ylene)CH₂](piperidin-4-yl)(CH₂)₃— | OH |
| 259 | O | 1-[-CH₂(2-fluorophen-1,3-ylene)CH₂](piperidin-4-yl)CH₂— | OH |
| 260 | O | 1-[-CH₂(pyrid-2,6-ylene)CH₂](piperidin-4-yl)CH₂— | OH |
| 261 | O | 2-[-(CH₂)₂](benzimidazol-5-yl)CH₂— | OH |
| 262 | O | 2-[(S)—(—CH₂-](pyrrolidin-1-yl)C(O)(CH₂)₄— | OH |
| 263 | O | 2-[(S)—(—CH₂-](pyrrolidin-1-yl)C(O)(phen-1,4-ylene)CH₂— | OH |
| 264 | O | 4-[-(CH₂)₂-](piperidin-1-yl)(phen-1,4-ylene)(CH₂)₂— | OH |
| 265 | O | 4-[-(CH₂)₂](piperidin-1-yl)C(O)(CH₂)₂— | OH |
| 266 | O | 4-[-(CH₂)₂](piperidin-1-yl)C(O)(CH₂)₃— | OH |
| 267 | O | 4-[-(CH₂)₂](piperidin-1-yl)C(O)(CH₂)₄— | OH |
| 268 | O | 4-[-(CH₂)₂](piperidin-1-yl)C(O)(CH₂)₅— | OH |
| 269 | O | 4-[-(CH₂)₂](piperidin-1-yl)C(O)(fur-2,5-ylene)CH₂— | OH |
| 270 | O | 4-[-(CH₂)₂](piperidin-1-yl)C(O)(phen-1,4-ylene)CH₂— | OH |
| 271 | O | 4-[-(CH₂)₂](piperidin-1-yl)C(O)(thien-2,5-ylene)CH₂— | OH |
| 272 | O | 4-[-(CH₂)₂](piperidin-1-yl)C(O)CH₂O(phen-1,2-ylene)CH₂— | OH |
| 273 | O | 4-[-(CH₂)₂](piperidin-1-yl)C(O)CH₂O(phen-1,3-ylene)CH₂— | OH |
| 274 | O | 4-[-(CH₂)₂](piperidin-1-yl)C(O)CH₂O(phen-1,4-ylene)CH₂— | OH |
| 275 | O | 4-[-(CH₂)₂](piperidin-1-yl)C(O)NH(phen-1,4-ylene)(CH₂)₂— | OH |
| 276 | O | 4-[-CH₂-](piperidin-1-yl)C(O)(phen-1,4-ylene)CH₂— | OH |
| 277 | O | 5-[-(CH₂)₂NHC(O)](pyrid-2-yl)CH₂— | OH |
| 278 | O | —CH₂(2-fluorophen-1,3-ylene)CH₂— | OH |
| 279 | O | —CH₂(phen-1,2-ylene)NH(phen-1,4-ylene)(CH₂)₂— | OH |
| 280 | O | —CH₂(phen-1,2-ylene)O(phen-1,2-ylene)CH₂— | OH |
| 281 | O | —CH₂(phen-1,3-ylene)NH(phen-1,4-ylene)(CH₂)₂— | OH |
| 282 | O | —CH₂(phen-1,4-ylene)NH(phen-1,4-ylene)CH₂— | OH |
| 283 | O | —CH₂CH(OH)CH₂NH(phen-1,4-ylene)(CH₂)₂— | OH |
| 284 | NH | —(CH₂)₉— | H |
| 285 | NH | —(CH₂)₂C(O)NH(phen-1,4-ylene)CH₂CH₂— | H |
| 286 | NH | —(CH₂)₂(phen-1,3-ylene)NH(phen-1,4-ylene)(CH₂)₂— | H |
| 287 | NH | —(CH₂)₂(phen-1,4-ylene)(CH₂)₂— | H |
| 288 | NH | —(CH₂)₂(phen-1,4-ylene)NHC(O)(fur-2,5-ylene)CH₂— | H |
| 289 | NH | —(CH₂)₂(phen-1,4-ylene)NHC(O)(phen-1,3-ylene)CH₂— | H |
| 290 | NH | —(CH₂)₂(phen-1,4-ylene)NHC(O)(phen-1,4-ylene)CH₂— | H |
| 291 | NH | —(CH₂)₂(phen-1,4-ylene)NHC(O)(thien-2,5-ylene)CH₂— | H |
| 292 | NH | —(CH₂)₂(phen-1,4-ylene)NHC(O)CH₂O(phen-1,2-ylene)CH₂— | H |
| 293 | NH | —(CH₂)₂(phen-1,4-ylene)NHC(O)CH₂O(phen-1,3-ylene)CH₂— | H |
| 294 | NH | —(CH₂)₂(phen-1,4-ylene)NHC(O)CH₂O(phen-1,4-ylene)CH₂— | H |
| 295 | NH | —(CH₂)₂-(trans-cyclohex-1,4-ylene)NH(phen-1,4-ylene)(CH₂)₂— | H |
| 296 | NH | —(CH₂)₂-(trans-cyclohex-1,4-ylene)NHC(O)(CH₂)₂— | H |
| 297 | NH | —(CH₂)₂-(trans-cyclohex-1,4-ylene)NHC(O)(CH₂)₄— | H |
| 298 | NH | —(CH₂)₂-(trans-cyclohex-1,4-ylene)NHC(O)(CH₂)₅— | H |
| 299 | NH | —(CH₂)₂(trans-cyclohex-1,4-ylene)NHC(O)(fur-2,5-ylene)CH₂— | H |
| 300 | NH | —(CH₂)₂(trans-cyclohex-1,4-ylene)NHC(O)(phen-1,3-ylene)CH₂— | H |
| 301 | NH | —(CH₂)₂(trans-cyclohex-1,4-ylene)NHC(O)(phen-1,4-ylene)CH₂— | H |
| 302 | NH | —(CH₂)₂(trans-cyclohex-1,4-ylene)NHC(O)(thien-2,5-ylene)CH₂— | H |
| 303 | NH | —(CH₂)₂(trans-cyclohex-1,4-ylene)NHC(O)CH₂O(phen-1,2-ylene)CH₂— | H |
| 304 | NH | —(CH₂)₂(trans-cyclohex-1,4-ylene)NHC(O)CH₂O(phen-1,3-ylene)CH₂— | H |
| 305 | NH | —(CH₂)₂(trans-cyclohex-1,4-ylene)NHC(O)CH₂O(phen-1,4-ylene)CH₂— | H |
| 306 | NH | —(CH₂)₂C(O)N(CH₂CH₃)(phen-1,4-ylene)CH₂— | H |

TABLE I-continued

| Ex. | W | R$^4$ | R$^6$ |
|---|---|---|---|
| 307 | NH | —(CH$_2$)$_2$C(O)NH(2-(CF$_3$O-)phen-1,4-ylene)CH$_2$— | H |
| 308 | NH | —(CH$_2$)$_2$C(O)NH(2,3,5,6-tetrafluorophen-1,4-ylene)CH$_2$— | H |
| 309 | NH | —(CH$_2$)$_2$C(O)NH(2,5-difluorophen-1,4-ylene)CH$_2$— | H |
| 310 | NH | —(CH$_2$)$_2$C(O)NH(2,6-dichlorophen-1,4-ylene)CH$_2$— | H |
| 311 | NH | —(CH$_2$)$_2$C(O)NH(2,6-diiodophen-1,4-ylene)CH$_2$— | H |
| 312 | NH | —(CH$_2$)$_2$C(O)NH(2-bromophen-1,4-ylene)CH$_2$— | H |
| 313 | NH | —(CH$_2$)$_2$C(O)NH(2-chloro-5-methoxyphen-1,4-ylene)CH$_2$— | H |
| 314 | NH | —(CH$_2$)$_2$C(O)NH(2-chloro-6-methylphen-1,4-ylene)CH$_2$— | H |
| 315 | NH | —(CH$_2$)$_2$C(O)NH(2-chlorophen-1,4-ylene)CH$_2$— | H |
| 316 | NH | —(CH$_2$)$_2$C(O)NH(2-fluorophen-1,4-ylene)CH$_2$— | H |
| 317 | NH | —(CH$_2$)$_2$C(O)NH(2-iodophen-1,4-ylene)CH$_2$— | H |
| 318 | NH | —(CH$_2$)$_2$C(O)NH(2-methoxyphen-1,4-ylene)CH$_2$— | H |
| 319 | NH | —(CH$_2$)$_2$C(O)NH(2-methylphen-1,4-ylene)CH$_2$— | H |
| 320 | NH | —(CH$_2$)$_2$C(O)NH(3-chlorophen-1,4-ylene)CH$_2$— | H |
| 321 | NH | —(CH$_2$)$_2$C(O)NH(4-chlorophen-1,3-ylene)CH$_2$— | H |
| 322 | NH | —(CH$_2$)$_2$C(O)NH(4-methylphen-1,3-ylene)CH$_2$— | H |
| 323 | NH | —(CH$_2$)$_2$C(O)NH(6-chlorophen-1,3-ylene)CH$_2$— | H |
| 324 | NH | —(CH$_2$)$_2$C(O)NH(CH$_2$)$_5$— | H |
| 325 | NH | —(CH$_2$)$_2$C(O)NH(CH$_2$)$_6$— | H |
| 326 | NH | —(CH$_2$)$_2$C(O)NH(cis-cyclohex-1,4-ylene)CH$_2$— | H |
| 327 | NH | —(CH$_2$)$_2$C(O)NH(phen-1,4-ylene)(CH$_2$)$_2$NHC(O)CH$_2$— | H |
| 328 | NH | —(CH$_2$)$_2$C(O)NH(phen-1,4-ylene)C*H(CH$_3$)-((S)-isomer) | H |
| 329 | NH | —(CH$_2$)$_2$C(O)NH(phen-1,4-ylene)C*H(CH$_3$)-((R)-isomer) | H |
| 330 | NH | —(CH$_2$)$_2$C(O)NH(phen-1,4-ylene)CH(CH$_3$)CH$_2$— | H |
| 331 | NH | —(CH$_2$)$_2$C(O)NH(phen-1,4-ylene)CH$_2$NHC(O)CH$_2$— | H |
| 332 | NH | —(CH$_2$)$_2$C(O)NH(trans-cyclohex-1,4-ylene)CH$_2$— | H |
| 333 | NH | —(CH$_2$)$_2$C(O)NHCH$_2$(cyclohex-1,3-ylene)CH$_2$— | H |
| 334 | NH | —(CH$_2$)$_2$C(O)NHCH$_2$(phen-1,3-ylene)(CH$_2$)$_2$— | H |
| 335 | NH | —(CH$_2$)$_2$C(O)NHCH$_2$(phen-1,3-ylene)CH$_2$— | H |
| 336 | NH | —(CH$_2$)$_2$C(O)NHCH$_2$(phen-1,4-ylene)CH$_2$— | H |
| 337 | NH | —(CH$_2$)$_2$C(O)NHCH$_2$(pyrid-2,6-ylene)CH$_2$— | H |
| 338 | NH | —(CH$_2$)$_2$C(O)NHCH$_2$(trans-cyclohex-1,4-ylene)CH$_2$— | H |
| 339 | NH | —(CH$_2$)$_2$N(CH$_3$)(CH$_2$)$_2$(cis-cyclohex-1,4-ylene)- | H |
| 340 | NH | —(CH$_2$)$_2$N(CH$_3$)C(O)(3-nitrophen-1,4-ylene)CH$_2$— | H |
| 341 | NH | —(CH$_2$)$_2$N(CH$_3$)C(O)(CH$_2$)$_5$— | H |
| 342 | NH | —(CH$_2$)$_2$N(CH$_3$)C(O)(fur-2,5-ylene)CH$_2$— | H |
| 343 | NH | —(CH$_2$)$_2$N(CH$_3$)C(O)(phen-1,3-ylene)CH$_2$— | H |
| 344 | NH | —(CH$_2$)$_2$N(CH$_3$)C(O)(thien-2,5-ylene)CH$_2$— | H |
| 345 | NH | —(CH$_2$)$_2$N(CH$_3$)C(O)(trans-cyclohex-1,4-ylene)- | H |
| 346 | NH | —(CH$_2$)$_2$N(CH$_3$)C(O)(trans-cyclohex-1,4-ylene)CH$_2$— | H |
| 347 | NH | —(CH$_2$)$_2$N(CH$_3$)C(O)CH$_2$O(phen-1,3-ylene)CH$_2$— | H |
| 348 | NH | —(CH$_2$)$_2$N(CH$_3$)C(O)CH$_2$O(phen-1,4-ylene)CH$_2$— | H |
| 349 | NH | —(CH$_2$)$_2$N(CH$_3$)C(O)NH(phen-1,4-ylene)(CH$_2$)$_2$— | H |
| 350 | NH | —(CH$_2$)$_2$N(CH$_3$)S(O)$_2$(phen-1,4-ylene)CH$_2$— | H |
| 351 | NH | —(CH$_2$)$_2$NH(naphth-1,4-ylene)(CH$_2$)$_2$— | H |
| 352 | NH | —(CH$_2$)$_2$NH(phen-1,4-ylene)(CH$_2$)$_2$— | H |
| 353 | NH | —(CH$_2$)$_2$NHC(O)(CH$_2$)$_5$— | H |
| 354 | NH | —(CH$_2$)$_2$NHC(O)(cis-cyclopent-1,3-ylene)- | H |
| 355 | NH | —(CH$_2$)$_2$NHC(O)(cis-cyclopent-1,3-ylene)CH$_2$— | H |
| 356 | NH | —(CH$_2$)$_2$NHC(O)(phen-1,4-ylene)(CH$_2$)$_2$— | H |
| 357 | NH | —(CH$_2$)$_2$NHC(O)(phen-1,4-ylene)CH$_2$— | H |
| 358 | NH | —(CH$_2$)$_2$NHC(O)(thien-2,5-ylene)CH$_2$— | H |
| 359 | NH | —(CH$_2$)$_2$NHC(O)(trans-cyclohex-1,4-ylene)CH$_2$— | H |
| 360 | NH | —(CH$_2$)$_2$NHC(O)NH(CH$_2$)$_5$— | H |
| 361 | NH | —(CH$_2$)$_2$NHC(O)NH(phen-1,4-ylene)(CH$_2$)$_2$— | H |
| 362 | NH | —(CH$_2$)$_2$NHC(O)NH(phen-1,4-ylene)CH$_2$— | H |
| 363 | NH | —(CH$_2$)$_2$NHC(O)NHCH$_2$(phen-1,3-ylene)CH$_2$— | H |
| 364 | NH | —(CH$_2$)$_2$NHC(O)NHCH$_2$(phen-1,4-ylene)CH$_2$— | H |
| 365 | NH | —(CH$_2$)$_2$O(phen-1,2-ylene)O(CH$_2$)$_2$— | H |
| 366 | NH | —(CH$_2$)$_2$O(phen-1,3-ylene)CH$_2$— | H |
| 367 | NH | —(CH$_2$)$_2$O(phen-1,3-ylene)O(CH$_2$)$_2$— | H |
| 368 | NH | —(CH$_2$)$_2$O(phen-1,4-ylene)C(O)(CH$_2$)$_2$— | H |
| 369 | NH | —(CH$_2$)$_2$O(phen-1,4-ylene)O(CH$_2$)$_2$— | H |
| 370 | NH | —(CH$_2$)$_2$S(O)$_2$NH(CH$_2$)$_5$— | H |
| 371 | NH | —(CH$_2$)$_3$(furan-2,5-ylene)(CH$_2$)$_3$— | H |
| 372 | NH | —(CH$_2$)$_3$(phen-1,2-ylene)NH(phen-1,4-ylene)(CH$_2$)$_2$— | H |
| 373 | NH | —(CH$_2$)$_3$(phen-1,3-ylene)(CH$_2$)$_3$— | H |
| 374 | NH | —(CH$_2$)$_3$(phen-1,3-ylene)NH(phen-1,4-ylene)(CH$_2$)$_2$— | H |
| 375 | NH | —(CH$_2$)$_3$(phen-1,4-ylene)(CH$_2$)$_2$— | H |
| 376 | NH | —(CH$_2$)$_3$(phen-1,4-ylene)(CH$_2$)$_3$— | H |
| 377 | NH | —(CH$_2$)$_3$(phen-1,4-ylene)NH(phen-1,4-ylene)(CH$_2$)$_2$— | H |
| 378 | NH | —(CH$_2$)$_3$(phen-1,4-ylene)NHC(O)(CH$_2$)$_2$— | H |
| 379 | NH | —(CH$_2$)$_3$(tetrahydrofuran-2,5-ylene)(CH$_2$)$_3$— | H |
| 380 | NH | —(CH$_2$)$_3$(thien-2,5-ylene)(CH$_2$)$_3$— | H |
| 381 | NH | —(CH$_2$)$_3$NH(phen-1,4-ylene)(CH$_2$)$_2$— | H |
| 382 | NH | —(CH$_2$)$_3$NHC(O)NH(CH$_2$)$_5$— | H |
| 383 | NH | —(CH$_2$)$_3$O(phen-1,3-ylene)CH$_2$— | H |
| 384 | NH | —(CH$_2$)$_3$O(phen-1,4-ylene)(CH$_2$)$_2$— | H |

TABLE I-continued

| Ex. | W | R⁴ | R⁶ |
|---|---|---|---|
| 385 | NH | —(CH₂)₃O(phen-1,4-ylene)CH₂— | H |
| 386 | NH | —(CH₂)₄(phen-1,4-ylene)(CH₂)₂— | H |
| 387 | NH | —(CH₂)₄NH(phen-1,4-ylene)(CH₂)₂— | H |
| 388 | NH | —(CH₂)₅NH(phen-1,4-ylene)(CH₂)₂— | H |
| 389 | NH | —(CH₂)₇— | H |
| 390 | NH | —(CH₂)₈— | H |
| 391 | NH | 1-[-(CH₂)₂C(O)](piperidin-4-yl)(CH₂)₂— | H |
| 392 | NH | 1-[-(CH₂)₂NHC(O)](piperidin-4-yl)- | H |
| 393 | NH | 1-[-(CH₂)₂NHC(O)](piperidin-4-yl)(CH₂)₂— | H |
| 394 | NH | 1-[-(CH₂)₃](piperidin-4-yl)CH₂— | H |
| 395 | NH | 1-[-(CH₂)₃O(phen-1,4-ylene)(CH₂)₂](piperidin-4-yl)CH₂— | H |
| 396 | NH | 1-[-CH₂(2-fluorophen-1,3-ylene)CH₂](piperidin-4-yl)- | H |
| 397 | NH | 1-[-CH₂(2-fluorophen-1,3-ylene)CH₂](piperidin-4-yl)(CH₂)₂— | H |
| 398 | NH | 1-[-CH₂(2-fluorophen-1,3-ylene)CH₂](piperidin-4-yl)(CH₂)₃— | H |
| 399 | NH | 1-[-CH₂(2-fluorophen-1,3-ylene)CH₂](piperidin-4-yl)CH₂— | H |
| 400 | NH | 1-[-CH₂(pyrid-2,6-ylene)CH₂](piperidin-4-yl)CH₂— | H |
| 401 | NH | 2-[-(CH₂)₂](benzimidazol-5-yl)CH₂— | H |
| 402 | NH | 2-[(S)—(—CH₂-](pyrrolidin-1-yl)C(O)(CH₂)₄— | H |
| 403 | NH | 2-[(S)—(—CH₂-](pyrrolidin-1-yl)C(O)(phen-1,4-ylene)CH₂— | H |
| 404 | NH | 4-[-(CH₂)₂-](piperidin-1-yl)(phen-1,4-ylene)(CH₂)₂— | H |
| 405 | NH | 4-[-(CH₂)₂](piperidin-1-yl)C(O)(CH₂)₂— | H |
| 406 | NH | 4-[-(CH₂)₂](piperidin-1-yl)C(O)(CH₂)₃— | H |
| 407 | NH | 4-[-(CH₂)₂](piperidin-1-yl)C(O)(CH₂)₄— | H |
| 408 | NH | 4-[-(CH₂)₂](piperidin-1-yl)C(O)(CH₂)₅— | H |
| 409 | NH | 4-[-(CH₂)₂](piperidin-1-yl)C(O)(fur-2,5-ylene)CH₂— | H |
| 410 | NH | 4-[-(CH₂)₂](piperidin-1-yl)C(O)(phen-1,4-ylene)CH₂— | H |
| 411 | NH | 4-[-(CH₂)₂](piperidin-1-yl)C(O)(thien-2,5-ylene)CH₂— | H |
| 412 | NH | 4-[-(CH₂)₂](piperidin-1-yl)C(O)CH₂O(phen-1,2-ylene)CH₂— | H |
| 413 | NH | 4-[-(CH₂)₂](piperidin-1-yl)C(O)CH₂O(phen-1,3-ylene)CH₂— | H |
| 414 | NH | 4-[-(CH₂)₂](piperidin-1-yl)C(O)CH₂O(phen-1,4-ylene)CH₂— | H |
| 415 | NH | 4-[-(CH₂)₂](piperidin-1-yl)C(O)NH(phen-1,4-ylene)(CH₂)₂— | H |
| 416 | NH | 4-[-CH₂-](piperidin-1-yl)C(O)(phen-1,4-ylene)CH₂— | H |
| 417 | NH | 5-[-(CH₂)₂NHC(O)](pyrid-2-yl)CH₂— | H |
| 418 | NH | —CH₂(2-fluorophen-1,3-ylene)CH₂— | H |
| 419 | NH | —CH₂(phen-1,2-ylene)NH(phen-1,4-ylene)(CH₂)₂— | H |
| 420 | NH | —CH₂(phen-1,2-ylene)O(phen-1,2-ylene)CH₂— | H |
| 421 | NH | —CH₂(phen-1,3-ylene)NH(phen-1,4-ylene)(CH₂)₂— | H |
| 422 | NH | —CH₂(phen-1,4-ylene)NH(phen-1,4-ylene)CH₂— | H |
| 423 | NH | —CH₂CH(OH)CH₂NH(phen-1,4-ylene)(CH₂)₂— | H |
| 424 | NH | —(CH₂)₉— | OH |
| 425 | NH | —(CH₂)₂C(O)NH(phen-1,4-ylene)CH₂— | OH |
| 426 | NH | —(CH₂)₂C(O)NH(phen-1,4-ylene)CH₂CH₂— | OH |
| 427 | NH | —(CH₂)₂(phen-1,3-ylene)NH(phen-1,4-ylene)(CH₂)₂— | OH |
| 428 | NH | —(CH₂)₂(phen-1,4-ylene)(CH₂)₂— | OH |
| 429 | NH | —(CH₂)₂(phen-1,4-ylene)NHC(O)(fur-2,5-ylene)CH₂— | OH |
| 430 | NH | —(CH₂)₂(phen-1,4-ylene)NHC(O)(phen-1,3-ylene)CH₂— | OH |
| 431 | NH | —(CH₂)₂(phen-1,4-ylene)NHC(O)(phen-1,4-ylene)CH₂— | OH |
| 432 | NH | —(CH₂)₂(phen-1,4-ylene)NHC(O)(thien-2,5-ylene)CH₂— | OH |
| 433 | NH | —(CH₂)₂(phen-1,4-ylene)NHC(O)CH₂O(phen-1,2-ylene)CH₂— | OH |
| 434 | NH | —(CH₂)₂(phen-1,4-ylene)NHC(O)CH₂O(phen-1,3-ylene)CH₂— | OH |
| 435 | NH | —(CH₂)₂(phen-1,4-ylene)NHC(O)CH₂O(phen-1,4-ylene)CH₂— | OH |
| 436 | NH | —(CH₂)₂-(trans-cyclohex-1,4-ylene)NH(phen-1,4-ylene)(CH₂)₂— | OH |
| 437 | NH | —(CH₂)₂-(trans-cyclohex-1,4-ylene)NHC(O)(CH₂)₂— | OH |
| 438 | NH | —(CH₂)₂-(trans-cyclohex-1,4-ylene)NHC(O)(CH₂)₄— | OH |
| 439 | NH | —(CH₂)₂-(trans-cyclohex-1,4-ylene)NHC(O)(CH₂)₅— | OH |
| 440 | NH | —(CH₂)₂(trans-cyclohex-1,4-ylene)NHC(O)(fur-2,5-ylene)CH₂— | OH |
| 441 | NH | —(CH₂)₂(trans-cyclohex-1,4-ylene)NHC(O)(phen-1,3-ylene)CH₂— | OH |
| 442 | NH | —(CH₂)₂(trans-cyclohex-1,4-ylene)NHC(O)(phen-1,4-ylene)CH₂— | OH |
| 443 | NH | —(CH₂)₂(trans-cyclohex-1,4-ylene)NHC(O)(thien-2,5-ylene)CH₂— | OH |
| 444 | NH | —(CH₂)₂(trans-cyclohex-1,4-ylene)NHC(O)CH₂O(phen-1,2-ylene)CH₂— | OH |
| 445 | NH | —(CH₂)₂(trans-cyclohex-1,4-ylene)NHC(O)CH₂O(phen-1,3-ylene)CH₂— | OH |
| 446 | NH | —(CH₂)₂(trans-cyclohex-1,4-ylene)NHC(O)CH₂O(phen-1,4-ylene)CH₂— | OH |
| 447 | NH | —(CH₂)₂C(O)N(CH₂CH₃)(phen-1,4-ylene)CH₂— | OH |
| 448 | NH | —(CH₂)₂C(O)NH(2-(CF₃O-)phen-1,4-ylene)CH₂— | OH |
| 449 | NH | —(CH₂)₂C(O)NH(2,3,5,6-tetrafluorophen-1,4-ylene)CH₂— | OH |
| 450 | NH | —(CH₂)₂C(O)NH(2,5-difluorophen-1,4-ylene)CH₂— | OH |
| 451 | NH | —(CH₂)₂C(O)NH(2,6-dichlorophen-1,4-ylene)CH₂— | OH |
| 452 | NH | —(CH₂)₂C(O)NH(2,6-diiodophen-1,4-ylene)CH₂— | OH |
| 453 | NH | —(CH₂)₂C(O)NH(2-bromophen-1,4-ylene)CH₂— | OH |
| 454 | NH | —(CH₂)₂C(O)NH(2-chloro-5-methoxyphen-1,4-ylene)CH₂— | OH |
| 455 | NH | —(CH₂)₂C(O)NH(2-chloro-6-methylphen-1,4-ylene)CH₂— | OH |
| 456 | NH | —(CH₂)₂C(O)NH(2-chlorophen-1,4-ylene)CH₂— | OH |
| 457 | NH | —(CH₂)₂C(O)NH(2-fluorophen-1,4-ylene)CH₂— | OH |
| 458 | NH | —(CH₂)₂C(O)NH(2-iodophen-1,4-ylene)CH₂— | OH |
| 459 | NH | —(CH₂)₂C(O)NH(2-methoxyphen-1,4-ylene)CH₂— | OH |

TABLE I-continued

| Ex. | W | R⁴ | R⁶ |
|---|---|---|---|
| 460 | NH | —(CH₂)₂C(O)NH(2-methylphen-1,4-ylene)CH₂— | OH |
| 461 | NH | —(CH₂)₂C(O)NH(3-chlorophen-1,4-ylene)CH₂— | OH |
| 462 | NH | —(CH₂)₂C(O)NH(4-chlorophen-1,3-ylene)CH₂— | OH |
| 463 | NH | —(CH₂)₂C(O)NH(4-methylphen-1,3-ylene)CH₂— | OH |
| 464 | NH | —(CH₂)₂C(O)NH(6-chlorophen-1,3-ylene)CH₂— | OH |
| 465 | NH | —(CH₂)₂C(O)NH(CH₂)₅— | OH |
| 466 | NH | —(CH₂)₂C(O)NH(CH₂)₆— | OH |
| 467 | NH | —(CH₂)₂C(O)NH(cis-cyclohex-1,4-ylene)CH₂— | OH |
| 468 | NH | —(CH₂)₂C(O)NH(phen-1,4-ylene)(CH₂)₂NHC(O)CH₂— | OH |
| 469 | NH | —(CH₂)₂C(O)NH(phen-1,4-ylene)C*H(CH₃)-((S)-isomer) | OH |
| 470 | NH | —(CH₂)₂C(O)NH(phen-1,4-ylene)C*H(CH₃)-((R)-isomer) | OH |
| 471 | NH | —(CH₂)₂C(O)NH(phen-1,4-ylene)CH(CH₃)CH₂— | OH |
| 472 | NH | —(CH₂)₂C(O)NH(phen-1,4-ylene)CH₂NHC(O)CH₂— | OH |
| 473 | NH | —(CH₂)₂C(O)NH(trans-cyclohex-1,4-ylene)CH₂— | OH |
| 474 | NH | —(CH₂)₂C(O)NHCH₂(cyclohex-1,3-ylene)CH₂— | OH |
| 475 | NH | —(CH₂)₂C(O)NHCH₂(phen-1,3-ylene)(CH₂)₂— | OH |
| 476 | NH | —(CH₂)₂C(O)NHCH₂(phen-1,3-ylene)CH₂— | OH |
| 477 | NH | —(CH₂)₂C(O)NHCH₂(phen-1,4-ylene)CH₂— | OH |
| 478 | NH | —(CH₂)₂C(O)NHCH₂(pyrid-2,6-ylene)CH₂— | OH |
| 479 | NH | —(CH₂)₂C(O)NHCH₂(trans-cyclohex-1,4-ylene)CH₂— | OH |
| 480 | NH | —(CH₂)₂N(CH₃)(CH₂)₂(cis-cyclohex-1,4-ylene)- | OH |
| 481 | NH | —(CH₂)₂N(CH₃)C(O)(3-nitrophen-1,4-ylene)CH₂— | OH |
| 482 | NH | —(CH₂)₂N(CH₃)C(O)(CH₂)₅— | OH |
| 483 | NH | —(CH₂)₂N(CH₃)C(O)(fur-2,5-ylene)CH₂— | OH |
| 484 | NH | —(CH₂)₂N(CH₃)C(O)(phen-1,3-ylene)CH₂— | OH |
| 485 | NH | —(CH₂)₂N(CH₃)C(O)(thien-2,5-ylene)CH₂— | OH |
| 486 | NH | —(CH₂)₂N(CH₃)C(O)(trans-cyclohex-1,4-ylene)- | OH |
| 487 | NH | —(CH₂)₂N(CH₃)C(O)(trans-cyclohex-1,4-ylene)CH₂— | OH |
| 488 | NH | —(CH₂)₂N(CH₃)C(O)CH₂O(phen-1,3-ylene)CH₂— | OH |
| 489 | NH | —(CH₂)₂N(CH₃)C(O)CH₂O(phen-1,4-ylene)CH₂— | OH |
| 490 | NH | —(CH₂)₂N(CH₃)C(O)NH(phen-1,4-ylene)(CH₂)₂— | OH |
| 491 | NH | —(CH₂)₂N(CH₃)S(O)₂(phen-1,4-ylene)CH₂— | OH |
| 492 | NH | —(CH₂)₂NH(naphth-1,4-ylene)(CH₂)₂— | OH |
| 493 | NH | —(CH₂)₂NH(phen-1,4-ylene)(CH₂)₂— | OH |
| 494 | NH | —(CH₂)₂NHC(O)(CH₂)₅— | OH |
| 495 | NH | —(CH₂)₂NHC(O)(cis-cyclopent-1,3-ylene)- | OH |
| 496 | NH | —(CH₂)₂NHC(O)(cis-cyclopent-1,3-ylene)CH₂— | OH |
| 497 | NH | —(CH₂)₂NHC(O)(phen-1,4-ylene)(CH₂)₂— | OH |
| 498 | NH | —(CH₂)₂NHC(O)(phen-1,4-ylene)CH₂— | OH |
| 499 | NH | —(CH₂)₂NHC(O)(thien-2,5-ylene)CH₂— | OH |
| 500 | NH | —(CH₂)₂NHC(O)(trans-cyclohex-1,4-ylene)CH₂— | OH |
| 501 | NH | —(CH₂)₂NHC(O)NH(CH₂)₅— | OH |
| 502 | NH | —(CH₂)₂NHC(O)NH(phen-1,4-ylene)(CH₂)₂— | OH |
| 503 | NH | —(CH₂)₂NHC(O)NH(phen-1,4-ylene)CH₂— | OH |
| 504 | NH | —(CH₂)₂NHC(O)NHCH₂(phen-1,3-ylene)CH₂— | OH |
| 505 | NH | —(CH₂)₂NHC(O)NHCH₂(phen-1,4-ylene)CH₂— | OH |
| 506 | NH | —(CH₂)₂O(phen-1,2-ylene)O(CH₂)₂— | OH |
| 507 | NH | —(CH₂)₂O(phen-1,3-ylene)CH₂— | OH |
| 508 | NH | —(CH₂)₂O(phen-1,3-ylene)O(CH₂)₂— | OH |
| 509 | NH | —(CH₂)₂O(phen-1,4-ylene)C(O)(CH₂)₂— | OH |
| 510 | NH | —(CH₂)₂O(phen-1,4-ylene)O(CH₂)₂— | OH |
| 511 | NH | —(CH₂)₂S(O)₂NH(CH₂)₅— | OH |
| 512 | NH | —(CH₂)₃(furan-2,5-ylene)(CH₂)₃— | OH |
| 513 | NH | —(CH₂)₃(phen-1,2-ylene)NH(phen-1,4-ylene)(CH₂)₂— | OH |
| 514 | NH | —(CH₂)₃(phen-1,3-ylene)(CH₂)₃— | OH |
| 515 | NH | —(CH₂)₃(phen-1,3-ylene)NH(phen-1,4-ylene)(CH₂)₂— | OH |
| 516 | NH | —(CH₂)₃(phen-1,4-ylene)(CH₂)₂— | OH |
| 517 | NH | —(CH₂)₃(phen-1,4-ylene)(CH₂)₃— | OH |
| 518 | NH | —(CH₂)₃(phen-1,4-ylene)NH(phen-1,4-ylene)(CH₂)₂— | OH |
| 519 | NH | —(CH₂)₃(phen-1,4-ylene)NHC(O)(CH₂)₂— | OH |
| 520 | NH | —(CH₂)₃(tetrahydrofuran-2,5-ylene)(CH₂)₃— | OH |
| 521 | NH | —(CH₂)₃(thien-2,5-ylene)(CH₂)₃— | OH |
| 522 | NH | —(CH₂)₃NH(phen-1,4-ylene)(CH₂)₂— | OH |
| 523 | NH | —(CH₂)₃NHC(O)NH(CH₂)₅— | OH |
| 524 | NH | —(CH₂)₃O(phen-1,3-ylene)CH₂— | OH |
| 525 | NH | —(CH₂)₃O(phen-1,4-ylene)(CH₂)₂— | OH |
| 526 | NH | —(CH₂)₃O(phen-1,4-ylene)CH₂— | OH |
| 527 | NH | —(CH₂)₄(phen-1,4-ylene)(CH₂)₂— | OH |
| 528 | NH | —(CH₂)₄NH(phen-1,4-ylene)(CH₂)₂— | OH |
| 529 | NH | —(CH₂)₅NH(phen-1,4-ylene)(CH₂)₂— | OH |
| 530 | NH | —(CH₂)₇— | OH |
| 531 | NH | —(CH₂)₈— | OH |
| 532 | NH | 1-[-(CH₂)₂C(O)](piperidin-4-yl)(CH₂)₂— | OH |
| 533 | NH | 1-[-(CH₂)₂NHC(O)](piperidin-4-yl)- | OH |
| 534 | NH | 1-[-(CH₂)₂NHC(O)](piperidin-4-yl)(CH₂)₂— | OH |
| 535 | NH | 1-[-(CH₂)₃](piperidin-4-yl)CH₂— | OH |
| 536 | NH | 1-[-(CH₂)₃O(phen-1,4-ylene)(CH₂)₂](piperidin-4-yl)CH₂— | OH |
| 537 | NH | 1-[-CH₂(2-fluorophen-1,3-ylene)CH₂](piperidin-4-yl)- | OH |

TABLE I-continued

| Ex. | W | R⁴ | R⁶ |
|---|---|---|---|
| 538 | NH | 1-[-CH₂(2-fluorophen-1,3-ylene)CH₂](piperidin-4-yl)(CH₂)₂— | OH |
| 539 | NH | 1-[-CH₂(2-fluorophen-1,3-ylene)CH₂](piperidin-4-yl)(CH₂)₃— | OH |
| 540 | NH | 1-[-CH₂(2-fluorophen-1,3-ylene)CH₂](piperidin-4-yl)CH₂— | OH |
| 541 | NH | 1-[-CH₂(pyrid-2,6-ylene)CH₂](piperidin-4-yl)CH₂— | OH |
| 542 | NH | 2-[-(CH₂)₂](benzimidazol-5-yl)CH₂— | OH |
| 543 | NH | 2-[(S)—(—CH₂—](pyrrolidin-1-yl)C(O)(CH₂)₄— | OH |
| 544 | NH | 2-[(S)—(—CH₂—](pyrrolidin-1-yl)C(O)(phen-1,4-ylene)CH₂— | OH |
| 545 | NH | 4-[-(CH₂)₂—](piperidin-1-yl)(phen-1,4-ylene)(CH₂)₂— | OH |
| 546 | NH | 4-[-(CH₂)₂](piperidin-1-yl)C(O)(CH₂)₂— | OH |
| 547 | NH | 4-[-(CH₂)₂](piperidin-1-yl)C(O)(CH₂)₃— | OH |
| 548 | NH | 4-[-(CH₂)₂](piperidin-1-yl)C(O)(CH₂)₄— | OH |
| 549 | NH | 4-[-(CH₂)₂](piperidin-1-yl)C(O)(CH₂)₅— | OH |
| 550 | NH | 4-[-(CH₂)₂](piperidin-1-yl)C(O)(fur-2,5-ylene)CH₂— | OH |
| 551 | NH | 4-[-(CH₂)₂](piperidin-1-yl)C(O)(phen-1,4-ylene)CH₂— | OH |
| 552 | NH | 4-[-(CH₂)₂](piperidin-1-yl)C(O)(thien-2,5-ylene)CH₂— | OH |
| 553 | NH | 4-[-(CH₂)₂](piperidin-1-yl)C(O)CH₂O(phen-1,2-ylene)CH₂— | OH |
| 554 | NH | 4-[-(CH₂)₂](piperidin-1-yl)C(O)CH₂O(phen-1,3-ylene)CH₂— | OH |
| 555 | NH | 4-[-(CH₂)₂](piperidin-1-yl)C(O)CH₂O(phen-1,4-ylene)CH₂— | OH |
| 556 | NH | 4-[-(CH₂)₂](piperidin-1-yl)C(O)NH(phen-1,4-ylene)(CH₂)₂— | OH |
| 557 | NH | 4-[-CH₂—](piperidin-1-yl)C(O)(phen-1,4-ylene)CH₂— | OH |
| 558 | NH | 5-[-(CH₂)₂NHC(O)](pyrid-2-yl)CH₂— | OH |
| 559 | NH | —CH₂(2-fluorophen-1,3-ylene)CH₂— | OH |
| 560 | NH | —CH₂(phen-1,2-ylene)NH(phen-1,4-ylene)(CH₂)₂— | OH |
| 561 | NH | —CH₂(phen-1,2-ylene)O(phen-1,2-ylene)CH₂— | OH |
| 562 | NH | —CH₂(phen-1,3-ylene)NH(phen-1,4-ylene)(CH₂)₂— | OH |
| 563 | NH | —CH₂(phen-1,4-ylene)NH(phen-1,4-ylene)CH₂— | OH |
| 564 | NH | —CH₂CH(OH)CH₂NH(phen-1,4-ylene)(CH₂)₂— | OH |

Another group of representative compounds of this invention are compounds of formula If:

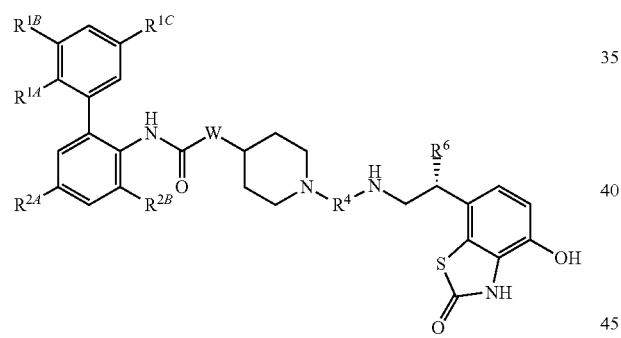

If wherein W, $R^{1A}$, $R^{1B}$, $R^{1C}$, $R^{2A}$, $R^{2B}$, $R^4$ and $R^6$ are as defined in Table II; or a pharmaceutically acceptable salt or solvate thereof.

TABLE II

| Ex. | W | R¹ᴬ | R¹ᴮ | R¹ᶜ | R²ᴬ | R²ᴮ | R⁴ | R⁶ |
|---|---|---|---|---|---|---|---|---|
| 565 | O | H | H | H | Br | H | —(CH₂)₉— | H |
| 566 | O | F | H | H | H | H | —(CH₂)₉— | H |
| 567 | O | H | Cl | H | F | F | —(CH₂)₉— | H |
| 568 | O | H | Cl | Cl | F | F | —(CH₂)₉— | H |
| 569 | O | H | H | H | F | F | —(CH₂)₉— | H |
| 570 | O | H | H | H | Br | H | —(CH₂)₂C(O)NH(phen-1,4-ylene)CH₂— | H |
| 571 | O | F | H | H | H | H | —(CH₂)₂C(O)NH(phen-1,4-ylene)CH₂— | H |
| 572 | O | H | Cl | H | F | F | —(CH₂)₂C(O)NH(phen-1,4-ylene)CH₂— | H |
| 573 | O | H | Cl | Cl | F | F | —(CH₂)₂C(O)NH(phen-1,4-ylene)CH₂— | H |
| 574 | O | H | H | H | F | F | —(CH₂)₂C(O)NH(phen-1,4-ylene)CH₂— | H |

TABLE II-continued

| Ex. | W | $R^{1A}$ | $R^{1B}$ | $R^{1C}$ | $R^{2A}$ | $R^{2B}$ | $R^4$ | $R^6$ |
|---|---|---|---|---|---|---|---|---|
| 575 | O | H | H | H | Br | H | —(CH$_2$)$_9$— | OH |
| 576 | O | F | H | H | H | H | —(CH$_2$)$_9$— | OH |
| 577 | O | H | Cl | H | F | F | —(CH$_2$)$_9$— | OH |
| 578 | O | H | Cl | Cl | F | F | —(CH$_2$)$_9$— | OH |
| 579 | O | H | H | H | F | F | —(CH$_2$)$_9$— | OH |
| 580 | O | H | H | H | Br | H | —(CH$_2$)$_2$C(O)NH(phen-1,4-ylene)CH$_2$— | OH |
| 581 | O | F | H | H | H | H | —(CH$_2$)$_2$C(O)NH(phen-1,4-ylene)CH$_2$— | OH |
| 582 | O | H | Cl | H | F | F | —(CH$_2$)$_2$C(O)NH(phen-1,4-ylene)CH$_2$— | OH |
| 583 | O | H | Cl | Cl | F | F | —(CH$_2$)$_2$C(O)NH(phen-1,4-ylene)CH$_2$— | OH |
| 584 | O | H | H | H | F | F | —(CH$_2$)$_2$C(O)NH(phen-1,4-ylene)CH$_2$— | OH |

Definitions

When describing the compounds, compositions, methods and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like. The term "alkenylene" means a divalent alkenyl group.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like. The term "alkynylene" means a divalent alkynyl group.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like. The term "arylene" means a divalent aryl group.

The term "azacycloalkyl" means a monovalent heterocyclic ring containing one nitrogen atom, i.e., a cycloalkyl group in which one carbon atom has been replaced with a nitrogen atom. Unless otherwise defined, such azacycloalkyl groups typically contain from 2 to 9 carbon atoms. Representative examples of an azacycloalkyl group are pyrrolidinyl and piperidinyl groups. The term "azacycloalkylene" means a divalent azacycloalkyl group. Representative examples of an azacycloalkylene group are pyrrolidinylene and piperidinylene groups.

The term "azabicycloalkyl" means a monovalent heterobicyclic ring containing one nitrogen atom, i.e., a bicycloalkyl group in which one carbon atom has been replaced with a nitrogen atom. Unless otherwise defined, such azabicycloalkyl groups typically contain from 5 to 10 carbon atoms. Representative azabicycloalkyl groups include 2-azabicyclo[2.2.1]heptyl, 7-azabicyclo[2.2.1]heptyl, 1-azabicyclo[2.2.2]octyl, 2-azabicyclo[2.2.2]octyl, 9-azabicyclo[4.2.1]nonyl, 3-azabicyclo[3.3.2]decyl, 9-azabicyclo[3.3.2]decyl and the like. The term "azabicycloalkylene" means a divalent azabicycloakyl group.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like. The term "cycloalkylene" means a divalent cycloalkyl group.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. The term "heteroarylene" means a divalent heteroaryl group.

The term "heterocyclyl" or "heterocyclic" means a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom. The term "heterocyclene" means a divalent heterocyclyl or heterocyclic group. which is substituted and optionally substituted as defined herein.

The term "divalent hydrocarbon group" means a divalent hydrocarbon group which is composed primarily of carbon and hydrogen atoms and which optionally contains one or more heteroatoms. Such divalent hydrocarbon groups may be branched or unbranched, saturated or unsaturated, acyclic or cyclic, aliphatic or aromatic, or combinations thereof.

The divalent hydrocarbon group can optionally contain heteroatoms incorporated into the hydrocarbon chain or as substituents attached to the hydrocarbon chain.

When a specific number of carbon atoms is intended for a particular term used herein, the number of carbon atoms is shown in parentheses preceding the term. For example, the term "(1-4C)alkyl" means an alkyl group having from 1 to 4 carbon atoms.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, naphthalene-1,5-disulfonic, phosphoric, sulfuric and tartaric acids.

The term "salt thereof" means a compound formed when the hydrogen of an acid is replaced by a cation, such as a metal cation or an organic cation and the like. Preferably, the salt is a pharmaceutically acceptable salt, although this is not required for salts of intermediate compounds that are not intended for administration to a patient.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

It will be appreciated that the term "or a pharmaceutically acceptable salt or solvate or stereoisomer thereof" is intended to include all permutations of salts, solvates and stereoisomers, such as a solvate of a pharmaceutically acceptable salt of a stereoisomer of a compound of this invention.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:
(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected derivatives thereof" means a derivative of the specified compound in which one or more functional groups of the compound are protected from undesired reactions with a protecting or blocking group. Functional groups that may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" means a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluoroenylmethyl (Fm), trimethylsilyl (TMS), tert-butyldimethylsilyl (TBS), diphenylmethyl (benzhydryl, DPM) and the like.

The term "hydroxyl-protecting group" means a protecting group suitable for preventing undesirable reactions at a hydroxyl group. Representative hydroxyl-protecting groups include, but are not limited to, silyl groups including tri(1-6C)alkylsilyl groups, such as trimethylsilyl (TMS), triethylsilyl (TES), tert-butyldimethylsilyl (TBS) and the like; esters (acyl groups) including (1-6C)alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group, such as prop-2-ylidine, formed, for example, by reaction with a ketone, such as acetone.

General Synthetic Procedures

The compounds of this invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one of ordinary skill in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein.

By way of illustration, the compounds of this invention can be prepared by a process comprising:

(a) reacting a compound of formula 1:

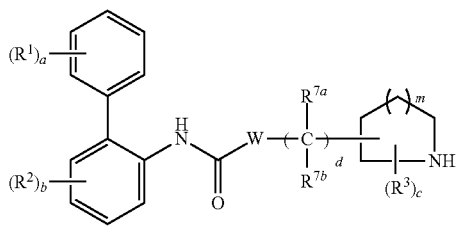

1 or a salt thereof; with a compound of formula 2:

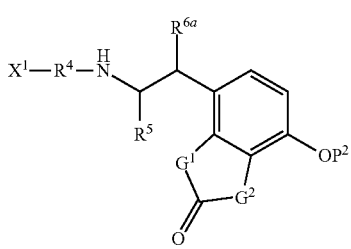

2 wherein $X^1$ represents a leaving group, $R^{6a}$ represents hydrogen or $OP^1$, and $P^1$ and $P^2$ each independently represent a hydrogen atom or a hydroxyl-protecting group;

(b) reacting a compound of formula 3:

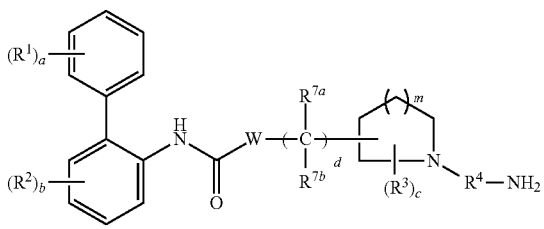

3 or salt thereof; with a compound of formula 4:

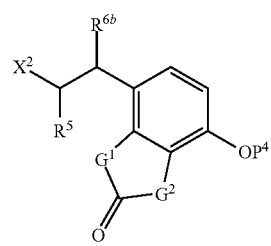

4 wherein $X^2$ represents a leaving group, $R^{6b}$ represents hydrogen or $OP^3$, and $P^3$ and $P^4$ each independently represent a hydrogen atom or a hydroxyl-protecting group;

(c) coupling a compound of formula 5:

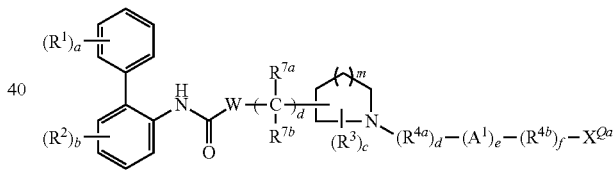

5 with a compound of formula 6:

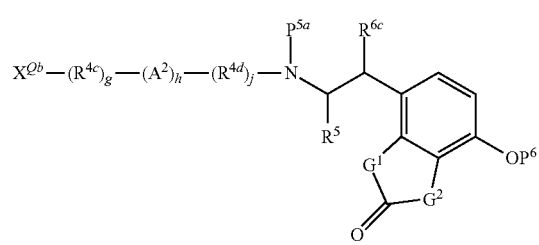

6 wherein $X^{Qa}$ and $X^{Qb}$ each independently represent functional groups that couple to form a group Q, $P^{5a}$ represents a hydrogen atom or an amino-protecting group, $R^{6c}$ represents hydrogen or $OP^{5b}$, and $P^{5b}$ and $P^6$ each independently represent a hydrogen atom or a hydroxyl-protecting group;

(d) for a compound of formula I wherein $R^5$ represents a hydrogen atom, reacting a compound of formula 3 with a compound of formula 7a or 7b:

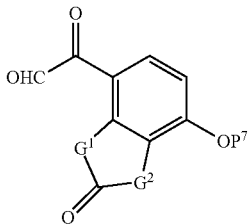

7a

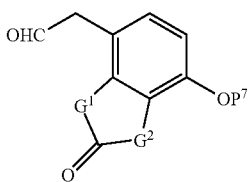

7b or a hydrate thereof (e.g., a glyoxal), in the presence of a reducing agent, wherein $P^7$ represents a hydrogen atom or a hydroxyl-protecting group;

(e) reacting a compound of formula 1 with a compound of formula 8:

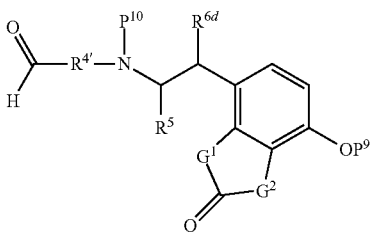

8 or a hydrate thereof, in the presence of a reducing agent, wherein $R^{6d}$ represents hydrogen or $OP^8$, $P^8$ and $P^9$ each independently represent a hydrogen atom or a hydroxyl-protecting group, $P^{10}$ represents a hydrogen atom or an amino-protecting group, and $R^{4'}$ represents a residue that, together with the carbon to which it is attached, affords a group $R^4$ upon completion of the reaction;

(f) reacting a compound of formula 9:

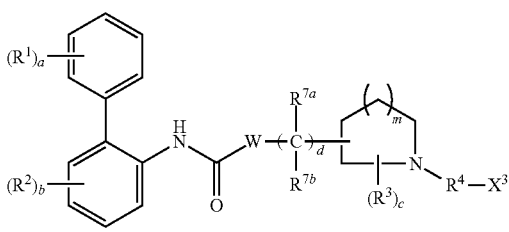

9 wherein $X^3$ represents a leaving group, with a compound of formula 10:

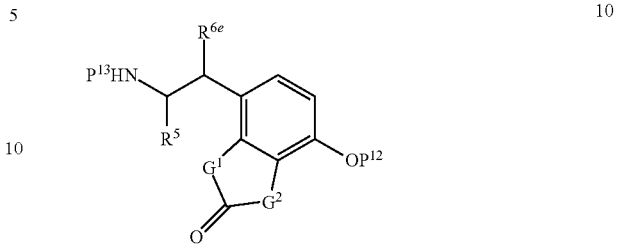

10 wherein $R^{6e}$ represents hydrogen or $OP^{11}$, $P^{11}$ and $P^{12}$ each independently represent a hydrogen atom or a hydroxyl-protecting group, and $P^{13}$ represents a hydrogen atom or an amino-protecting group; or (g) reacting a compound of formula 11:

11 or a hydrate thereof; wherein $R^{4'}$ represents a residue that, together with the carbon to which it is attached, affords a group $R^4$ upon completion of the reaction; with a compound of formula 10 in the presence of a reducing agent; and then removing any protecting group $P^1$, $P^2$, $P^3$, $P^4$, $P^{5a}$, $P^{5b}$, $P^6$, $P^7$, $P^8$, $P^9$, $P^{10}$, $P^{11}$, $P^{12}$ or $P^{13}$ to provide a compound of formula I; and optionally, forming a pharmaceutically acceptable salt thereof.

Generally, if a salt of one of the starting materials is used in the processes described above, such as an acid addition salt, the salt is typically neutralized before or during the reaction process. This neutralization reaction is typically accomplished by contacting the salt with one molar equivalent of a base for each molar equivalent of acid addition salt.

In process (a), i.e., the reaction between the compounds of formula 1 and 2, the leaving group represented by $X^1$ can be, for example, halo, such as chloro, bromo or iodo, or a sulfonic ester group, such as mesylate or tosylate. The groups $P^1$ and $P^2$ can be, for example, trimethylsilyl and benzyl or methyl, respectively. This reaction is typically conducted in an inert diluent, such as acetonitrile, in the presence of a base. For example, this reaction can be conducted in the presence of a tertiary amine, such as diisopropylethylamine. Generally, this reaction is conducted at a temperature in the range of from 0° C. to 100° C. until the reaction is substantially complete. The reaction product is then isolated using conventional procedures, such as extraction, recrystallization, chromatography and the like.

Compounds of formula 1 are generally known in the art or can be prepared from commercially available starting materials and reagents using well-known procedures. For example, compounds of formula 1 can be prepared by deprotecting a compound of formula 12:

12

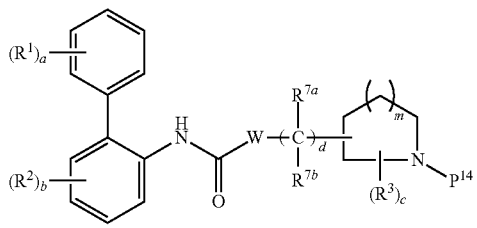

wherein $P^{14}$ represents an amino-protecting group, such as a benzyl group. By way of illustration, a benzyl group can be readily removed by reduction using, for example, hydrogen or ammonium formate and a group VIII metal catalyst, such as palladium on carbon. When W represents $NW^a$, the hydrogenation reaction is conveniently performed using Pearlman's catalyst (i.e., $Pd(OH)_2$).

Compounds of formula 12 can be prepared by reacting an isocyanate compound of formula 13:

13

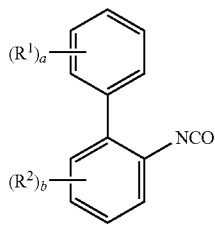

with a compound of formula 14:

14

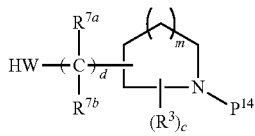

Compounds of formula 2 can be prepared by various procedures described herein or by procedures that are well-known to those skilled in the art. In this regard, the preparation of related compounds is described in U.S. Pat. Nos. 5,648,370; 5,763,465; 5,846,989; 5,929,100; 5,973,167; 5,977,384; 6,008,365; and 6,080,869; in Internation Patent Publication Nos. WO 92/08708; WO 93/23385; WO 93/24473; WO 97/10227; WO 97/23470; WO 99/09018; WO 00/50413 and WO 2004/016601 A1; and in Weistock et al, *J. Med. Chem.* 1987, 30, 1166-1176. By way of illustration, the hydroxyl group of a compound of formula 23 below, can be readily converted into a leaving group using well-known reagents and procedures. For example, a hydroxyl group can be converted into a halo group using an inorganic acid halide, such as thionyl chloride, phosphorous trichloride, phosphorous tribromide, phosphorous oxychloride and the like, or a halogen acid, such a hydrogen bromide.

In process (b), i.e., the reaction of a compound of formula 3 with a compound of formula 4, the leaving represented by $X^2$ can be, for example, halo, such as chloro, bromo or iodo, or a sulfonic ester group, such as mesylate or tosylate. The groups $P^3$ and $P^4$ can be, for example, tert-butyldimethylsilyl and benzyl or methyl, respectively. This reaction is typically conducted in the presence of a base, such as sodium bicarbonate, and an alkali metal iodide, such as sodium iodide. Generally, this reaction is conducted in an inert diluent, such as tetrahydrofuran, at a temperature ranging from 25° C. to 100° C. until the reaction is substantially complete. The reaction product is then isolated using conventional procedures, such as extraction, recrystallization, chromatography and the like.

Compounds of formula 3 can be prepared by deprotecting a compound of formula 15:

15

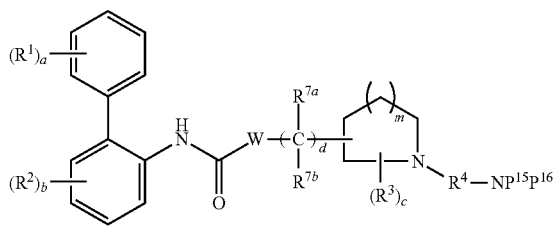

wherein one or both of $P^{15}$ and $P^{16}$ independently represents a protecting group, such as tert-butoxycarbonyl, and any remainder represents a hydrogen atom. For example, a tert-butoxycarbonyl group can be removed by treating the protected compound with trifluoroacetic acid.

Compounds of formula 15 can be prepared by reacting a compound of formula 1 with a compound of formula 16:

$$X^3-R^4-NP^{15}P^{16} \qquad 16$$

wherein $X^3$ represents a leaving group such as halo, such as chloro, bromo or iodo, or sulfonic ester group, such as mesylate or tosylate. This reaction is typically conducted by contacting a compound of formula 1 with a compound of formula 16 in an inert diluent, such as acetonitrile, DMF or mixtures thereof, at a temperature ranging from about 0° C. to about 100° C. until the reaction is substantially complete.

Alternatively, compounds of formula 3 can be obtained by reductive amination of a compound of formula 11. The reductive amination can be performed by reacting the compound of formula 11 with, for example, benzylamine and hydrogen in the presence of palladium on carbon.

Compounds of formula 11 may be prepared by oxidizing the corresponding alcohol of formula 17:

17

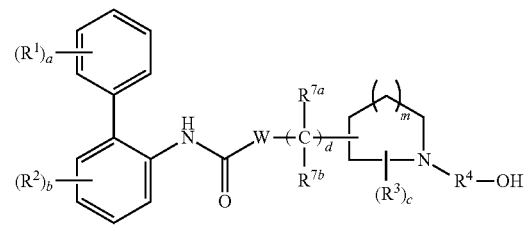

using a suitable oxidizing agent, such as sulfur trioxide pyridine complex and dimethyl sulfoxide. This oxidation reaction is typically conducted in an inert diluent, such as dichloromethane, the presence of a tertiary amine, such as diisopropylethylamine, at a temperature ranging from about −20° C. to about 25° C.

Compounds of formula 17 can be prepared by reacting a compound of formula 1 with a compound of formula 18:

$$X^4-R^4-OH \qquad 18$$

wherein $X^4$ represents a leaving group such as halo, such as chloro, bromo or iodo, or a sulfonic ester group, such as mesylate or tosylate.

Compounds of formula 4 in which $R^{6b}$ represents $OP^3$ can be prepared by reacting a compound of formula 19:

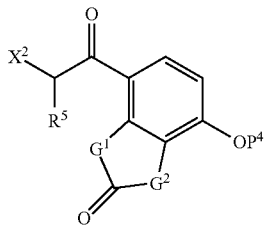

19 with a reducing agent, such as borane, and then protecting the resulting hydroxyl group if necessary. If desired, such a reduction can be performed in the presence of a chiral catalyst to provide compounds of formula 4 in chiral form. For example, compounds of formula 19 can be reduced in the presence of a chiral catalyst formed from (R)-(+)-α,α-diphenyl-2-pyrrolidinemethanol and trimethylboroxine; or alternatively, from (S)-(–)-α,α-diphenyl-2-pyrrolidinemethanol and trimethylboroxine. The resulting hydroxyl group can then be protected with a hydroxyl-protecting group, $P^3$, by reaction with, for example, tert-butyldimethylsilyl trifluoromethanesulfonate.

Compounds of formula 19 in which $X^2$ represents a bromine atom can be prepared by reacting a compound of formula 20:

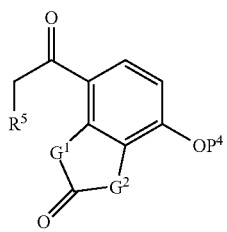

20 with bromine in the presence of a Lewis acid, such as boron trifluoride diethyl etherate. Compounds of formula 20 are well-known in the art or can be prepared by well-known procedures using commercially available starting materials and reagents.

Referring to process (c), i.e., the reaction of a compound of formula 5 with a compound of formula 6, it will be appreciated that the groups $X^{Qa}$ and $X^{Qb}$ should be selected so as to afford the desired group Q upon completion of the reaction. For example, when the desired group Q is an amide group, i.e., —N($Q^a$)C(O)— or —C(O)N($Q^b$)—, one of $X^{Qa}$ and $X^{Qb}$ can be an amine group (i.e., —NH$Q^a$ or —NH$Q^b$) and the other can be a carboxyl group (i.e., —COOH) or a reactive derivative thereof (such as acyl halide, such as an acyl chloride or acyl bromide). The groups $P^{5a}$, $P^{5b}$ and $P^6$ can be, for example, benzyl, trimethylsilyl and benzyl or methyl, respectively. When Q is an amide group, the reaction can be performed under conventional amide coupling conditions. Similarly, when the desired group Q is a sulfonamide, i.e., —N($Q^c$)S(O)$_2$— or —S(O)$_2$N($Q^d$)-, one of $X^{Qa}$ and $X^{Qb}$ can be an amine group, —NH$Q^c$ or —NH$Q^d$ and the other can be a sulfonyl halide group (such as sulfonyl chloride or sulfonyl bromide).

Compounds of formula 5 can be prepared by reacting a compound of formula 1 with a compound of formula 21:

$$X^5—(R^{4a})_d-(A^1)_e-(R_{4b})_f—X^{Qa'} \qquad 21$$

wherein $X^5$ represents a leaving group including halo, such as chloro, bromo or iodo, and a sulfonic ester group, such as mesylate or tosylate; and $X^{Qa'}$ represents $X^{Qa}$, such as a carboxyl group or an amino group NH$Q^a$, or a protected derivative thereof, such as a (1-6C)alkoxycarbonylamino group or a tert-butoxycarbonylamino group. This reaction is typically conducted by a method analogous to that used to prepare compounds of formula 3, followed by removing any protecting group in $X^{Qa'}$.

Compounds of formula 6 can be prepared by reacting a compound of formula 10 (where $P^{5a}=P^{13}$, $P^6=P^{12}$, and $R^{6c}=R^{6e}$) with a compound of formula 22:

$$X^{Qb'}—(R^{4c})_g-(A^2)_h-(R^{4d})_i—X^6 \qquad 22$$

wherein $X^6$ represents a leaving group including halo, such as chloro, bromo or iodo, and a sulfonic ester group, such as mesylate or tosylate; and $X^{Qb'}$ represents $X^{Qb}$, such as a carboxyl group or an amino group NH$Q^b$, or a protected derivative thereof, such as a (1-6C)alkoxycarbonyl group or a tert-butoxycarbonylamino group. This reaction is typically conducted by a method analogous to that used to prepare compounds of formula 3, followed by removing any protecting group in $X^{Qb'}$.

Referring to process (d), i.e., the reaction of a compound of formula 3 with a compound of formula 7a or 7b, any suitable reducing agent may be used in this reaction. For example, the reducing agent can be hydrogen in the presence of a Group VIII metal catalyst, such as palladium on carbon; or a metal hydride reagent, such as sodium triacetoxyborohydride. The group $P^7$ can be, for example, benzyl or methyl. This reaction is typically conducted in an inert diluent and a protic solvent, such as a mixture of dichloroethane and methanol, at a temperature in the range of from 0° C. to 100° C. until the reaction is substantially complete.

Compounds of formula 7a or 7b in the form of a hydrate can be prepared by conventional procedures. For example, a compound of formula 7a can be prepared by dibrominating a compound of formula 20 and then hydrolyzing the resulting dibromide to form a glyoxal or a hydrate thereof. For example, a compound of formula 20 can be reacted with hydrogen bromide and then hydrolyzed with water to form the corresponding glyoxal hydrate. Compounds of formula 7b can be prepared, for example, by oxidation of the corresponding alcohol or reduction of the corresponding nitrile or carboxylic acid or ester using conventional reagents and procedures.

Referring to process (e), i.e., the reaction of a compound of formula 1 with a compound of formula 8, any suitable reducing agent may be used in this reaction. For example, the reducing agent may be hydrogen in the presence of a Group VIII metal catalyst, such as palladium on carbon; or a metal hydride reagent, such as sodium triacetoxyborohydride. The groups $P^8$, $P^9$ and $P^{10}$ can be, for example, trimethylsilyl, benzyl or methyl and benzyl, respectively. Typically, this reduction reaction is conducted in an inert diluent and a protic solvent, such as dichloroethane and methanol, at a temperature in the range of from 0° C. to 100° C. until the reaction is substantially complete.

Compounds of formula 8 may be prepared by oxidizing a compound of formula 23:

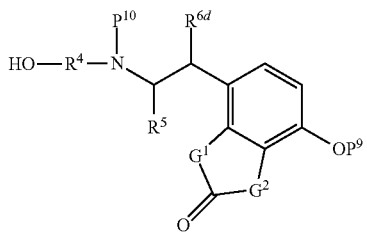

using any suitable oxidizing agent, such as sulfur trioxide pyridine complex and dimethyl sulfoxide. This reaction is typically conducted in the presence of a tertiary amine, such as diisopropylethylamine, at a temperature in the range of from about −20° C. to about 25° C. until the oxidation is substantially complete.

Compounds of formula 23 can be prepared by reacting a compound of formula 10 (where $P^{10}=P^{13}$, $P^9=P^{12}$, and $R^{6d}=R^{6e}$) with a compound of formula 24:

HO—$R^4$—$X^7$     24 wherein $X^7$ represents a leaving group including halo, such as chloro, bromo or iodo, and a sulfonic ester group, such as mesylate or tosylate.

Referring to process (f), i.e., the reaction of a compound of formula 9 with a compound of formula 10, the leaving group represented by $X^3$ can be, for example, halo, such as chloro, bromo or iodo, or a sulfonic ester group, such as mesylate or tosylate. The groups $P^{11}$, $P^{12}$ and $P^{13}$ can be, for example, trimethylsilyl, benzyl or methyl, and benzyl, respectively. This reaction is typically conducted an inert diluent, such as acetonitrile, in the presence of a suitable base. For example, this reaction can be conducted in the presence of a tertiary amine, such as diisopropylethylamine. Generally, this reaction is conducted at a temperature in the range of from 0° C. to 100° C. until the reaction is substantially complete.

Compounds of formula 9 can be prepared by steps analogous to those of methods (a) to (e) herein, starting from a compound of formula 1. Additionally, compounds of formula 10 can be prepared from compounds of formula 4 by reaction with an amine of formula $P^{13}NH_2$.

Referring to process (g), i.e., the reaction of a compound of formula 11 with a compound of formula 10, any suitable reducing agent may be used in this reaction. For example, the reducing agent may be hydrogen in the presence of a Group VIII metal catalyst, such as palladium on carbon; or a metal hydride reagent, such as sodium triacetoxyborohydride. The groups $P^{11}$, $P^{12}$ and $P^{13}$ can be, for example, tert-butyldimethylsilyl, benzyl and benzyl, respectively. Typically, this reduction reaction is conducted in an inert diluent and a protic solvent, such as dichloroethane and methanol, at a temperature in the range of from 0° C. to 100° C. until the reaction is substantially complete.

Compounds of formula 11 are readily prepared by oxidation of the corresponding alcohol or by hydrolysis of the corresponding acetal. Any suitable oxidizing agent may be employed in this reaction to provide the aldehyde, such as sulfur trioxide pyridine complex and dimethyl sulfoxide. The acetal may be hydrolyzed under conventional conditions using aqueous acid to provide the aldehyde.

In a particular embodiment, certain compounds of formula I are prepared by a process comprising:

(h) contacting a compound of formula 25:

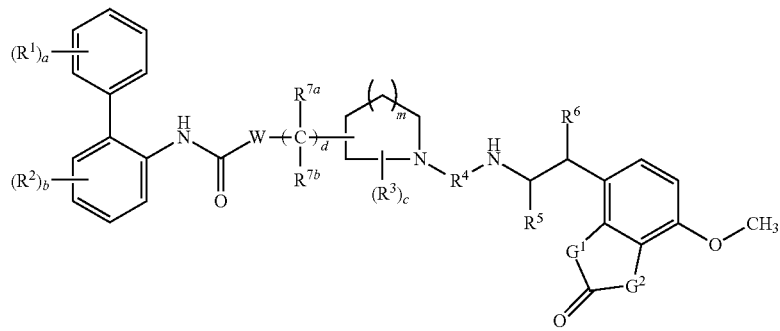

with a reagent selected from boron tribromide, boron trichloride, hydrobromic acid and hydrochloric acid to form a compound of formula I or a salt or stereoisomer thereof; and, optionally, forming a pharmaceutically acceptable salt of the compound of formula I.

Referring to process (h), this reaction is typically conducted by contacting the compound of formula 25 with an excess, such as about 2 to about 6 molar equivalents, of boron tribromide at a temperature ranging from about −30° C. to about 30° C. for about 1 to about 24 hours or until the reaction is substantially complete. The reaction product is then isolated using conventional procedures, such as extraction, recrystallization, chromatography and the like. Compounds of formula 25 can be prepared by the methods described herein, such as by processes (a) to (g).

Further details regarding specific reaction conditions and other procedures for preparing representative compounds of this invention or intermediates thereof are described in the Examples set forth below.

Pharmaceutical Compositions and Formulations

The compounds of this invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration.

It will be understood that any form of the compounds of this invention, (i.e., free base, pharmaceutically acceptable salt, solvate, etc.) that is suitable for the particular mode of administration can be used in the pharmaceutical compositions discussed herein.

Accordingly, in one of its compositions aspects, this invention is directed to a pharmaceutical composition comprising a pharmaceutically acceptable carrier or excipient and a therapeutically effective amount of a compound of this invention, or a pharmaceutically acceptable salt thereof. Optionally, such pharmaceutical compositions may contain other therapeutic and/or formulating agents if desired.

The pharmaceutical compositions of this invention typically contain a therapeutically effective amount of a compound of the present invention or a pharmaceutically acceptable salt thereof. Typically, such pharmaceutical compositions will contain from about 0.01 to about 95% by weight of the active agent; including, from about 0.01 to about 30% by weight; such as from about 0.01 to about 10% by weight of the active agent.

Any conventional carrier or excipient may be used in the pharmaceutical compositions of this invention. The choice of a particular carrier or excipient, or combinations of carriers or exipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a compound of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 μm. Suitable nebulizer devices are provided commercially, for example, by PARI GmbH (Starnberg, German). Other nebulizer devices include Respimat (Boehringer Ingelheim) and those disclosed, for example, in U.S. Pat. No. 6,123,068 and WO 97/12687.

A representative pharmaceutical composition for use in a nebulizer inhaler comprises an isotonic aqueous solution comprising from about 0.05 μg/mL to about 10 mg/mL of a compound of this invention or a pharmaceutically acceptable salt or solvate or stereoisomer thereof.

In another specific embodiment of this invention, the pharmaceutical composition comprising the active agent is administered by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose or starch.

A representative pharmaceutical composition for use in a dry powder inhaler comprises dry lactose having a particle size between about 1 μm and about 100 μm and micronized particles of a compound of this invention, or a pharmaceutically acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); Rotahaler (GlaxoSmithKline) (see, e.g., U.S. Pat. No. 4,353,365) and Handihaler (Boehringer Ingelheim). Further examples of suitable DPI devices are described in U.S. Pat. Nos. 5,415,162, 5,239,993, and 5,715,810 and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183, EP 0717987 A2, and WO 92/22286.

A representative pharmaceutical composition for use in a metered-dose inhaler comprises from about 0.01% to about 5% by weight of a compound of this invention, or a pharmaceutically acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. Nos. 6,006,745 and 6,143,277. Alternatively, a suspension formulation can be prepared by spray drying a coating of surfactant on micronized particles of the active agent. See, for example, WO 99/53901 and WO 00/61108.

For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of this invention will typically comprise a compound of the present invention as the active ingredient and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of this invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The compounds of this invention can also be administered transdermally using known transdermal delivery systems and excipients. For example, a compound of this invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with a compound of this invention, or pharmaceutically acceptable salt or solvate or stereoisomer thereof. For example, the pharmaceutical compositions of this invention may further comprise one or more therapeutic agents selected from other bronchodilators (e.g., $PDE_3$ inhibitors, adenosine 2b modulators and $\beta_2$ adrenergic receptor agonists); anti-inflammatory agents (e.g. steroidal anti-inflammatory agents, such as corticosteroids; non-steroidal anti-inflammatory agents (NSAIDs), and $PDE_4$ inhibitors); other muscarinic receptor antagonists (i.e., anticholinergic agents); antiinfective agents (e.g. Gram positive and Gram negative antibiotics or antivirals); antihistamines; protease inhibitors; and afferent blockers (e.g., $D_2$ agonists and neurokinin modulators). The other therapeutic agents can be used in the form of pharmaceutically acceptable salts or solvates. Additionally, if appropriate, the other therapeutic agents can be used as optically pure stereoisomers.

Representative $\beta_2$ adrenergic receptor agonists that can be used in combination with, and in addition to, the compounds of this invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used in combination with the compounds of this invention include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(−3-{[7-({(2R)-2-hydroxy-2-[4-hydroxy-3-(hydroxymethyl)phenyl]ethyl}-amino)heptyl]oxy}-propyl)benzenesulfonamide and related compounds disclosed in WO 02/066422, published on Aug. 29, 2002; 3-[3-(4-{[6-([(2R)-2-hydroxy-2-[4-hydroxy-3-(hydroxymethyl)phenyl]ethyl}amino)hexyl]oxy}butyl)-phenyl]imidazolidine-2,4-dione and related compounds disclosed in WO 02/070490, published Sep. 12, 2002; 3-(4-{[6-({(2R)-2-[3-(formylamino)-4-hydroxyphenyl]-2-hydroxyethyl}amino)hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]-oxy}butyl)benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl)benzenesulfonamide and related compounds disclosed in WO 02/076933, published on Oct. 3, 2002; 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439, published on Mar. 27, 2003; and pharmaceutically acceptable salts thereof. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 µg to about 500 µg per dose.

Representative steroidal anti-inflammatory agents that can be used in combination with the compounds of this invention include, but are not limited to, methyl prednisolone, prednisolone, dexamethasone, fluticasone propionate, 6,9-difluoro-17-[(2-furanylcarbonyl)oxy]-11-hydroxy-16-methyl-3-oxoandrosta-1,4-diene-17-carbothioic acid S-fluoromethyl ester, 6,9-difluoro-11-hydroxy-16-methyl-3-oxo-17-propionyloxy-androsta-1,4-diene-17-carbothioic acid S-(2-oxo-tetrahydrofuran-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the pharmaceutical composition in a therapeutically effective amount. Typically, the steroidal anti-inflammatory agent will be present in an amount sufficient to provide from about 0.05 µg to about 500 µg per dose.

Other suitable combinations include, for example, other anti-inflammatory agents, e.g., NSAIDs (such as sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (IL antibody), specifically, an IL-4 therapy, an IL-13 therapy, or a combination thereof); or inhibitors of cytokine synthesis.

For example, representative phosphodiesterase-4 (PDE4) inhibitors or mixed PDE3/PDE4 inhibitors that can be used in combination with the compounds of this invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); phthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with, and in addition to, the compounds of this invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the compounds of this invention include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Suitable doses for the other therapeutic agents administered in combination with a compound of the invention are in the range of about 0.05 g/day to about 100 mg/day.

The following formulations illustrate representative pharmaceutical compositions of the present invention:

Formulation Example A

A dry powder for administration by inhalation is prepared as follows:

| Ingredients | Amount |
| --- | --- |
| Compound of the invention | 0.2 mg |
| Lactose | 25 mg |

Representative Procedure: The compound of the invention is micronized and then blended with lactose. This blended mixture is then loaded into a gelatin inhalation cartridge. The contents of the cartridge are administered using a powder inhaler.

Formulation Example B

A dry powder formulation for use in a dry powder inhalation device is prepared as follows:
Representative Procedure: A pharmaceutical composition is prepared having a bulk formulation ratio of micronized compound of the invention to lactose of 1:200. The composition is packed into a dry powder inhalation device capable of delivering between about 10 μg and about 100 μg of the compound of the invention per dose.

Formulation Example C

A dry powder for administration by inhalation in a metered dose inhaler is prepared as follows:
Representative Procedure: A suspension containing 5 wt. % of a compound of the invention and 0.1 wt. % lecithin is prepared by dispersing 10 g of the compound of the invention as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example D

A pharmaceutical composition for use in a metered dose inhaler is prepared as follows:
Representative Procedure: A suspension containing 5% compound of the invention, 0.5% lecithin, and 0.5% trehalose is prepared by dispersing 5 g of active ingredient as micronized particles with mean size less than 10 m in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Formulation Example E

A pharmaceutical composition for use in a nebulizer inhaler is prepared as follows:
Representative Procedure: An aqueous aerosol formulation for use in a nebulizer is prepared by dissolving 0.1 mg of the compound of the invention in 1 mL of a 0.9% sodium chloride solution acidified with citric acid. The mixture is stirred and sonicated until the active ingredient is dissolved. The pH of the solution is adjusted to a value in the range of from 3 to 8 by the slow addition of NaOH.

Formulation Example F

Hard gelatin capsules for oral administration are prepared as follows:

| Ingredients | Amount |
| --- | --- |
| Compound of the invention | 250 mg |
| Lactose (spray-dried) | 200 mg |
| Magnesium stearate | 10 mg |

Representative Procedure: The ingredients are thoroughly blended and then loaded into a hard gelatin capsule (460 mg of composition per capsule).

Formulation Example G

A suspension for oral administration is prepared as follows:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 100 mg of active ingredient per 10 mL of suspension.

Formulation Example H

An injectable formulation is prepared as follows:

| Ingredients | Amount |
| --- | --- |
| Compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Utility

The compounds of this invention possess both $\beta_2$ adrenergic receptor agonist and muscarinic receptor antagonist activity and therefore, such compounds are expected to be useful for treating medical conditions mediated by $\beta_2$ adrenergic receptors or muscarinic receptors, i.e., medical conditions that are ameliorated by treatment with a $\beta_2$ adrenergic receptor agonist or a muscarinic receptor antagonist. Such medical conditions include, by way of example, pulmonary disorders or diseases associated with reversible airway obstruction, such as chronic obstructive pulmonary disease (e.g., chronic and wheezy bronchitis and emphysema), asthma, pulmonary fibrosis and the like. Other conditions which may be treated include premature labor, depression, congestive heart failure, skin diseases (e.g., inflammatory, allergic, psoriatic and proliferative skin diseases, conditions where lowering peptic acidity is desirable (e.g., peptic and gastric ulceration) and muscle wasting disease.

Accordingly, in one embodiment, this invention is directed to a method for treating a pulmonary disorder, the method comprising administering to a patient in need of treatment a therapeutically effective amount of a compound of this invention or a pharmaceutically acceptable salt or solvate or stereoisomer thereof. When used to treat a pulmonary disorder, the compounds of this invention will typically be administered by inhalation in multiple doses per day, in a single daily dose or a single weekly dose. Generally, the dose for treating a pulmonary disorder will range from about 10 μg/day to about 200 μg/day.

When administered by inhalation, the compounds of this invention typically have the effect of providing bronchodilation. Accordingly, in another of its method aspects, this invention is directed to a method of producing bronchodilation in a patient, the method comprising administering to the patient requiring bronchodilation a bronchodilation-producing amount of a compound of this invention or a pharmaceutically acceptable salt or solvate or stereoisomer thereof. Generally, the dose for providing bronchodilation will range from about 10 μg/day to about 200 μg/day.

In one embodiment, this invention is directed to a method of treating chronic obstructive pulmonary disease or asthma, the method comprising administering to a patient in need of treatment a therapeutically effective amount of a compound of this invention or a pharmaceutically acceptable salt or solvate or stereoisomer thereof. When used to treat a COPD or asthma, the compounds of this invention will typically be administered by inhalation in multiple doses per day or in a single daily dose. Generally, the dose for treating COPD or asthma will range from about 10 μg/day to about 200 μg/day.

As used herein, COPD includes chronic obstructive bronchitis and emphysema (see, for example, Barnes, Chronic Obstructive Pulmonary Disease, *N Engl J Med* 2000: 343: 269-78).

When used to treat a pulmonary disorder, the compounds of this invention are optionally administered in combination with other therapeutic agents. In particular, by combining the compounds of this invention with a steroidal anti-inflammatory agent (e.g. a corticosteroid), the pharmaceutical compositions of this invention can provide triple therapy, i.e., $\beta_2$ adrenergic receptor agonist, muscarinic receptor antagonist and anti-inflammatory activity, using only two active components. Since pharmaceutical compositions containing two active components are typically easier to formulate compared to compositions containing three active components, such two component compositions provide a significant advantage over compositions containing three active components. Accordingly, in a particular embodiment, the pharmaceutical compositions and methods of this invention further comprise a therapeutically effective amount of a steroidal anti-inflammatory agent.

Compounds of this invention exhibit both muscarinic receptor antagonist and $\beta_2$ adrenergic receptor agonist activity. Accordingly, among other properties, compounds of particular interest are those that demonstrate an inhibitory constant $K_i$ value for binding at the $M_3$ muscarinic receptor and an $EC_{50}$ value for $\beta_2$ adrenergic receptor agonist activity of less than about 100 nM; particularly less than 10 nM. Among these compounds, compounds of special interest include those having muscarinic activity, expressed in terms of the inhibitory constant $K_i$ for binding at the $M_3$ muscarinic receptor, that is about equal to the compound's $\beta_2$ adrenergic agonist activity, expressed in terms of the half maximal effective concentration $EC_{50}$, as determined in the in vitro assays described herein, or in similar assays. For example, compounds of particular interest are those having a ratio of the inhibitory constant $K_i$ for the $M_3$ muscarinic receptor to the $EC_{50}$ for the $\beta_2$ adrenergic receptor ranging from about 30:1 to about 1:30; including about 20:1 to about 1:20; such as about 10:1 to about 1:10.

Since compounds of this invention possess both $\beta_2$ adrenergic agonist activity and muscarinic receptor antagonist activity, such compounds are also useful as research tools for investigating or studying biological systems or samples having $\beta_2$ adrenergic receptors or muscarinic receptors or combinations thereof, or for discovering new compounds having both $\beta_2$ adrenergic agonist activity and muscarinic receptor antagonist activity. Such biological systems or samples may comprise $\beta_2$ adrenergic receptors and/or muscarinic receptors. Any suitable biological system or sample having $\beta_2$ adrenergic and/or muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

In this embodiment, a biological system or sample comprising a $\beta_2$ adrenergic receptor or a muscarinic receptor or a combination thereof is contacted with a $\beta_2$ adrenergic receptor-agonizing or muscarinic receptor-antagonizing amount of a compound of this invention. The response of the biological system or sample to the compound is then measured, or the effects of the compound on the biological system or sample are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(-thio)triphosphate ([$^{35}$S]GTP S) into isolated membranes via receptor catalyzed exchange of [$^{35}$S]GTP S for GDP, ligand-mediated changes in free intracellular calcium ions (measured, for example, with a fluorescence-linked imaging plate reader or HAW from Molecular Devices, Inc.). A compound of this invention will agonize or cause activation of a $\beta_2$ adrenergic receptor and antagonize or decrease the activation of muscarinic receptors in any of the functional assays listed above, or assays of a similar nature. The amount of compound used in these studies will typically range from about 0.1 nanomolar to about 100 nanomolar.

Additionally, the compounds of this invention can be used as research tools for discovering new compounds that have both a $\beta_2$ adrenergic receptor agonist and muscarinic receptor antagonist activity. In this embodiment, a $\beta_2$ adrenergic receptor and muscarinic receptor binding data (for example, as determined by in vitro radioligand displacement assays) for a test compound or a group of test compounds is compared to the $\beta_2$ adrenergic receptor and muscarinic receptor binding data for a compound of this invention to identify those test compounds that have about equal or superior $\beta_2$ adrenergic receptor and/or muscarinic receptor binding, if any. This aspect of the invention includes, as separate embodiments, both the generation of comparison data (using the appropriate assays) and the analysis of the test data to identify test compounds of interest.

The properties and utility of the compounds of this invention can be demonstrated using various in vitro and in vivo assays well-known to those skilled in the art. For example, representative assays are described in further detail in the following Examples.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard meaning:

AC adenylyl cyclase
Ach acetylcholine
ATCC American Type Culture Collection
BSA bovine serum albumin
cAMP 3'-5' cyclic adenosine monophosphate
CHO Chinese hamster ovary
$cM_5$ cloned chimpanzee $M_5$ receptor
DCM dichloromethane (i.e., methylene chloride)
DIPEA N,N-diisopropylethylamine
dPBS Dulbecco's phosphate buffered saline
DMEM Dulbecco's Modified Eagle's Medium
DMSO dimethyl sulfoxide
EDTA ethylenediaminetetraacetic acid
Emax maximal efficacy
EtOAc ethyl acetate
EtOH ethanol
FBS fetal bovine serum
FLIPR fluorometric imaging plate reader
Gly glycine
HATU O-(7-azabenzotriazol-1-yl-N,N,N',N'-tetramethyluronium hexafluorophosphate
HBSS Hank's buffered salt solution
HEK human embryonic kidney cells
HEPES 4-(2-hydroxyethyl)-1-piperazineethanesulfonic acid
$hM_1$ cloned human $M_1$ receptor
$hM_2$ cloned human $M_2$ receptor
$hM_3$ cloned human $M_3$ receptor
$hM_4$ cloned human $M_4$ receptor
$hM_5$ cloned human $M_5$ receptor
HPLC high-performance liquid chromatography
IBMX 3-isobutyl-1-methylxanthine
% Eff % efficacy
PBS phosphate buffered saline
PyBOP benzotriazol-1-yloxytripyrrolidinophosphonium hexafluorophosphate
rpm rotations per minute
TFA trifluoroacetic acid
THF tetrahydrofuran
Tris tris(hydroxymethyl)aminomethane Unless noted otherwise, reagents, starting materials and solvents were purchased from commercial suppliers (such as Aldrich, Fluka, Sigma and the like) and were used without further purification.

In the examples described below, HPLC analysis was conducted using an Agilent (Palo Alto, Calif.) Series 1100 instrument with Zorbax Bonus RP 2.1×50 mm columns, supplied by Agilent, (a C14 column), having a 3.5 micron particle size. Detection was by UV absorbance at 214 nm. HPLC 10-70 data was obtained with a flow rate of 0.5 mL/minute of 10%-70% B over 6 minutes. Mobile phase A was 2%-98%-0.1% ACN-$H_2$O-TFA; and mobile phase B was 90%-10%-0.1% ACN-$H_2$O-TFA. Using the mobile phases A and B described above, HPLC 5-35 data and HPLC 10-90 data were obtained with a 5 minute gradient.

Liquid chromatography mass spectrometry (LCMS) data were obtained with an Applied Biosystems (Foster City, Calif.) model API-150EX instrument. LCMS 10-90 data was obtained with a 10%-90% mobile phase B over a 5 minute gradient.

Small scale purification was conducted using an API 150EX Prep Workstation system from Applied Biosystems. The mobile phase was A: water+0.05% v/v TFA; and B: acetonitrile+0.05% v/v TFA. For arrays (typically about 3 to 50 mg recovered sample size) the following conditions were used: 20 mL/min flow rate; 15 min gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 min gradients and a 41.4 mm×250 mm Microsorb BDS column with 10 micron particles (Varian, Palo Alto, Calif.).

The specific rotation for chiral compounds (indicated as $[\alpha]^{20}_D$) was measured using a Jasco Polarimeter (Model P-1010) with a tungsten halogen light source and a 589 nm filter at 20° C. Samples of test compounds were typically measured at 1 mg/mL water.

Example 1

Biphenyl-2-ylcarbamic Acid 1-{9-[2-(4-Hydroxy-2-oxo-2,3-dihydrobenzothiazol-7-yl)-ethylamino]nonyl}piperidin-4-yl Ester Bis(trifluoroacetate) Salt Step 1—Biphenyl-2-ylcarbamic Acid Piperidin-4-yl Ester
Biphenyl-2-isocyanate (97.5 g, 521 mmol) and 4-hydroxy-1-benzylpiperidine (105 g, 549 mmol), both commercially-available from Aldrich, Milwaukee, Wis., were heated together at 70° C. for 12 h, during which time the formation of biphenyl-2-ylcarbamic acid 1-benzylpiperidin-4-yl ester was monitored by LCMS. The reaction mixture was then cooled to 50° C. and ethanol (1 L) was added, and then 6M hydrochloric acid (191 mL) was added slowly. The reaction mixture was then cooled to ambient temperature and ammonium formate (98.5 g, 1.56 mol) was added and nitrogen gas was bubbled through the solution vigorously for 20 min. Palladium (10 wt. % (dry basis) on activated carbon) (20 g) was then added. The reaction mixture was heated at 40° C. for 12 h and then filtered through a pad of Celite. The solvent was then removed under reduced pressure and 1M hydrochloric acid (40 mL) was added to the crude residue. Sodium hydroxide (10N) was then added to adjust the pH to 12. The aqueous layer was extracted with ethyl acetate (2×150 mL) and dried (magnesium sulfate), and then the solvent was removed under reduced pressure to give the title compound (155 g, 100% yield). HPLC (10-70) $R_t$=2.52; MS m/z: [M+H$^+$] calc'd for $C_{18}H_{20}N_2O_2$ 297.15; found 297.3.

Step 2—Biphenyl-2-ylcarbamic Acid 1-(9-Hydroxynonyl)piperidin-4-yl Ester
A solution of biphenyl-2-ylcarbamic acid piperidin-4-yl ester (5 g, 16.9 mmol), 9-bromo-1-nonanol (4.9 g, 22 mmol) and N,N-diisopropylethylamine (8.8 mL, 50.7 mmol) in acetonitrile (100 mL) was heated to 60° C. for 12 hours. The reaction mixture was cooled and concentrated to dryness. The residue was dissolved in dichloromethane (50 mL) and this solution was washed with 0.05N HCl (50 mL) and brine and then dried over magnesium sulfate. The solvent was evaporated to yield the title compound, (6 g, 81% yield) which was used without further purification in the next step. MS m/z: [M+H$^+$] calcd for $C_{27}H_{38}N_2O_3$ 439.3; found 439.3.

Step 3—Biphenyl-2-ylcarbamic Acid 1-(9-Oxononyl)piperidin-4-yl Ester
A solution of the product of Step 2 (6 g, 13.7 mmol), N,N-diisopropylethylamine (7.15 mL, 41.1 mmol) and dimethyl sulfoxide (20 mL) was in dichloromethane (100 mL) was cooled to 0° C. After 15 minutes, pyridine sulfur trioxide (6.54 g, 41.1 mmol) was added in two portions to the cooled reaction mixture. After 2 hours at 0° C., the reaction was quenched with water (50 mL). The organic layer was then washed with water (3×50 mL) and concentrated to yield the title compound (5.8 g) which was used without further purification in the next step. MS m/z: [M+H$^+$] calcd for $C_{27}H_{36}N_2O_3$ 437.3; found 437.4.

Step 4—7-(2-Aminoethyl)-4-methoxy-1,3-benzothiazol-2(3H)-one Hydrochloride (a) 7-Acetonitrile-2,4-dimethoxybenzothiazole The title compound was prepared using the procedures described in J. Weinstock et al., *J. Med. Chem.*, 1987, 30, 1166-1176. Following the procedures in Weinstock at page 1173 and using 2-methoxy-5-methylphenylthiourea (Lancaster Synthesis, Ltd., Windham, N.H.), the title compound was prepared with the following minor modifications in the synthesis of 2,4-dimethoxybenzothiazole-7-acetonitrile: (1) 2,2'-azobisisobutyronitrile (Aldrich, Milwaukee, Wis.) was substituted for benzoyl peroxide; and (2) the reaction mixture was refluxed under nitrogen for 30 minutes instead of being irradiated with a 150-W tungsten lamp, and then the reaction mixture was cooled to 10° C. and filtered.

(b) 7-(2-Aminoethyl)-4-methoxy-3H-benzothiazol-2-one

The title compound was prepared using the procedure described in J. Weinstock et al., *J. Med. Chem.*, 1987, 30, 1166-1176. MS m/z: [M+H$^+$] calcd for $C_{10}H_{12}N_2O_2S$ 225.1; found 225.1. $^1$H NMR (CDCl$_3$) $\delta$=2.60 (t, 2H, CH$_2$), 2.80 (t, 2H, CH$_2$), 3.60 (s, 3H, OCH$_3$), 6.82 (dd, 2H Ar).

Step 5—Biphenyl-2-ylcarbamic Acid 1-{9-[2-(4-Methoxy-2-oxo-2,3-dihydrobenzothiazol-7-yl)-ethylamino]nonyl}piperidin-4-yl Ester The product of Step 3 (91 mg, 0.35 mmol) was added to a mixture of the product of Step 4 (153 mg, 0.35 mmol) and N,N-diisopropylethylamine (0.061 mL, 0.35 mmol) in dichloromethane (1.75 mL), and the resulting mixture was stirred at room temperature for 2 hours. Sodium triacetoxyborohydride (88 mg, 0.42 mmol) was added and the mixture was stirred at room temperature for 12 hours, at which time the reaction was determined to be complete by LCMS (10-90) analysis. The reaction mixture was then quenched with 6 N ammonium chloride solution (2 mL) and the organic layer was separated. The organic layer was washed with brine, dried over magnesium sulfate and concentrated to give the title compound (145 mg). MS m/z: [M+H$^+$] calcd for $C_{37}H_{48}N_4O_4S$ 645.3; found 645.8.

Step 6—Biphenyl-2-ylcarbamic Acid 1-{9-[2-(4-Hydroxy-2-oxo-2,3-dihydrobenzothiazol-7-yl)-ethylamino]nonyl}piperidin-4-yl Ester Bis(trifluoroacetate) Salt A solution of the product of Step 5 (138 mg, 0.21 mmol) in dichloromethane (1 mL) was cooled to −10° C. and 1.0 M boron tribromide in dichloromethane (1.1 mL) was added. After ten minutes, the ice bath was removed and the reaction mixture was allowed to slowly warm to room temperature. After 3 hours, the reaction was determined to be complete by MS analysis. The reaction mixture was then quenched with methanol (1 mL) and concentrated in vacuo. The residue was purified by HPLC (5-35) to give the title compound (9.8 mg, 98% pure). HPLC (10-70) R$_t$=2.9; MS m/z: [M+H$^+$] calcd for $C_{36}H_{46}N_4O_4S$ 631.3; found 631.8.

Example 2

Biphenyl-2-ylcarbamic Acid 1-[2-(4-{[2-(4-Hydroxy-2-oxo-2,3-dihydrobenzothiazol-7-yl)ethylamino]methyl}phenylcarbamoyl)ethyl]-piperidin-4-yl Ester Bis(trifluoroacetate) Salt Step 1—N-(4-Hydroxymethylphenyl)acrylamide p-Aminobenzyl alcohol (12.31 g, 100 mmol) was dissolved in a mixture of dichloromethane (200 mL) and tetrahydrofuran (20 mL) containing N,N-diisopropylethylamine (35 mL, 200 mmol). The resulting homogeneous solution was then cooled to 0° C. and acryloyl chloride (8.2 mL, 100 mmol) was added drop-wise over a 30-minute period while keeping the internal temperature of the reaction mixture below 20° C. The reaction mixture was stirred at 0° C. for about 60 minutes. The reaction mixture was poured into ice-cold 1M hydrochloric acid (0.6 L) and the organic layer was separated and evaporated to dryness to give a crude material (5 g) consisting primarily of the bis-acylated side product. The acidic aqueous layer was then extracted with ethyl acetate (2×200 mL) and the combined ethyl acetate layers were dried with sodium sulfate, filtered and concentrated under reduced pressure to provide a residue. Trituration of the residue with ethyl acetate yielded the title compound (10.5 g, 98.5% pure). An additional 2 g of the title compound were obtained by trituration of the crude material obtained from the dichloromethane layer.

Step 2—Biphenyl-2-ylcarbamic Acid 1-[2-(4-Hydroxymethylphenylcarbamoyl)ethyl]piperidin-4-yl Ester The product of Step 1 (10 g, 57 mmol) and biphenyl-2-ylcarbamic acid piperidin-4-yl ester from Example 1, Step 1 (17.8 g, 60 mmol) were dissolved in a mixture of methanol (100 mL) and dichloromethane (100 mL) and the resulting mixture was heated at 55° C. (reflux) for 18 hours. Most of the solvent was then removed under reduced pressure and the resulting residue was triturated with ethyl acetate (200 mL) to give a solid that was isolated by filtration. The solid was dried under vacuum to give the title compound (25 g).

Step 3—Biphenyl-2-ylcarbamic Acid 1-[2-(4-Formylphenylcarbamoyl)ethyl]piperidin-4-yl Ester The product of Step 2 (20 g, 42.3 mmol) was dissolved in anhydrous dichloromethane (200 mL) containing DMSO (18 mL, 254 mmol) and N,N-diisopropylethylamine (37 mL, 211.5 mmol). The resulting homogeneous solution was cooled to −20° C. and then sulfur trioxide pyridine complex (20.2 g) was added in portions over a 30-minute period while maintaining the internal temperature of the reaction mixture below −10° C. The reaction mixture was then stirred at −10° C. for about 30 minutes. The reaction mixture was then poured into an ice-cold mixture of 1M hydrochloric acid (100 mL) and water (500 mL) (the mixture had a pH of about 6). The mixture was extracted with dichloromethane (300 mL) and the dichloromethane layer was then washed with brine (200 mL), dried with sodium sulfate and concentrated under reduced pressure. Some precipitation was observed during solvent removal. Ethyl acetate (100 mL) was added to the resulting thick slurry. The resulting solid was isolated by filtration and dried under vacuum to give the title compound (11 g, 99% purity by HPLC). The slurry solvent was concentrated under reduced pressure to give additional solid that was isolated by filtration and dried under vacuum to give the title compound (5.4 g, 96% purity by HPLC). HPLC (2%-70% acetonitrile in water/0.1% TFA); R$_t$=5.7. MS m/z: [M+H$^+$] calcd for $C_{28}H_{29}N_3O_4$ 472.2; found 472.0.

Step 4—Biphenyl-2-ylcarbamic Acid 1-[2-(4-{[2-(4-Methoxy-2-oxo-2,3-dihydrobenzothiazol-7-yl)ethylamino]methyl}phenylcarbamoyl)ethyl]-piperidin-4-yl Ester The product of Step 3 (163 mg, 0.35 mmol) was added to a mixture of the product of Example 1, Step 4 (100 mg, 0.38 mmol) and N,N-diisopropylethylamine (0.067 mL, 0.38 mmol) in dichloromethane (1.75 mL) and the resulting mixture was stirred at room temperature for 2 hours. Sodium triacetoxyborohydride (122 mg, 0.58 mmol) was added and the resulting mixture was stirred at room temperature for about 2 hours. The reaction mixture was quenched with 6 N ammonium chloride (2 mL) and the organic layer was separated. The organic layer was washed with brine, dried over magnesium sulfate and concentrated under vacuum to give the title compound as a solid (127 mg). MS m/z: [M+H$^+$] calcd for $C_{38}H_{41}N_5O_5S$ 680.3; found 680.8.

Step 5—Biphenyl-2-ylcarbamic Acid 1-[2-(4-{[2-(4-Hydroxy-2-oxo-2,3-dihydrobenzothiazol-7-yl)ethylamino]methyl}phenylcarbamoyl)ethyl]-piperidin-4-yl Ester Bis(trifluoroacetate) Salt A solution of the product of Step 4 (127 mg, 0.19 mmol) in dichloromethane (1 mL) was cooled to −10° C. and a 1 M solution of boron tribromide in dichloromethane (0.94 mL) was added. After 10 minutes, the ice bath was removed and the reaction mixture was allowed to slowly warm to room temperature. After 3 hours, the reaction was determined to be complete by MS analysis. The reaction mixture was quenched by slowly adding methanol (1 mL) and then concentrated in vacuo. The crude mixture was then purified using HPLC (5-35) to give the title compound as a powder (11.7 mg, 98% purity). MS m/z: [M+H$^+$] calcd for $C_{37}H_{39}N_5O_5S$ 666.3; found 666.5.

Example 3

3-[4-(3-Biphenyl-2-ylureido)piperidin-1-yl]-N-(4-{[2-(4-hydroxy-2-oxo-2,3-dihydro-benzothiazol-7-yl)ethylamino]methyl}-phenyl)propionamide Step 1—N-1,1'-Biphenyl-2-yl-N'-4-piperidinylurea
(a) N-1,1'-Biphenyl-2-yl-N'-4-(1-benzyl)piperidinylurea
Biphenyl-2-isocyanate (50 g, 256 mmol) was dissolved in acetonitrile (400 mL) at ambient temperature. After cooling to 0° C., a solution of 4-amino-N-benzylpiperidine (48.8 g, 256 mmol) in acetonitrile (400 mL) was added over 5 minutes. A precipitate was observed immediately. After 15 minutes, acetonitrile (600 mL) was added, and the resultant viscous mixture was stirred for 12 hours at 35° C. The solids were filtered and washed with cold acetonitrile and then dried under vacuum to give the title compound (100 g, 98% yield). MS m/z: [M+H$^+$] calcd for $C_{25}H_{27}N_3O$ 386.22; found 386.3.

(b) N-1,1'-Biphenyl-2-yl-N'-4-piperidinylurea
The product of Step (a) (20 g, 52 mmol) was dissolved in a mixture of anhydrous methanol and anhydrous DMF (3:1 v/v, 800 mL). Aqueous hydrochloric acid (0.75 mL of 37% conc. solution, 7.6 mmol) was added and nitrogen gas was bubbled through the solution vigorously for 20 minutes. Pearlman's catalyst (Pd(OH)$_2$, 5 g) was added under a stream of nitrogen, before placing the reaction mixture under a hydrogen atmosphere (balloon). The reaction mixture was allowed to stir for 4 days and was then passed twice through pads of Celite to remove the catalyst. The solvent was then removed under reduced pressure to give the title compound (13 g, 85% yield). MS m/z: [M+H$^+$] calcd for $C_{18}H_{21}N_3O$ 296.2; found 296.0.

Alternatively, N-1,1'-biphenyl-2-yl-N'-4-piperidinylurea was synthesized by heating together biphenyl-2-isocyanate (50 g, 256 mmol) and 4-amino-1-benzylpiperidine (51.1 g, 269 mmol) at 70° C. for 12 hours (monitored by LCMS analysis). The reaction mixture was cooled to 50° C. and ethanol (500 mL) added, followed by slow addition of 6M hydrochloric acid (95 mL). The reaction mixture was cooled to room temperature. Ammonium formate (48.4 g, 768 mmol) was added to the reaction mixture and nitrogen gas bubbled through the solution vigorously for 20 minutes, before adding palladium (10 wt. % (dry basis) on activated carbon) (10 g). The reaction mixture was heated at 40° C. for 12 hours, before filtering through a pad of Celite and the solvent removed under reduced pressure. To the crude residue was added 1M hydrochloric acid (20 mL) and 10N sodium hydroxide was added to adjust the pH to 12. The aqueous layer was extracted with ethyl acetate (2×80 mL), dried (magnesium sulfate) and the solvent removed under reduced pressure to give the title compound as a solid (71.7 g, 95% yield). MS m/z: [M+H$^+$] calcd for $C_{18}H_{21}N_3O$ 296.2; found 296.0.

Step 2—N-(4-(1,3-Dioxolan-2-yl)phenyl)acrylamide
(a) 2-(4-Nitrophenyl)-[1,3]-dioxolane
In a 3-neck round-bottom flask equipped with Dean-Stark apparatus, reflux condenser and mechanical stirrer, p-nitrobenzaldehyde (101.5 g, 672 mmol), ethylene glycol (112 mL, 2.0 mol), and p-toluene sulfonic acid (12.8 g, 67.2 mmol, 10% mol) were suspended in toluene (800 mL) and then heated at 120° C. for 4 hours. The reaction mixture was cooled to room temperature and the toluene was removed under reduced pressure. Saturated aqueous sodium bicarbonate solution (800 mL) was added, and the resulting slurry was stirred at room temperature for 15 minutes, and then filtered and dried under vacuum to give the title compound (121.8 g) as a solid. $^1$H NMR (DMSO-d$_6$): δ=8.12 (d, 2H), 7.59 (d 2H), 5.78 (s, 1H), 3.8-4.0 (m, 4H).

(b) 4-([1,3]Dioxolan-2-yl)phenylamine
The product of Step (a) (10 g, 51 mmol) was dissolved in a mixture of tetrahydrofuran (50 mL) and ethanol (50 mL) and then hydrogenated at 50 psi for 18 hours using platinum oxide catalyst (PtO$_2$) (116 mg, 0.51 mmol). The reaction mixture was filtered through Celite and then the solvent was removed under reduced pressure to give the title compound (8 g), which was used in the next step without further purification. $^1$H NMR (DMSO-d$_6$): δ=6.98 (d, 2H), 6.42 (d, 2H), 5.39 (s, 1H), 5.08 (s, 2H) 3.7-3.9 (m, 4H).

(c) N-(4-([1,3]Dioxolan-2-yl)phenyl)acrylamide
The product from Step (b) (8 g, 48.5 mmol)) and triethylamine (10.1 mL, 72.75 mmol) were dissolved in dichloromethane (100 mL). The resulting homogeneous solution was cooled to 0° C. and acryloyl chloride (4.81 mL, 58.2 mmol was added dropwise. The reaction mixture was stirred at 0° C. for 1 hour and then quenched with water (100 mL). The organic layer was washed with water (50 mL), dried with sodium sulfate and concentrated under reduced pressure to remove most of the dichloromethane. Ethyl acetate (100 mL) was added to the residue and the resulting precipate was collected by filtration and then dried under vacuum to afford the title compound (8.5 g). $^1$H NMR (DMSO-d$_6$): δ=10.10 (s, 1H), 7.61 (d, 2H), 7.25 (d, 2H), 6.1-6.4 (m, 2H), 5.62 (d, 1H), 5.58 (s, 1H), 3.7-4.0 (m, 4H).

Step 3—3-[4-(3-Biphenyl-2-ylureido)piperidin-1-yl]-N-(4-([1,3]dioxolan-2-yl)phenyl)-propionamide
The product of Step 1 (543 mg, 1 mmol) was added to a solution of the product of Step 2 (385 mg, 1.7 mmol) in a mixture of methanol (3 mL) and dichloromethane (3 mL) and the resulting mixture heated to reflux for 12 hours. The reaction mixture was then cooled and concentrated under vacuum. The residue was triturated with ethyl acetate and the resulting precipate was isolated by filtration to give the title compound (731 mg) as a solid. MS m/z: [M+H$^+$] calcd for $C_{30}H_{34}N_4O_4$ 515.3; found 515.5.

Step 4—3-[4-(3-Biphenyl-2-ylureido)piperidin-1-yl]-N-(4-formylphenyl)propionamide
To a solution of the product of Step 3 (731 mg, 1.4 mmol) in methanol was added 1 M hydrochloric acid (2 mL) and the resulting mixture was stirred at room temperature for two hours. The crude reaction mixture was then concentrated under vacuum and then diluted with dichloromethane. The organic layer was washed with saturated sodium bicarbonate (2×5 mL) and then brine (5 mL) The organic layer was dried over magnesium sulfate, filtered, and concentrated to give the title compound (600 mg) as an oil. MS m/z: [M+H$^+$] calcd for $C_{28}H_{30}N_4O_3$ 471.2; found 471.5.

Step 5—3-[4-(3-Biphenyl-2-ylureido)piperidin-1-yl]-N-(4-{[2-(4-methoxy-2-oxo-2,3-dihydrobenzothiazol-7-yl)ethylamino]methyl}phenyl)propionamide
The product of Example 1, Step 4 (131 mg, 0.58 mmol) was added to a solution of the product of Step 4 (183 mg, 0.39 mmol) and N,N-diisopropylethylamine (0.102 mL, 0.58 mmol) in a mixture of dichloromethane (1 mL) and methanol (1 mL) and the resulting mixture was stirred for 30 minutes at room temperature. After 30 minutes, sodium triacetoxyborohydride (123 mg, 0.58 mmol) was added and stirring was continued at room temperature. After 2 hours, the reaction mixture was quenched with 6 N aqueous ammonium chloride (2 mL) and the organic layer was separated. The organic layer was washed with saturated sodium bicarbonate (2×5 mL) and then brine (5 mL). The organic layer was dried over magnesium sulfate, filtered, and then concentrated under vacuum to give the title compound (169 mg) as a solid. MS m/z: [M+H$^+$] calcd for $C_{38}H_{42}N_6O_4S$ 679.3; found 679.5.

Step 6—3-[4-(3-Biphenyl-2-ylureido)piperidin-1-yl]-N-(4-{[2-(4-hydroxy-2-oxo-2,3-dihydrobenzothiazol-7-yl)ethylamino]methyl}phenyl)propionamide A solution of the product of Step 5 (169 mg, 0.25 mmol) in dichloromethane (1.2 mL) was cooled in an ice/acetone bath. After about 10 minutes, a 1.0 M solution of boron tribromide in dichloromethane (1.2 mL) was slowly added to the reaction mixture while the reaction mixture was stirred in the ice/acetone bath. After 30 minutes, the reaction mixture was removed from the ice bath and slowly warmed to room temperature. After 15 hours, the reaction mixture was slowly quenched with methanol (2 mL) and concentrated under vacuum. The reaction was purified on a small-scale HPLC to give the title compound (8.7 mg, 71% purity). MS m/z: [M+H$^+$] calcd for $C_{37}H_{40}N_6O_4S$ 665.3; found 665.5. HPLC (10-70) $R_t$=2.97.

Example 4

Biphenyl-2-ylcarbamic Acid 1-[2-(4-{2-[2-(4-Hydroxy-2-oxo-2,3-dihydrobenzothiazol-7-yl)-ethylamino]ethyl}phenylcarbamoyl)ethyl]-piperidin-4-yl Ester Bis(trifluoroacetate) Salt Step 1—3-[4-(Biphenyl-2-ylcarbamoyloxy)piperidin-1-yl]propionic Acid (a) Methyl 3-[4-(Biphenyl-2-ylcarbamoyloxy)piperidin-1-yl]propionate Methyl 3-bromopropionate (553 µL, 5.07 mmol) was added to a stirred solution of the product from Example 1, Step 1 (1.00 g, 3.38 mmol) and diisopropylethylamine (1.76 mL, 10.1 mmol) in acetonitrile (34 mL) at 50° C. and the reaction mixture was heated at 50° C. overnight. The solvent was then removed under reduced pressure, and the residue was dissolved in dichloromethane (30 mL). The resulting solution was washed with saturated aqueous sodium bicarbonate solution (10 mL), dried over magnesium sulfate, filtered and concentrated under reduced pressure. The crude residue was purified by column chromatography to give the title compound (905 mg, 70% yield).

(b) 3-[4-(Biphenyl-2-ylcarbamoyloxy)piperidin-1-yl]propionic Acid

A stirred solution of the product of Step (a) (902 mg, 2.37 mmol) and lithium hydroxide (171 mg, 7.11 mmol) in a 50% mixture of tetrahydrofuran (12 mL) and water (12 mL) was heated at 30° C. overnight and then acidified with concentrated hydrochloric acid. The resulting'mixture was lyophilized to give the title compound (~100% yield, containing some lithium chloride).

Step 2—Biphenyl-2-ylcarbamic Acid 1-{2-[4-(2-Hydroxyethyl)phenylcarbamoyl]ethyl}-piperidin-4-yl Ester 4-Aminophenethyl alcohol (0.092 mg, 0.67 mmol) (Sigma Aldrich) was added to a solution of the product of Step 1 (226 mg, 0.61 mmol) and N,N-diisopropylethylamine (0.161 mL, 0.67 mmol) in N,N-dimethylformamide (3.3 mL). The resulting mixture was stirred at room temperature for 45 minutes. HATU (257 mg, 0.67 mmol) was then added and the reaction mixture was stirred at room temperature for 12 hours. The reaction mixture was then concentrated under vacuum to half its volume and then diluted with dichloromethane. The organic layer was washed with saturated sodium bicarbonate (2×5 mL) and then with brine (5 mL). The organic layer was dried over magnesium sulfate, filtered, and concentrated to give the title compound (299 mg). MS m/z: [M+H$^+$] calc'd for $C_{29}H_{33}N_3O_4$ 488.3; found 488.3.

Step 3—Biphenyl-2-ylcarbamic Acid 1-{2-[4-(2-Oxoethyl)phenylcarbamoyl]ethyl}-piperidin-4-yl Ester A solution of the product of Step 2 (295 mg, 0.61 mmol) in dichloromethane (3 mL) was cooled to −5° C. in an ice/water bath. Dimethyl sulfoxide (0.258 mL, 0.36 mmol) and N,N-diisopropylethylamine (0.316 mL, 1.8 mmol) were added and the reaction mixture was stirred for 10 minutes at −5° C. Pyridine sulfur trioxide complex (289 mg, 1.8 mmol) was then added with stirring while maintaining the temperature of the reaction mixture at −5° C. After 2 hours, the reaction was complete as determined by MS analysis. The reaction mixture was then quenched with water (5 mL) and the organic layer was washed with water (3×5 mL), dried over magnesium sulfate, filtered, and concentrated to give the title compound (176 mg) as a solid. MS m/z: [M+H$^+$] calc'd for $C_{29}H_{31}N_3O_4$ 486.2; found 486.3.

Alternatively, biphenyl-2-ylcarbamic acid 1-{2-[4-(2-oxoethyl)phenylcarbamoyl]-ethyl}piperidin-4-yl ester can be synthesized by substituting 4-amino phenethyl alcohol for p-aminobenzyl alcohol as the starting material in Example 2, Step 1 and following the synthetic procedures outlined in Example 2, Steps 1 to 3.

Step 4—Biphenyl-2-ylcarbamic Acid 1-[2-(4-{2-[2-(4-Methoxy-2-oxo-2,3-dihydrobenzothiazol-7-yl)-ethylamino]ethyl}phenylcarbamoyl)ethyl]piperidin-4-yl Ester The product of Step 3 (176 mg, 0.36 mmol) was added to a solution of the product of Example 1, Step 4 (106 mg, 0.47 mmol) in dichloromethane (2 mL) and the resulting mixture was stirred at room temperature for 1 hour. Sodium triacetoxyborohydride (84 mg, 0.40 mmol) was added and the resulting mixture was stirred at room temperature for 2 hours. The reaction mixture was quenched with 6 N ammonium chloride (5 mL). The organic layer was separated and washed with saturated sodium bicarbonate (2×5 mL) and then with brine (5 mL). The organic layer was dried over magnesium sulfate, filtered, and concentrated to give the title compound as a solid (207 mg). MS m/z: [M+H$^+$] calc'd for $C_{39}H_{43}N_5O_5S$ 694.3; found 694.3.

Step 5—Biphenyl-2-ylcarbamic Acid 1-[2-(4-{2-[2-(4-Hydroxy-2-oxo-2,3-dihydrobenzothiazol-7-yl)-ethylamino]ethyl}phenylcarbamoyl)ethyl]piperidin-4-yl Ester Bis(trifluoroacetate) Salt A solution of the product of Step 4 (207 mg, 0.30 mmol) in dichloromethane (1.5 mL) was cooled to 5° C. in an ice/water bath. After about 10 minutes, a 1.0 M solution of boron tribromide in dichloromethane (0.90 mL, 0.90 mmol) was added to the reaction mixture. After about 5.5 hours, the reaction mixture was removed from the ice bath and stirred at room temperature. After 12 hours, the reaction mixture was concentrated to dryness and purified by HPLC to give the title compound (8 mg, 99% purity) as a bis(trifluoroacetic) acid salt. MS m/z: [M+H$^+$] calc'd for $C_{38}H_{41}N_5O_5S$ 680.3; found 680.0.

Additionally, other compounds of this invention can be prepared using the following intermediates.

Preparation 1

N-1,1'-Biphenyl-2-yl-N'-4-[1-(9-hydroxynonyl)]piperidinylurea

9-Bromo-1-nonanol (4.84 g, 21.7 mmol) was added to a stirred solution of the product of Example 3, Step 1 (5.8 g, 19.7 mmol) and diisopropylethylamine (10.29 mL, 59.1 mmol) in acetonitrile (99 mL) at 50° C. The reaction mixture was heated at 50° C. for 8 h. The reaction mixture was then allowed to cool and the solvent was removed under reduced pressure. The residue was dissolved in dichloromethane (100 mL), washed with saturated aqueous sodium bicarbonate (2×50 mL) and dried (magnesium sulfate). The solvent was removed under reduced pressure. The crude product was purified by flash chromatography (dichloromethane:methanol: ammonia system) to yield the title compound (7.1 g, 16.2 mmol, 82% yield).

Preparation 2

N-1,1'Biphenyl-2-yl-N'-4-[1-(9-oxononyl)]piperidinylurea

Dimethyl sulfoxide (490 μL, 6.9 mmol), followed by diisopropylethylamine (324 μL, 3.45 mmol) was added to a solution of the product of Preparation 1 (500 mg, 1.15 mmol) in dichloromethane (11.5 mL) at −10° C. under an atmosphere of nitrogen. The reaction mixture was stirred at −15° C. for 15 min, and then sulfur trioxide pyridine complex was added portionwise (549 mg, 3.45 mmol). The reaction mixture was stirred at −15° C. for 1 h, and then water (10 mL) was added. The organic phase was then separated, washed with water (10 mL), and dried (sodium sulfate). The solvent was removed under reduced pressure to give the title compound (475 mg, 1.09 mmol, 95% yield). HPLC (10-70) $R_t$=3.39.

Preparation 3

N,N-(Di-tert-butoxycarbonyl)-9-bromononylamine

A solution of di-tert-butoxycarbonylamine (3.15 g, 14.5 mmol) in N,N-dimethylformamide (0.28 mL) was cooled to 0° C. for about 10 min. Sodium hydride, 60% in mineral oil (0.58 g, 14.5 mmol) was added and the reaction mixture was stirred at 0° C. for 10 min. The reaction mixture was removed from the ice bath and allowed to warm to room temperature for about 30 min. The reaction mixture was then cooled back down to 0° C. and a solution of 1,9-dibromononane (2.46 mL, 12.1 mmol) in dimethylformamide (100 mL) was added. The reaction mixture was stirred overnight at room temperature. After 24 h, MS analysis showed that the reaction was completed. The reaction mixture was concentrated to dryness and diluted with ethyl acetate (100 mL). The organic layer was washed with saturated sodium bicarbonate (2×100 mL), brine (100 mL), dried (magnesium sulfate) and concentrated under reduced pressure to yield the crude product, which was purified by chromatography on silica gel using 5% ethyl acetate in hexanes to afford the title compound. MS m/z: [M+H$^+$] calcd for $C_{19}H_{36}N_1O_4Br$ 423.18; found 423.

Preparation 4

Biphenyl-2-ylcarbamic Acid 1-(9-Di-tert-butoxycarbonylamino)nonyl]piperidin-4-yl Ester A mixture of 1:1 acetonitrile and N,N-dimethylformamide (50 mL) was added to the products of Example 1, Step 1 (3.0 g, 10.1 mmol) and Preparation 3 (5.1 g, 12.2 mmol) and triethylamine (1.42 mL, 10.1 mmol). The reaction mixture was stirred at ambient temperature for 24 h and was monitored by LCMS analysis. The reaction mixture was then concentrated and diluted with ethyl acetate (50 mL). The organic layer was washed with saturated sodium bicarbonate (2×50 mL) and brine (50 mL) The organic phase was then dried over magnesium sulfate and concentrated to yield 6.5 g of crude oil. The oil was purified by chromatography on silica gel using 1:1 hexanes/ethyl acetate to provide the title compound (3 g). MS m/z: [M+H$^+$] calcd for $C_{37}H_{55}N_3O_6$ 638.41; found 639.

Preparation 5

Biphenyl-2-ylcarbamic Acid 1-(9-Aminononyl)piperidin-4-yl Ester

Trifluoroacetic acid (11 mL) was added to a solution of the product of Preparation 4 (7.2 g, 11.3 mmol) in dichloromethane (56 mL) After 2 h, LCMS analysis showed that the reaction was completed. The reaction mixture was then concentrated to dryness and diluted with ethyl acetate (75 mL). Sodium hydroxide (1N) was then added until the pH of the mixture reached 14. The organic phase was then collected and washed with saturated sodium bicarbonate (2×50 mL) and brine (50 mL). The organic phase was then dried over magnesium sulfate and concentrated to provide the title compound (5.5 g). MS m/z: [M+H$^+$] calcd for $C_{27}H_{39}N_3O_2$ 438.30; found 439.

Preparation 6

Biphenyl-2-ylcarbamic Acid 1-(9-Oxononyl)piperidin-4-yl Ester (a) 9-Bromononanal To a 100-mL round-bottomed flask equipped with a magnetic stirrer, addition funnel and temperature controller, under nitrogen, was added 9-bromononanol (8.92 g, 40 mmol) and dichloromethane (30 mL). The resulting mixture was cooled to 5° C. and a solution of sodium bicarbonate (0.47 g, 5.6 mmol) and potassium bromide (0.48 g, 4 mmol) in water (10 mL) was added. 2,2,6,6-Tetramethyl-1-piperidinyloxy free radical (TEMPO) (63 mg, 0.4 mmol) was added and then a 10 to 13% bleach solution (27 mL) was added dropwise through the addition funnel at a rate such that the temperature was maintained at about 8° C. (+/−2° C.) with an ice cold bath (over about 40 min.). After addition of the bleach was complete, the mixture was stirred for 30 min. while maintaining the temperature at about 0° C. A solution of sodium bisulfite (1.54 g) in water (10 mL) was added and the resulting mixture was stirred at room temperature for 30 min. The layers of the mixture were then separated, and the milky aqueous layer was extracted with dichloromethane (1×20 mL) The combined dichloromethane layers were then washed with water (1×30 mL), dried (MgSO$_4$), filtered and concentrated under reduced pressure to afford the title intermediate (8.3 g, 94% yield), which was used without further purification in the next step.

(b) 9-Bromo-1,1-dimethoxynonane

To a 100 mL round-bottomed flask was added 9-bromononanal (7.2 g, 32.5 mmol), methanol (30 mL) and trimethylorthoformate (4 mL, 36.5 mmol). A solution of 4 N hydrochloric acid in dioxane (0.2 mL, 0.8 mmol) was added and the resulting mixture was refluxed for 3 h. The reaction mixture was then cooled to room temperature and solid sodium bicarbonate (100 mg, 1.2 mmol) was added. The resulting mixture was concentrated to one-fourth its original volume under reduced pressure and then ethyl acetate (50 mL) was added. The organic layer was washed with water (2×40 mL), dried (MgSO$_4$), filtered and concentrated under reduced pressure to afford the title intermediate (8.44 g, (97% yield)) as a liquid, which as used in the next step without further purification.

(c) Biphenyl-2-ylcarbamic Acid 1-(9,9-Dimethoxynonyl) piperidin-4-yl Ester

To a 50 mL three-necked, round-bottomed flask was added biphenyl-2-ylcarbamic acid piperidin-4-yl ester (1 g, 3.38 mmol) and acetonitrile (10 mL) to form a slurry. To this slurry was added 9-bromo-1,1-dimethoxynonane (1.1 g, 1.3 mmol) and triethylamine (0.57 g, 4.1 mmol) and the resulting mixture was heated at 65° C. for 6 h (the reaction was monitored by HPLC until starting material is <5%). The reaction mixture was then cooled to room temperature at which time the mixture formed a thick slurry. Water (5 mL) was added and the mixture was filtered to collect the solid on a coarse fritted glass filer. The solid was washed with pre-mixed solution of acetonitrile (10 mL) and water (5 mL) and then with another pre-mixed solution of acetonitrile (10 mL) and water (2 mL). The resulting solid was air dried to afford the title intermediate (1.37 g, 84%, purity>96% by LC, $^1$H NMR) as a white solid.

(d) Biphenyl-2-ylcarbamic Acid 1-(9-Oxononyl)piperidin-4-yl Ester

To a 500 mL round-bottomed flask with a magnetic stirrer was added biphenyl-2-ylcarbamic acid 1-(9,9-dimethoxynonyl)piperidin-4-yl ester (7.7 g, 15.9 mmol) and then acetonitrile (70 mL) and aqueous 1M hydrochloric acid (70 mL). The resulting mixture was stirred at room temperature for 1 h and then dichloromethane (200 mL) was added. This mixture was stirred for 15 min. and then the layers were separated. The organic layer was dried (MgSO$_4$), filtered and concentrated under reduced pressure to afford the title intermediate (6.8 g).

Preparation 7

2-(N-Benzyloxycarbonyl-N-methylamino)ethanal (a) 2-(N-Benzyloxycarbonyl-N-methylamino)ethanol Benzyl chloroformate (19 g, 111.1 mmol) in THF (20 mL) was added dropwise over 15 min to a stirred solution of 2-(methylamino)ethanol (10 g, 133.3 mmol) in THF (100 mL) and aqueous sodium carbonate (100 mL) at 0° C. The reaction mixture was stirred at 0° C. for 12 h and then extracted with EtOAc (2×200 mL). The organic layer was washed with aqueous sodium carbonate (200 mL) and dried (potassium carbonate) and solvent was removed under reduced pressure to give the title compound (22.5 g, 97% yield).

(b) 2-(N-Benzyloxycarbonyl-N-methylamino)ethanal

DMSO (71 mL, 1 mol) and DIPEA (87.1 mL, 0.5 mol) were added to a stirred solution of the product of step (a) (20.9 g, 0.1 mol) in dichloromethane (200 mL) at −10° C. The reaction mixture was stirred at −10° C. for 15 min and then sulfur trioxide pyridine complex (79.6 g, 0.5 mol) was added and the resulting mixture was stirred for 1 hour. The reaction mixture was quenched with addition of 1M hydrochloric acid (200 mL). The organic layer was separated and washed with saturated aqueous sodium bicarbonate (100 mL), brine (100 mL), dried (potassium carbonate) and solvent removed under reduced pressure to give the title compound (20.7 g, ~100% yield).

Preparation 8

Biphenyl-2-ylcarbamic Acid
1-[2-(Methylamino)ethyl]piperidin-4-yl Ester

To a stirred solution of the product of Preparation 7 (20.7 g, 100 mmol) and the product of Example 1, Step 1 (25 g, 84.7 mmol) in MeOH (200 mL) was added sodium triacetoxyborohydride (21.2 g, 100 mmol). The reaction mixture was stirred for 12 h at ambient temperature and then it was quenched with 2M hydrochloric acid and the solvent was removed under reduced pressure. The residue was dissolved in ethyl acetate (200 mL) and washed with saturated aqueous sodium bicarbonate solution (100 mL) and brine (50 mL), and then dried (magnesium sulfate) and the solvent was removed under reduced pressure. The crude residue was purified by column chromatography (50-90% EtOAc/hexanes) to give biphenyl-2-ylcarbamic acid 1-[2-(benzyloxycarbonyl-methylamino)ethyl]piperidin-4-yl ester as an oil.

The oil was dissolved in methanol (100 mL) and palladium (10 wt. % (dry basis) on activated carbon) (5 g) was added. The reaction mixture was stirred under hydrogen (30 psi) for 12 h and then filtered through Celite, which was washed with methanol, and solvent was evaporated to give the title compound (13.2 g, 44% yield).

Preparation 9

Biphenyl-2-ylcarbamic Acid 1-{2-[(6-Bromohexanoyl)methylamino]ethyl}piperidin-4-yl Ester 6-Bromohexanoyl chloride (3.23 mL, 21.1 mmol) was added to a stirred solution of the product of Preparation 8 (6.2 g, 17.6 mmol) and DIPEA (6.13 mL, 35.2 mmol) in dichloroethane (170 mL). The reaction mixture was stirred for 1 hour and it was then diluted with EtOAc (250 mL) and washed with saturated aqueous sodium bicarbonate solution (2×200 mL) and brine (200 mL), and then dried (magnesium sulfate). The solvent was removed under reduced pressure to give the title compound (6.6 g, 73% yield).

Preparation 10

Biphenyl-2-ylcarbamic Acid 1-[2-(4-(Aminomethyl) phenylcarbamoyl)-ethyl]piperidin-4-yl Ester To a stirred solution of 4-(N-tert-butoxycarbonylaminomethyl)aniline (756 mg, 3.4 mmol), the product of Example 4, Step 1 (1.5 g, 4.08 mmol) and HATU (1.55 g, 4.08 mmol) in DMF (6.8 mL) was added DIPEA (770 µL, 4.42 mmol). The reaction mixture was stirred at 50° C. overnight and then the solvent was removed under reduced pressure. The resulting residue was dissolved in dichloromethane (20 mL) and washed with saturated aqueous sodium bicarbonate solution (10 mL). The organic phase was then dried (magnesium sulfate) and the solvent was removed under reduced pressure. The crude product was purified by flash chromatography (5-10% MeOH/DCM) to give a solid, which was dissolved in TFA/DCM (25%, 30 mL) and stirred at room temperature for 2 h. The solvent was then removed under reduced pressure and the crude residue was dissolved in dichloromethane (30 mL) and washed with 1N sodium hydroxide (15 mL) The organic phase was separated, dried (magnesium sulfate) and the solvent was removed under reduced pressure to give the title compound (1.5 g, 94% over 2 steps).

Preparation 11

Biphenyl-2-ylcarbamic Acid
1-(2-tert-Butoxycarbonylaminoethyl)piperidin-4-yl
Ester To a stirred solution of the product of Example 1, Step 1 8 (2.00 g, 6.76 mmol) and DIPEA (3.54 mL, 20.3 mmol) in acetonitrile (67.6 mL) at 50° C. was added 2-tert-butoxycarbonylaminoethyl bromide (1.82 g, 8.11 mmol) and the reaction mixture was heated at 50° C. overnight. The solvent was then removed under reduced pressure and the residue was dissolved in dichloromethane (60 mL) and washed with saturated aqueous sodium bicarbonate solution (30 mL). The organic phase was dried (magnesium sulfate) and the solvent was removed under reduced pressure. The crude residue was purified by column chromatography (5% MeOH/DCM) to yield the title compound as a solid (2.32 g, 78% yield).

Preparation 12

Biphenyl-2-ylcarbamic Acid 1-(2-Aminoethyl)piperidin-4-yl Ester

The product of Preparation 11 was dissolved in TFA/DCM (25%, 52 mL) and stirred at room temperature for 2 h. The solvent was then removed under reduced pressure and the crude residue dissolved in dichloromethane (30 mL) and washed with 1N sodium hydroxide (15 mL). The organic phase was separated, dried (magnesium sulfate) and the solvent was removed under reduced pressure to give the title compound (1.61 g, 90% yield).

Preparation 13

Biphenyl-2-ylcarbamic Acid 1-[2-(4-Aminomethyl-benzoylamino)ethyl]piperidin-4-yl Ester To a stirred solution of the product of Preparation 12 (339 mg, 1 mmol), 4-(tert-butoxycarbonylaminomethyl)benzoic acid (301 mg, 1.2 mmol) and HATU (456 mg, 1.2 mmol) in DMF (2 mL) was added DIPEA (226 μL, 1.3 mmol). The reaction mixture was stirred at room temperature overnight and then the solvent was removed under reduced pressure. The resulting residue was dissolved in dichloromethane (20 mL) and washed with saturated aqueous sodium bicarbonate solution (10 mL). The organic phase was dried (magnesium sulfate) and the solvent was removed under reduced pressure. The crude product was dissolved in TFA/DCM (25%, 10 mL) and this mixture was stirred at room temperature for 2 h. The solvent was removed under reduced pressure and the crude residue was dissolved in dichloromethane (15 mL) and washed with 1N sodium hydroxide (5 mL). The organic phase was separated, dried (magnesium sulfate) and the solvent was removed under reduced pressure to afford the title compound (472 mg, ~100% over 2 steps).

Preparation 14

Biphenyl-2-ylcarbamic Acid 1-(2-Aminoethyl)piperidin-4-yl Ester 2-tert-Butoxycarbonylaminoethyl bromide (1.22 g, 5.44 mmol) was added to a solution of the product of Example 1, Step 1 (1.46 g, 4.95 mmol) and diisopropylethylamine (1.03 mL, 5.94 mmol) in acetonitrile (24 mL). The reaction mixture was stirred at 65° C. for 12 hours, at which time MS analysis showed that the reaction was completed. The reaction mixture was concentrated to dryness and then dichloromethane (10 mL) was added. Trifluoroacetic acid was added to this mixture and the mixture was stirred at room temperature for 4 hours, at which time MS analysis showed that the reaction was complete. The mixture was then concentrated to half its volume and 1N sodium hydroxide was added to the solution until the pH was adjusted to 14. The organic layer was washed with brine, then dried over magnesium sulfate and filtered. The filtrate was concentrated to give 1.6 g of the title compound as a solid. MS m/z: [M+H$^+$] calcd for $C_{20}H_{25}N_3O_2$ 340.2; found 340.

Preparation 15

1-[1-(9-Benzylaminononyl)piperidin-4-yl]-3-biphenyl-2-ylurea

N-Benzylamine (0.903 ml, 8.30 mmol) was added to a solution of the product of Preparation 2 (2.40 g, 5.52 mmol) in methanol (25 mL) and the resulting mixture was stirred at ambient temperature. After 10 min, sodium triacetoxyborohydride (1.75 g, 8.30 mmol) was added to the reaction mixture. The progress of the reaction was followed by HPLC analysis. After 2 h at ambient temperature, the reaction was quenched with water (5 mL) and then concentrated to half its volume under vacuum. The reaction mixture was diluted with dichloromethane (15 mL) and washed with 1N sodium hydroxide (2×10 mL) and then brine (5 mL). The organic layer was dried over magnesium sulfate and concentrated to yield the title compound.

Preparation 16

2-Benzyloxy-5-(2-bromoacetyl)benzoic Acid Methyl Ester (a) 2-Benzyloxy-5-acetylbenzoic Acid Methyl Ester Methyl 5-acetylsalicylate (100 g, 0.515 mol) was dissolved in acetonitrile (1 L) in a 2 L flask under reflux conditions and a nitrogen atmosphere. Potassium carbonate (213.5 g, 1.545 mol) was added portion-wise over 15 min. Benzyl bromide (67.4 mL, 0.566 mol) was added using a dropping funnel over 15 min. The reaction was heated to 85° C. for 9 h, and then filtered and rinsed with acetonitrile (100 mL). The solution was concentrated to about 300 mL volume under reduced pressure and partitioned between water (1 L) and ethyl acetate (1 L). The organic layer was washed with saturated sodium chloride (250 mL), dried using magnesium sulfate (75 g), and then filtered and rinsed with ethyl acetate (100 mL). The organic layer was concentrated to give 2-benzyloxy-5-acetylbenzoic acid methyl ester as a solid (100% yield).

(b) 2-Benzyloxy-5-(2-bromoacetyl)benzoic Acid Methyl Ester

The product of step (a) (10.0 g, 35.2 mmol) was dissolved in chloroform (250 mL) in a 500 mL flask under a nitrogen atmosphere. Bromine (1.63 mL, 31.7 mmol) dissolved in chloroform (50 mL) was added using a dropping funnel over 30 min. The reaction mixture was stirred for 2.5 h and then concentrated to give a solid. The solid was dissolved in toluene (150 mL) with some gentle heat, followed by the addition of ethyl ether (150 mL) to yield the title compound as a crystalline solid (55% yield).

Preparation 17

5-[2-(Benzyl-{9-[4-(3-biphenyl-2-ylureido)piperidin-1-yl]nonyl}amino)acetyl]-2-benzyloxybenzoic Acid Methyl Ester The product of Preparation 16 (371 mg, 1.00 mmol) was added to a solution of the product of Preparation 15 (448 mg, 0.85 mmol) in dimethyl sulfoxide (4.5 mL) followed by the addition of potassium carbonate (234 mg, 1.7 mmol). The reaction mixture was stirred at 40° C. for 6 h, at which time the product of Preparation 15 was no longer observed by HPLC analysis. The reaction mixture was cooled to ambient temperature and filtered, and then diluted with ethanol (4 mL). Sodium borohydride (63 mg, 1.7 mmol) was added to the reaction mixture and the reaction was stirred at ambient temperature for 24 h. The reaction mixture was quenched with 0.5 M ammonium chloride (5 mL) and extracted into ethyl acetate (2×10 mL). The combined organic layers were washed with saturated sodium bicarbonate (10 mL) and then with brine (5 mL). The organic layer was dried over magnesium sulfate and the solvent was removed under reduced pressure. The crude residue was purified by chromatography on silica gel (3% methanol in chloroform) to give the title compound.

Preparation 18

1-[1-(9-{Benzyl-[2-(4-benzyloxy-3-hydroxymethylphenyl)-2-hydroxyethyl]amino}nonyl)piperidin-4-yl]-3-biphenyl-2-ylurea A solution of the product of Preparation 17 (163 mg, 0.20 mmol) in tetrahydrofuran (1.00 mL) was cooled to 0° C. Lithium aluminium hydride (1.0 M in THF; 0.50 mL, 0.50 mmol) was added dropwise to the mixture. After 1 h, the reaction mixture was quenched with water (1 mL) and diluted with ethyl acetate (2 mL). The organic layer was washed with brine, dried over magnesium sulfate, and the organic extracts were combined and concentrated to give the title compound.

Preparation 19

Biphenyl-2-ylcarbamic Acid 1-{2-[((1R,3S)-3-Aminocyclopentanecarbonyl)amino]-ethyl}piperidin-4-yl Ester To a stirred solution of the product of Preparation 14 (318 mg, 0.94 mmol), (1R,3S)-3-tert-butoxycarbonylaminocyclopentanecarboxylic acid (258 mg, 1.1 mmol) and HATU (428 mg, 1.1 mmol) in DMF (5 mL) was added DIPEA (245 µL, 1.09 mmol). The reaction mixture was stirred at room temperature overnight and then the solvent was removed under reduced pressure. The resulting residue was dissolved in dichloromethane (20 mL) and washed with saturated aqueous sodium bicarbonate solution (10 mL). The organic layer was dried (magnesium sulfate) and the solvent was removed under reduced pressure. The crude product was purified by flash chromatography (5-10% MeOH/DCM) and then dissolved in a trifluoroacetic acid/DCM mixture (1 mL/5 mL) and stirred at room temperature for 1 h. The solvent was removed under reduced pressure. The residue was dissolved in dichloromethane (20 mL) and washed with 1M sodium hydroxide (10 mL), dried (magnesium sulfate) and the solvent reduced to yield the title compound (167 mg, 39% yield).

Preparation 20

4-(tert-Butoxycarbonylaminomethyl)-2-chlorophenylamine

A stirred solution of 4-aminomethyl-2-chlorophenylamine (940 mg, 6 mmol) and di-tert-butyl dicarbonate (1.44 g, 6.6 mmol) in dichloromethane (30 mL) was stirred at room temperature for 4 h, at which time the reaction was determined to be complete by LCMS. The reaction mixture was then washed with saturated aqueous sodium bicarbonate (15 mL) and the organic layer was dried over sodium sulfate and the solvent was removed under reduced pressure. The resulting orange solid was recrystallized from ethyl acetate to give the title intermediate as a white solid (~100% yield).

Preparation 21

N-[4-(tert-Butoxycarbonylaminomethyl)-2-chlorophenyl]acrylamide

To a stirred solution of the product of Preparation 20 (1.54 g, 6.0 mmol) in a mixture of diethyl ether (35 mL) and 1 M sodium hydroxide (35 mL) was added dropwise acryloyl chloride (687 µL, 8.45 mmol). After 1 h, the organic layer was separated, dried ($Na_2SO_4$) and the solvent was removed under reduced pressure to give the title intermediate as a white solid (1.8 g, 96% yield).

Preparation 22

Biphenyl-2-ylcarbamic Acid 1-[2-(4-(tert-Butoxycarbonylaminomethyl)-2-chlorophenylcarbamoyl)ethyl]piperidin-4-yl Ester A solution of the product of Example 1, Step 1 (1.04 g, 3.5 mmol) and the product of Preparation 21 (1.19 g, 3.85 mmol) in a mixture of dichloromethane and methanol (12 mL, 1:1) was heated at 60° C. for 12 h. The reaction mixture was allowed to cool and the solvent was removed under reduced pressure. The crude material was purified by column chromatography (5-10% MeOH/DCM) to give the title intermediate as a white solid (2.00 g, 94% yield).

Preparation 23

Biphenyl-2-ylcarbamic Acid 1-[2-(4-Aminomethyl-2-chlorophenylcarbamoyl)ethyl]-piperidin-4-yl Ester A solution of the product of Preparation 22 (2.00 g, 3.3 mmol) was stirred in dichloromethane (24 mL) and TFA (8 mL) for 1 h and then the solvent was removed under reduced pressure. The crude reaction mixture was dissolved in dichloromethane (30 mL) and washed with 1 M sodium hydroxide (2×30 mL). The organic layer was dried ($Na_2SO_4$) and the solvent was removed under reduced pressure to give the title intermediate as an oily white solid (1.46 g, 88% yield).

Preparation 24

2-Chloroethanesulfonic Acid (5-tert-Butoxycarbonylaminopentyl)amide

To a stirred solution of 5-(tert-butoxycarbonylamino)pentylamine (1.00 g, 4.94 mmol) and triethylamine (689 µL g, 4.94 mmol) in dichloromethane (22 mL) at 0° C. was added 2-chloro-1-ethanesulfonyl chloride (470 µL, 4.50 mmol). The reaction mixture was stirred for 2 h at room temperature and then washed with saturated aqueous sodium bicarbonate solution (15 mL). The organic layer was dried ($Na_2SO_4$) and the solvent was removed under reduced pressure to give the title compound (100% yield), which was used in the next step without further purification.

Preparation 25

Biphenyl-2-ylcarbamic Acid 1-[2-(5-tert-Butoxycarbonylaminopentylsulfamoyl)-ethyl]piperidin-4-yl Ester A solution of the product of Example 1, Step 1 (1.33 g, 3.5 mmol) and the product of Preparation 24 (1.62 g, 4.94 mmol) in dichloromethane and methanol (22 mL, 1:1) was heated at 60° C. for 5 h. The reaction mixture was allowed to cool to room temperature and the solvent was removed under reduced pressure. The crude residue was dissolved in dichloromethane (20 mL) and washed with saturated aqueous sodium bicarbonate solution (10 mL). The organic layer was then dried ($Na_2SO_4$) and solvent removed under reduced pressure. The crude residue was purified by column chromatography (5-10% MeOH/DCM) to give the title intermediate as a white solid (1.6 g, 55%). MS m/z M+H$^+$=589.6.

Preparation 26

Biphenyl-2-ylcarbamic Acid 1-[2-(5-Aminopentylsulfamoyl)ethyl]piperidin-4-yl Ester A solution of the product of Preparation 25 (1.6 g, 2.72 mmol) was stirred in dichloromethane (21 mL) and TFA (7 mL) for 1 h and then the solvent was removed under reduced pressure. The crude reaction mixture was dissolved in dichloromethane (30 mL) and washed with 1 M sodium hydroxide (2×30 mL). The organic layer was dried ($Na_2SO_4$) and the solvent was then removed under reduced pressure to give the title intermediate as an oily white solid (1.19 g, 90% yield).

Preparation 27

Biphenyl-2-ylcarbamic Acid 1-{2-[(4-Formylbenzenesulfonyl)methylamino]-ethyl}piperidin-4-yl Ester To a stirred solution of the product of Preparation 8 (350 mg, 1 mmol) and triethylamine (167 μL, 1.2 mmol) in dichloromethane (5 mL) was added 4-formylbenzenesulfonyl chloride (225 mg, 1.1 mmol). After 1 h at room temperature, the reaction was complete by MS and the reaction mixture was then washed with saturated aqueous sodium bicarbonate solution (5 mL). The organic layer was then dried ($Na_2SO_4$) and solvent removed under reduced pressure to give the title intermediate (323 mg, 62% yield). MS m/z $M+H^+$=522.4.

Preparation 28

(3-Aminomethylphenyl)methanol Hydrochloride (a) (3-tert-Butoxycarbonylmethylphenyl)methanol
Borane dimethyl sulfide (2.05 mL, 21.6 mmol) was added to a solution of 3-(tert-butoxycarbonylaminomethyl)benzoic acid (1.81 g, 7.20 mmol) in tetrahydrofuran (24 mL). and the resulting mixture was stirred at room temperature for 3 hours. The reaction mixture was then diluted with ethyl acetate (20 mL) and the layers were separated. The organic layer was washed with saturated sodium bicarbonate, saturated sodium chloride, dried over magnesium sulfate and concentrated to give the title compound as a yellow oil (1.71 g).

(b) (3-Aminomethylphenyl)methanol Hydrochloride
To the product of step (a) (1.71 g, 7.2 mmol) was added a solution of 4 M hydrochloric acid in dioxane (9 mL, 36 mmol) and the resulting mixture was stirred at room temperature for 1 h. The reaction mixture was then concentrated and the residue was diluted with diethyl ether (50 mL) and filtered to provide the title compound as a white solid (1.09 g).

Preparation 29

Biphenyl-2-ylcarbamic Acid 1-{2-[3-(3-Hydroxymethylbenzyl)ureido]ethyl}piperidin-4-yl Ester A 0.2 M solution of the product of Preparation 12 (760 mg, 2.24 mmol) in N,N-dimethylformamide was added dropwise to a solution of 1,1'-carbonyldiimidazole (364 mg, 2.24 mmol) and diisopropylethylamine (0.31 mL, 2.24 mmol) in N,N-dimethylformamide (11 mL) and the resulting mixture was stirred at room temperature for 2 h. Diisopropylethylamine (0.31 mL, 2.24 mmol) and the product of Preparation 28 (578 mg, 3.4 mmol) were added and this mixture was stirred at 50° C. for 12 hours. The reaction mixture was then concentrated to dryness and the residue was diluted with dichloromethane (20 mL) and this solution was washed with saturated sodium bicarbonate (2×), saturated sodium chloride, dried over magnesium sulfate, and concentrated to provide the title compound (1.12 g). LCMS (2-90) $R_f$=4.01 min.; MS m/z M+H=503.5.

Preparation 30

Biphenyl-2-ylcarbamic Acid 1-{2-[3-(3-Formylbenzyl)ureido]ethyl}piperidin-4-yl Ester A solution of the product of Preparation 29 (1.12 g, 2.23 mmol) in dichloromethane (11.1 mL) was cooled to 0° C. and diisopropylethylamine (1.17 mL, 6.70 mmol) and dimethyl sulfoxide (0.949 mL, 13.4 mmol) were added. After about 10 minutes, pyridine sulfur trioxide complex (1.06 g, 6.70 mmol) was added and the resulting mixture was stirred at 0° C. for 2 h. The reaction was then quenched with water (15 mL) and the organic layer was washed with cold water (3×), dried over magnesium sulfate and concentrated to provide the title compound as a yellow crisp (609 mg). LCMS (2-90) $R_f$=4.13 min; MS m/z M+H=501.3.

Preparation 31

Biphenyl-2-ylcarbamic Acid 1-[(E)-3-(4-Nitrophenyl)allyl]piperidin-4-yl Ester

The product of Example 1, Step 1 (2.96 g, 0.01 mol) and p-nitrocinnamaldehyde (1.77 g, 0.01 mol) were stirred in 50 mL of dichloromethane for 2 h. Sodium triacetoxyborohydride (6.33 g, 0.03 mol) was added and the resulting mixture was stirred for 2 h. The reaction was then quenched with 10 mL of water and this mixture was diluted with dichloromethane (100 mL). The organic layer was washed with saturated sodium bicarbonate (2×), brine, dried over $Na_2SO_4$, filtered and concentrated to provide the title compound as a yellow foam (3.8 g, 80% yield).

Preparation 32

Biphenyl-2-ylcarbamic Acid 1-[3-(4-Aminophenyl)propyl]piperidin-4-yl Ester

The product of Preparation 31 (2.5 g, 5.4 mmol) was dissolved in 100 mL of ethanol and the resulting solution was purged with nitrogen for 30 min. Palladium on carbon (2.5 g; 50% w/w water; 10% Pd; 1.1 mmol Pd) was then added while degassing with nitrogen. This mixture was then placed under hydrogen (50 psi) until hydrogen was no longer consumed (~30 minutes). The mixture was then purged with nitrogen, filtered through Celite and concentrated. The residue was dissolved in ethyl acetate and this mixture was washed with saturated sodium bicarbonate (2×), brine, dried ($Na_2SO_4$), filtered and concentrated to provide the title compound (2.08 g, 90% yield). MS m/z M+H=430.5.

Preparation 33

Biphenyl-2-ylcarbamic Acid 1-[2-Fluoro-3-(4-hydroxymethylpiperidin-1-ylmethyl)-benzyl]piperidin-4-yl Ester The product of Example 1, Step 1 (500 mg, 1.69 mmol), 2,6-bis(bromomethyl)-1-fluorobenzene (476 mg, 1.69 mmol, piperidin-4-ylmethanol (195 mg, 1.69 mmol) and potassium carbonate (466 mg, 3.37 mmol) were suspended in acetonitrile (5 mL) and stirred at room temperature for 18 h. The reaction mixture was then concentrated and the residue was dissolved in dichloromethane/water. The layers were separated and the organic layer was washed with water (2×), brine, dried ($MgSO_4$) and concentrated. The crude material was purified by silica gel column chromatography eluting with 3% methanol/chloroform to give the title compound as a white foam (282 mg). MS m/z M+H=532.3.

Preparation 34

Biphenyl-2-ylcarbamic Acid 1-[2-Fluoro-3-(4-formylpiperidin-1-ylmethyl)benzyl]-piperidin-4-yl Ester The product of Preparation 33 (282 mg, 0.53 mmol) was dissolved in dichloromethane and to this mixture was added diisopropylethylamine (280 µL, 1.6 mmol) and dimethyl sulfoxide (115 µL, 1.6 mmol). The reaction mixture was cooled to −15° C. under nitrogen and pyridine sulfur trioxide complex (255 mg, 1.6 mmol) was added and the resulting mixture was stirred for 40 min. The reaction was then quenched with water and the layers were separated. The organic layer was washed with aqueous $NaH_2PO_4$ (1M×3), brine, dried ($MgSO_4$) and concentrated to provide the title compound as a foam (253 mg). MS m/z M+H=530.4.

Preparation 35

2-[4-(3-Bromopropoxy)phenyl]ethanol

To a solution of 4-hydroxyphenethyl alcohol (4.37 g, 31.0 mmol) and potassium carbonate (6.55 g, 47.0 mmol) in acetonitrile (62.0 mL) was added 1,3 dibromopropane (31.0 mL, 316 mmol). The reaction mixture was heated to 70° C. for 12 hours and then cooled to room temperature, filtered and concentrated under vacuum. The resulting oil was purified by silica gel chromatography using a mixture of 4:1 hexanes and ethyl acetate to give the title compound (6.21 g) as a white solid.

Preparation 36

Biphenyl-2-ylcarbamic Acid 1-{3-[4-(2-Hydroxy-ethyl)phenoxy]propyl}piperidin-4-yl Ester To a solution of the product of Preparation 35 (1.11 g, 4.30 mmol) and diisopropylethylamine (0.90 mL, 5.10 mmol) in acetonitrile (21.5 mL) was added the product of Example 1, Step 1 (1.27 g, 4.30 mmol) and the resulting mixture was stirred at 60° C. for 12 h. The reaction mixture was then diluted with dichloromethane (20 mL) and washed with saturated sodium bicarbonate (25 mL), saturated sodium chloride (25 mL), dried over magnesium sulfate and concentrated to provide the title compound (1.98 g, 85% purity). MS m/z M+H=475.5.

Preparation 37

Biphenyl-2-ylcarbamic Acid 1-{3-[4-(2-Oxoethyl)phenoxy]propyl}piperidin-4-yl Ester A solution of the product of Preparation 36 (723 mg, 1.53 mmol) and dichloromethane (75 mL) was cooled to about 5° C. and diisopropylethylamine (798 mL, 4.58 mmol) and dimethyl sulfoxide (649 mL, 9.15 mmol) were added. Pyridine sulfur trioxide (728 mg, 4.58 mmol) was then added and the resulting mixture was stirred at 5° C. for 45 min. The reaction mixture was then diluted with dichloromethane (20 mL) and washed with saturated sodium bicarbonate (25 mL), saturated sodium chloride (25 mL), dried over magnesium sulfate and concentrated to provide the title compound (604 mg). MS m/z M+H=473.4.

Preparation 38

Methyl 4-Iodophenylacetate

To a stirred solution of 4-iodophenylacetic acid (5.0 g, 19.1 mmol) in MeOH (200 mL) was added 4N hydrochloric acid in dioxane (10 mL). The reaction mixture was stirred for 24 h at room temperature and then the solvent was removed under reduced pressure to give the title compound (5.17 g, 98% yield), which was used without further purification.

Preparation 39

Methyl [4-(4-Hydroxybut-1-ynyl)phenyl]acetate

To a stirred solution of the product of Preparation 38 (4.5 g, 16.3 mmol) in diethylamine (100 mL) was added but-3-yn-1-ol (1.9 mL, 32.6 mmol), $Pd(PPh_3)_2Cl_2$ (500 mg, 1.63 mmol) and CuI (154 mg, 0.815 mmol) and resulting mixture was stirred for 17 h at room temperature. The solvent was then removed under reduced pressure and the residue was dissolved in diethyl ether (200 mL) and this solution was filtered to remove salts. The solvent was then removed under reduced pressure and the crude product was purified by silica gel chromatography (60% EtOAc/Hexane) to afford the title intermediate (3.03 g, 91% yield).

Preparation 40

Methyl [4-(4-Hydroxybutyl)phenyl]acetate

A stirred solution of the product of Preparation 39 (2.8 g, 12.8 mmol) in methanol (50 mL) was flushed with nitrogen and then 10% palladium on carbon (400 mg, 20% wt/wt) was added. The reaction flask was then alternately placed under vacuum and flushed with hydrogen for cycles and then stirred under hydrogen for 14 h. The reaction mixture was flushed with nitrogen and then filtered and the solvent removed under reduced pressure to give the title compound (2.75 g, 97% yield), which was used without further purification.

Preparation 41

Methyl (4-{4-[4-(Biphenyl-2-ylcarbamoyloxy)piperidin-1-yl]butyl}phenyl)acetate (a) Methyl {4-[4-(Toluene-4-sulfonyloxy)butyl]phenyl}acetate To a stirred solution of the product of Preparation 40 (2.6 g, 12.5 mmol) in THF (100 mL) was added DABCO (2.6 g, 25.0 mmol) and then p-toluenesulfonyl chloride (2.44 g, 13.75 mmol). The reaction mixture was stirred at room temperature for 23 h and then solvent was removed under reduced pressure and the residue was dissolved in dichloromethane (200 mL). The organic layer was then washed with water (2×100 mL), 1N hydrochloric acid (100 mL), aqueous saturated sodium chloride solution (100 mL), dried ($MgSO_4$), filtered and the solvent removed under reduced pressure to give the title compound, which was used without further purification.

(b) Methyl (4-{4-[4-(Biphenyl-2-ylcarbamoyloxy)piperidin-1-yl]butyl}phenyl)acetate To the crude product from step (a) was added DMF (50 mL), diisopropylethylamine (3.0 mL, 17.3 mmol) and the product of Preparation 8 (2.4 g, 8.1 mmol). The reaction mixture was stirred at room temperature for 18 h and then the solvent was removed under reduced pressure to give the title compound (3.5 g, 86.3% yield). MS m/z 501.6 (MH⁺), $R_f$ 4.89 min (10-70% ACN: $H_2O$, reverse phase HPLC).

Preparation 42

Biphenyl-2-ylcarbamic Acid 1-{4-[4-(2-Hydroxy-ethyl)phenyl]butyl}piperidin-4-yl Ester To a stirred solution of the product of Preparation 41 (2.0 g, 4.0 mmol) in THF (100 mL) was added dropwise DIBAL (24 mL, 24 mmol, 1.0 M in THF). After the addition was complete, the reaction mixture was stirred for 3 h and then quenched by slow addition of methanol (until gas evolution ceased). The mixture was then stirred for 30 min. and then ethyl acetate (200 mL) and aqueous 1N sodium hydroxide (200 mL) were added. The organic layer was separated and washed with aqueous saturated sodium chloride solution (100 mL), dried (MgSO$_4$), filtered and the solvent removed under reduced pressure to give the title compound (1.3 g, 69% yield), which was used without further purification. MS m/z 473.4 (MH$^+$), R$_f$ 4.53 min (10-70% ACN: H$_2$O, reverse phase HPLC).

Preparation 43

Ethyl 3-[5-(2-Ethoxycarbonylvinyl)thiophen-2-yl]acrylate

To a stirred solution of sodium hydride (2.1 g, 53 mmol, 60% in mineral oil) in THF (200 mL) was slowly added triethylphosphonoacetate (10 mL, 50 mmol) Hydrogen gas evolution was observed and the reaction was stirred until gas evolution ceased (about 30 min). To this reaction mixture was added 2,5-thiophenedicarboxaldehyde (3 g, 21 mmol) and the reaction mixture was stirred for 1 h. The solvent was removed under reduced pressure and the residue was dissolved in dichloromethane (200 mL). The organic layer was washed with water (100 mL), aqueous 1N hydrochloric acid (100 mL), aqueous saturated sodium chloride solution (100 mL), dried (MgSO$_4$), filtered and the solvent removed under reduced pressure to give the title compound (5.8 g, 98% yield), which was used without further purification.

Preparation 44

Ethyl 3-[5-(2-Ethoxycarbonylethyl)thiophen-2-yl]propionate

A stirred solution of the product of Preparation 43 (5.8 g, 21 mmol) in methanol (200 mL) was flushed with nitrogen and 10% palladium on carbon (576 mg, 10% wt/wt) was added. The reaction flask was alternately placed under vacuum and flushed with hydrogen for 3 cycles and then the reaction mixture was stirred under hydrogen for 1 h. The mixture was then was flushed with nitrogen, filtered and the solvent removed under reduced pressure to give the title compound (5.8 g, 99% yield), which was used without further purification.

Preparation 45

3-[5-(3-Hydroxypropyl)thiophen-2-yl]propan-1-ol

To a stirred solution of DIBAL (88 mL, 88 mmol, 1.0M in cyclohexane) in THF (300 mL) at −78° C. was added dropwise the product of Preparation 44 (5.0 g, 17.6 mmol). After the addition was complete, the reaction mixture was warmed to room temperature over 30 min and then quenched by slow addition of aqueous 1N hydrochloric acid (200 mL). Dichloromethane (400 mL) was added and the layers were separated. The aqueous layer was washed with dichloromethane (4×100 mL) and the combined organic layers were washed with aqueous saturated sodium chloride solution (100 mL), dried (MgSO$_4$), filtered and the solvent removed under reduced pressure to give the title compound (3.0 g, 85% yield), which was used without further purification.

Preparation 46

Biphenyl-2-ylcarbamic Acid 1-{3-[5-(3-Hydroxypropyl)thiophen-2-yl]propyl}piperidin-4-yl Ester (a) Toluene-4-sulfonic Acid 3-[5-(3-Hydroxypropyl)thiophen-2-yl]propyl Ester
To a stirred solution of the product of Preparation 45 (423 mg, 2.1 mmol) in THF (20 mL) was added DABCO (420 mg, 4.2 mmol) and then p-toluenesulfonyl chloride (442 mg, 2.3 mmol). The reaction mixture was stirred at room temperature for 2 h and then the solvent was removed under reduced pressure and the residue was dissolved in dichloromethane (200 mL). The organic layer was washed with water (2×100 mL), aqueous saturated sodium chloride solution (100 mL), dried MgSO$_4$), filtered and the solvent removed under reduced pressure to give the title compound, which was used without further purification.

(b) Biphenyl-2-ylcarbamic Acid 1-{3-[5-(3-Hydroxypropyl)thiophen-2-yl]propyl}piperidin-4-yl Ester
To the product from step (a) was added acetonitrile (20 mL), diisopropylethylamine (0.5 mL, 2.8 mmol) and the product of Example 1, Step 1 (626 mg, 2.11 mmol). The reaction mixture was heated to 50° C. for 20 h and then cooled to room temperature and the solvent was removed under reduced pressure. The residue was purified by silica gel chromatography (5% MeOH/DCM with 0.6% NH$_3$ (aq)) to afford the title compound (450 mg, 44% yield). MS m/z (MH$^+$) 479.6; R$_f$ 4.15 min (10-70% ACN: H$_2$O, reverse phase HPLC).

Preparation 47

Methyl 4-Amino-5-chloro-2-methoxybenzoate

To a solution of 4-amino-5-chloro-2-methoxybenzoic acid (1.008 g, 5.0 mmol) in a mixture of toluene (9 mL) and methanol (1 mL) at 0° C. was added (trimethylsilyl)diazomethane (2.0 M in hexane, 3.0 mL, 6.0 mmol) dropwise. The reaction mixture was then warmed to room temperature and stirred for 16 h. Excess (trimethylsilyl)diazomethane was quenched by adding acetic acid until the bright yellow color of the reaction mixture disappeared. The mixture was then concentrated in vacuo to give the title compound as an off-white solid, which was used without further purification.

Preparation 48

Methyl 4-Acryloylamino-5-chloro-2-methoxybenzoate

To crude product of Preparation 47 was added dichloromethane (10 mL, 0.5 M) and triethylamine (2.1 mL, 15 mmol). This mixture was cooled to 0° C. and acryloyl chloride (812 µL, 10 mmol) was added dropwise with stirring. After 2 h, the reaction was quenched by adding methanol (about 2 mL) at 0° C. and the resulting mixture was stirred at room temperature for 15 min and then concentrated in vacuo. Dichloromethane (30 mL) and water (30 mL) were added to the residue and this mixture was mixed thoroughly. The layers were separated and the aqueous layer was extracted with dichloromethane (20 mL). The organic layers were combined, dried (Na$_2$SO$_4$), filtered and the solvent was removed in vacuo to give the title compound as a brown foamy solid, which was used without further purification.

Preparation 49

Methyl 4-{3-[4-(Biphenyl-2-ylcarbamoyloxy)piperidin-1-yl]propionylamino}-5-chloro-2-methoxybenzoate To the crude product from Preparation 48 was added the product of Example 1, Step 1 (1.33 g, 4.5 mmol) and a mixture of THF (22.5 mL) and methanol (2.5 mL). This mixture was heated at 50° C. with stirring for 16 h and then the solvent was removed in vacuo. The residue was chromatographed (silica gel; EtOAc) to give the title compound. (0.82 g; $R_f$=0.4, 29% yield over 3 steps) as an off-white foamy solid. MS m/z 566.4 (M+H, expected 565.20 for $C_{30}H_{32}ClN_3O_6$).

Preparation 50

Biphenyl-2-ylcarbamic Acid 1-[2-(2-Chloro-4-hydroxymethyl-5-methoxy-phenylcarbamoyl)ethyl]piperidin-4-yl Ester To a solution of the product of Preparation 49 (0.82 mg, 1.45 mmol) in a mixture of THF (4.5 mL) and methanol (0.5 mL) at 0° C. was added lithium borohydride (32 mg, 1.45 mmol). The reaction mixture was allowed to warm to room temperature and was stirred for 41 h. The reaction was then quenched by adding 1N aqueous hydrochloric acid at 0° C. until no more bubbling was observed and this mixture was stirred for 10 min. The solvent was removed in vacuo and the residue was dissolved in acetonitrile (about 2 mL). This solution was purified by prep-RP-HPLC (gradient: 2 to 50% acetonitrile in water with 0.05% TFA). The appropriate fractions were collected and combined and lyophilized to give the title compound as a trifluoroacetate salt. This salt was treated with isopropyl acetate (10 mL) and 1N aqueous sodium hydroxide (10 mL) and the organic layer was collected, dried ($Na_2SO_4$), filtered and the solvent was removed in vacuo to give the title compound (161 mg, 21% yield) as a white foamy solid. MS m/z 538.4 (M+H, expected 537.20 for $C_{29}H_{32}ClN_3O_5$).

Preparation 51

Biphenyl-2-ylcarbamic Acid 1-[2-(2-Chloro-4-formyl-5-methoxyphenylcarbamoyl)-ethyl]piperidin-4-yl Ester To a solution of the product of Preparation 50 (161 mg, 0.3 mmol) in dichloromethane (3 mL) was added dimethyl sulfoxide (213 µL, 3.0 mmol) and diisopropylethylamine (261 µL, 1.5 mmol). This mixture was cooled to –20° C. and sulfur trioxide pyridine complex (238 mg, 1.5 mmol) was added slowly. After 30 min, the reaction mixture was quenched by adding water (about 3 mL). The layers were separated and the organic layer was dried ($Na_2SO_4$), filtered and the solvent was removed in vacuo to give the title compound as a light yellow solid. MS m/z 536.3 (M+H, expected 535.19 for $C_{29}H_{30}ClN_3O_5$).

Preparation 52

Biphenyl-2-ylcarbamic Acid 1-[2-(4-[1,3]dioxolan-2-ylphenylcarbamoyl)-ethyl]-4-methylpiperidin-4-yl Ester A mixture of biphenyl-2-ylcarbamic acid 4-methylpiperidin-4-yl ester (2.73 g, 8.79 mmol) and N-(4-[1,3]dioxolan-2-yl-phenyl)acrylamide (2.05 g, 8.80 mmol) were heated in 100 mL of 1:1 methanol/dichloromethane at 50° C. under nitrogen for 1 h. The solution was then diluted with ethyl acetate and the organic layer was washed with water, brine, dried ($MgSO_4$) and concentrated under reduced pressure to give the title compound. MS m/z calcd for $C_{31}H_{35}N_3O_5(M+H)^+$ 530.6; found 530.4.

Preparation 53

Biphenyl-2-ylcarbamic Acid 1-[2-(4-Formylphenylcarbamoyl)ethyl]-4-methylpiperidin-4-yl Ester The product of Preparation 52 was redissolved in 40 mL of methanol and 25 mL of aqueous 1 N hydrochloric acid was added. The resulting mixture was stirred at room temperature overnight and the organic solvent was removed under reduced pressure. The residue was dissolved in ethyl acetate and the organic layer was washed with water, brine, dried ($MgSO_4$) and the solvent removed under reduced pressure. The product was triturated with dichloromethane to give the title compound as a white powder (2.47 g). LCMS (2-90) $R_t$=4.27 min; MS m/z calcd for $C_{29}H_{31}N_3O_4(M+H)^+$486.6, found 486.5.

Preparation 54

Biphenyl-2-ylcarbamic acid (R)-(1-azabicyclo[3.2.1]oct-4-yl) Ester

2-Biphenyl isocyanate (1.00 g, 5.12 mmol) and (R)-(–)-3-quinuclidinol hydrochloride (921 mg, 5.63 mmol) were heated together in N,N-dimethylformamide (2.06 mL) at 110° C. for 12 h. The reaction mixture was cooled and diluted with ethyl acetate (15 mL) and then washed with saturated aqueous sodium bicarbonate (2×10 mL). The organic layer was extracted with 1 M hydrochloric acid (3×20 mL) and the combined aqueous extracts were made basic to pH 8-9 with potassium carbonate. The aqueous layer was then extracted with ethyl acetate (3×20 mL) and the combined organic layers were dried (magnesium sulfate) and solvent was removed under reduced pressure to give the title compound as a yellow oil (1.64 g, 99% yield).

Preparation 55

(R)-4-(Biphenyl-2-ylcarbamoyloxy)-1-(9-bromononyl)-1-azoniabicyclo[3.2.1]octane Bromide To a stirred solution of the product of Preparation 54 (1.21 g, 3.76 mmol) and triethylamine (1.05 mL, 7.52 mmol) in acetonitrile (18.8 mL) was added 1,9-dibromononane (994 µL, 4.89 mmol) and the reaction mixture was heated at 50° C. for 4 h. The reaction mixture was then cooled and the solvent was removed under reduced pressure. The residue was dissolved in dichloromethane (20 mL) and the organic layer was washed with saturated aqueous sodium bicarbonate (10 mL), dried (magnesium sulfate) and solvent removed under reduced pressure. The crude product was purified by flash chromatography (10% methanol/dichloromethane, 0.5% ammonium hydroxide) to give the title compound (1.04 g, 1.97 mmol, 52% yield).

Preparation 56

(R)-1-(9-N,N-Di(tert-butoxycarbonyl)aminononyl)-4-(biphenyl-2-ylcarbamoyloxy)-1-azoniabicyclo[3.2.1]octane Bromide To a stirred solution of sodium hydride (60% dispersion in mineral oil) (126 mg, 3.15 mmol) in N,N-dimethylformamide (10 mL) under an atmosphere of nitrogen at 0° C., was added di-tert-butyl iminodicarboxylate (513 mg, 2.36 mmol) in N,N-dimethylformamide (5 mL). The reaction mixture was stirred at room temperature for 15 min and then it was cooled to 0° C. and the product of Preparation 55 (1.04 g, 1.97 mmol) in N,N-dimethylformamide (5 mL) was added. The reaction mixture was allowed to warm to room temperature over a 12 h period and then the solvent was removed under reduced pressure to give the title compound, which was used without further purification.

Preparation 57

(R)-1-(9-Aminononyl)-4-(biphenyl-2-ylcarbamoyloxy)-1-azoniabicyclo[3.2.1]octane Bromide The product of Preparation 56 (1.31 g, 1.97 mmol) was dissolved in dichloromethane (15 mL) and trifluoroacetic acid (5 mL) was added slowly. The reaction mixture was stirred at room temperature for 1 h and then the solvent was removed under reduced pressure. The residue was dissolved in dichloromethane (20 mL) and washed with aqueous 1 M sodium hydroxide (20 mL). The organic layer was extracted with 1 M hydrochloric acid (3×20 mL) and the combined aqueous extracts were made basic with potassium carbonate and extracted with dichloromethane (3×20 mL). The combined organic layers were dried (magnesium sulfate) and solvent was removed under reduced pressure to give the title compound (210 mg, 23% yield over 2 steps).

Preparation A
Cell Culture and Membrane Preparation from Cells Expressing Human $\beta_1$, $\beta_2$ or $\beta_3$ Adrenergic Receptors Chinese hamster ovarian (CHO) cell lines stably expressing cloned human $\beta_1$, $\beta_2$ or $\beta_3$ adrenergic receptors, respectively, were grown to near confluency in Hams F-12 media with 10% FBS in the presence of 500 µg/mL Geneticin. The cell monolayer was lifted with 2 mM EDTA in PBS. Cells were pelleted by centrifugation at 1,000 rpm, and cell pellets were either stored frozen at −80° C. or membranes were prepared immediately for use. For preparation of $\beta_1$ and $\beta_2$ receptor expressing membranes, cell pellets were re-suspended in lysis buffer (10 mM HEPES/HCl, 10 mM EDTA, pH 7.4 at 4° C.) and homogenized using a tight-fitting Dounce glass homogenizer (30 strokes) on ice. For the more protease-sensitive $\beta_3$ receptor expressing membranes, cell pellets were homogenated in lysis buffer (10 mM Tris/HCl, pH 7.4) supplemented with one tablet of "Complete Protease Inhibitor Cocktail Tablets with 2 mM EDTA" per 50 mL buffer (Roche Catalog No. 1697498, Roche Molecular Biochemicals, Indianapolis, Ind.). The homogenate was centrifuged at 20,000×g, and the resulting pellet was washed once with lysis buffer by re-suspension and centrifugation as above. The final pellet was then re-suspended in ice-cold binding assay buffer (75 mM Tris/HCl pH 7.4, 12.5 mM $MgCl_2$, 1 mM EDTA). The protein concentration of the membrane suspension was determined by the methods described in Lowry et al., 1951, *Journal of Biological Chemistry*, 193, 265; and Bradford, *Analytical Biochemistry*, 1976, 72, 248-54. All membranes were stored frozen in aliquots at −80° C. or used immediately.

Preparation B
Cell Culture and Membrane Preparation from Cells Expressing Human $M_1$, $M_2$, $M_3$ and $M_4$ Muscarinic Receptors CHO cell lines stably expressing cloned human $hM_1$, $hM_2$, $hM_3$ and $hM_4$ muscarinic receptor subtypes, respectively, were grown to near confluency in HAM's F-12 media supplemented with 10% FBS and 250 µg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately for use. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with re-suspension buffer and homogenized again with the Polytron tissue disrupter. The protein concentration of the membrane suspension was determined by the method described in Lowry et al., 1951, *Journal of Biochemistry*, 193, 265. All membranes were stored frozen in aliquots at −80° C. or used immediately. Aliquots of prepared $hM_5$ receptor membranes were purchased directly from Perkin Elmer and stored at −80° C. until use.

Assay Test Procedure A
Radioligand Binding Assay for Human $\beta_1$, $\beta_2$ and $\beta_3$ Adrenergic Receptors Binding assays were performed in 96-well microtiter plates in a total assay volume of 100 µL with 10-15 µg of membrane protein containing the human $\beta_1$, $\beta_2$ or $\beta_3$ adrenergic receptors in assay buffer (75 mM Tris/HCl pH 7.4 at 25° C., 12.5 mM $MgCl_2$, 1 mM EDTA, 0.2% BSA). Saturation binding studies for determination of $K_d$ values of the radioligand were done using [$^3$H]-dihydroalprenolol (NET-720, 100 Ci/mmol, PerkinElmer Life Sciences Inc., Boston, Mass.) for the $\beta_1$ and $\beta_2$ receptors and [$^{125}$I]-(−)-iodocyanopindolol (NEX-189, 220 Ci/mmol, PerkinElmer Life Sciences Inc., Boston, Mass.) at 10 or 11 different concentrations ranging from 0.01 nM to 20 nM. Displacement assays for determination of $K_i$ values of test compounds were done with [$^3$H]-dihydroalprenolol at 1 nM and [$^{125}$I]-(−)-iodocyanopindolol at 0.5 nM for 10 or 11 different concentrations of test compound ranging from 10 µM to 10 µM. Non-specific binding was determined in the presence of 10 µM propranolol. Assays were incubated for 1 hour at 37° C., and then binding reactions were terminated by rapid filtration over GF/B for the $\beta_1$ and $\beta_2$ receptors or GF/C glass fiber filter plates for the $\beta_3$ receptors (Packard BioScience Co., Meriden, Conn.) pre-soaked in 0.3% polyethyleneimine. Filter plates were washed three times with filtration buffer (75 mM Tris/HCl pH 7.4 at 4° C., 12.5 mM $MgCl_2$, 1 mM EDTA) to remove unbound radioactivity. The plates were then dried and 50 µL of Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM propranolol. $K_i$ values for test compounds were calculated from observed $IC_{50}$ values and the $K_d$ value of the radioligand using the Cheng-Prusoff equation (Cheng Y, and Prusoff W H., *Biochemical Pharmacology*, 1973, 22, 23, 3099-108).

In this assay, a lower $K_i$ value indicates that a test compound has a higher binding affinity for the receptor tested. Exemplified compound of this invention that were tested in this assay typically were found to have a $K_i$ value of less than about 300 nM for the $\beta_2$ adrenergic receptor. For example, the compounds of Examples 1 to 3 were found to have $K_i$ values of less than 30 nM.

Assay Test Procedure B
Radioligand Binding Assay for Muscarinic Receptors

Radioligand binding assays for cloned human muscarinic receptors were performed in 96-well microtiter plates in a total assay volume of 100 µL. CHO cell membranes stably expressing either the $hM_1$, $hM_2$, $hM_3$, $hM_4$ or $hM_5$ muscarinic subtype were diluted in assay buffer to the following specific target protein concentrations (µg/well): 10 µg for $hM_1$, 10-15 µg for $hM_2$, 10-20 µg for $hM_3$, 10-20 µg for $hM_4$, and 10-12 µg for $hM_5$ to get similar signals (cpm). The membranes were briefly homogenized using a Polytron tissue disruptor (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of K, values of test compounds were performed with [$^3$H]-NMS at 1 nM and eleven different test compound concentrations. The test compounds were initially dissolved to a concentration of 400 µM in dilution buffer and then serially diluted 5× with dilution buffer to final concentrations ranging from 10 pM to 100 µM. The addition order and volumes to the assay plates were as follows: 25 µL radioligand, 25 µL diluted test compound, and 50 µL membranes. Assay plates were incubated for 60 minutes at 37° C. Binding reactions were terminated by rapid filtration over GF/B glass fiber filter plates (PerkinElmer Inc., Wellesley, Mass.) pretreated in 1% BSA. Filter plates were rinsed three times with wash buffer (10 mM HEPES) to remove unbound radioactivity. The plates were then air dried and 50 µL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology*, 22(23):3099-108). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. Exemplified compound of this invention that were tested in this assay typically were found to have a $K_i$ value of less than about 300 nM for the $M_3$ muscarinic receptor. For example, the compounds of Examples 1 to 4 were found to have $K_i$ values of less than 10 nM.

Assay Test Procedure C
Whole-Cell cAMP Flashplate Assay in CHO Cell Lines Heterologously Expressing Human $\beta_1$, $\beta_2$ or $\beta_3$ Adrenergic Receptors cAMP assays were performed in a radioimmunoassay format using the Flashplate Adenylyl Cyclase Activation Assay System with $[^{125}I]$-cAMP (NEN SMP004, PerkinElmer Life Sciences Inc., Boston, Mass.), according to the manufacturers instructions. For the determination of β receptor agonist potency ($EC_{50}$), CHO-K1 cell lines stably expressing cloned human $\beta_1$, $\beta_2$ or $\beta_3$ adrenergic receptors were grown to near confluency in HAM's F-12 media supplemented with 10% FBS and Geneticin (250 µg/mL). Cells were rinsed with PBS and detached in dPBS (Dulbecco's Phosphate Buffered Saline, without $CaCl_2$ and $MgCl_2$) containing 2 mM EDTA or Trypsin-EDTA solution (0.05% trypsin/0.53 mM EDTA). After counting cells in Coulter cell counter, cells were pelleted by centrifugation at 1,000 rpm and re-suspended in stimulation buffer containing IBMX (PerkinElmer Kit) pre-warmed to room temperature to a concentration of $1.6 \times 10^6$ to $2.8 \times 10^6$ cells/mL. About 60,000 to 80,000 cells per well were used in this assay. Test compounds (10 mM in DMSO) were diluted into PBS containing 0.1% BSA in Beckman Biomek-2000 and tested at 11 different concentrations ranging from 100 µM to 1 µM. Reactions were incubated for 10 min at 37° C. and stopped by adding 100 µL of cold detection buffer containing $[^{125}I]$-cAMP (NEN SMP004, PerkinElmer Life Sciences, Boston, Mass.). The amount of cAMP produced (pmol/well) was calculated based on the counts observed for the samples and cAMP standards as described in the manufacturer's user manual. Data were analyzed by nonlinear regression analysis with the GraphPad Prism Software package (GraphPad Software, Inc., San Diego, Calif.) with the sigmoidal equation. The Cheng-Prusoff equation (Cheng Y, and Prusoff W H., *Biochemical Pharmacology*, 1973, 22, 23, 3099-108) was used to calculate the EC50 values.

In this assay, a lower $EC_{50}$ value indicates that the test compound has a higher functional activity at the receptor tested. Exemplified compound of this invention that were tested in this assay typically were found to have a $EC_{50}$ value of less than about 300 nM for the $\beta_2$ adrenergic receptor. For example, the compounds of Examples 1 to 4 were found to have $EC_{50}$ values of less than 30 nM.

If desired, the receptor subtype selectivity for a test compound can be calculated as the ratio of $EC_{50}(\beta_1)/EC_{50}(\beta_2)$ or $EC_{50}(\beta_3)/EC_{50}(\beta_2)$. Typically, compounds of this invention demonstrated greater functional activity at the $\beta_2$ adrenergic receptor compared to the $\beta_1$ or $\beta_3$ adrenergic receptor, i.e. $EC_{50}(\beta_1)$ or $EC_{50}(\beta_3)$ is typically greater than $EC_{50}(\beta_2)$. Generally, compounds having selectivity for the $\beta_2$ adrenergic receptor over the $\beta_1$ or $\beta_3$ adrenergic receptors are preferred; especially compounds having a selectivity greater than about 5; and in particular, greater than about 10. By way of example, the compounds of Examples 1 to 4 had ratios of $EC_{50}(\beta_1)/EC_{50}(\beta_2)$ greater than 10.

Assay Test Procedure D
Functional Assays of Antagonism for Muscarinic Receptor Subtypes A. Blockade of Agonist-Mediated Inhibition of cAMP Accumulation In this assay, the functional potency of a test compound is determined by measuring the ability of the test compound to block oxotremorine-inhibition of forskolin-mediated cAMP accumulation in CHO-K1 cells expressing the $hM_2$ receptor. cAMP assays are performed in a radioimmunoassay format using the Flashplate Adenylyl Cyclase Activation Assay System with $^{125}I$-cAMP (NEN SMP004B, PerkinElmer Life Sciences Inc., Boston, Mass.), according to the manufacturer's instructions. Cells are rinsed once with dPBS and lifted with Trypsin-EDTA solution (0.05% trypsin/0.53 mM EDTA) as described in the Cell Culture and Membrane Preparation section above. The detached cells are washed twice by centrifugation at 650×g for five minutes in 50 mL dPBS. The cell pellet is then re-suspended in 10 mL dPBS, and the cells are counted with a Coulter Z1 Dual Particle Counter (Beckman Coulter, Fullerton, Calif.). The cells are centrifuged again at 650×g for five minutes and re-suspended in stimulation buffer to an assay concentration of $1.6 \times 10^6$-$2.8 \times 10^6$ cells/mL.

The test compound is initially dissolved to a concentration of 400 µM in dilution buffer (dPBS supplemented with 1 mg/mL BSA (0.1%)), and then serially diluted with dilution buffer to final molar concentrations ranging from 100 µM to 0.1 nM. Oxotremorine is diluted in a similar manner.

To measure oxotremorine inhibition of adenylyl cyclase (AC) activity, 25 µL forskolin (25 µM final concentration diluted in dPBS), 25 µL diluted oxotremorine, and 50 µL cells are added to agonist assay wells. To measure the ability of a test compound to block oxotremorine-inhibited AC activity, 25 µL forskolin and oxotremorine (25 µM and 5 µM final concentrations, respectively, diluted in dPBS), 25 µL diluted test compound, and 50 µL cells are added to remaining assay wells.

Reactions are incubated for 10 minutes at 37° C. and stopped by addition of 100 µL ice-cold detection buffer. Plates are sealed, incubated overnight at room temperature and counted the next morning on a PerkinElmer TopCount liquid scintillation counter (PerkinElmer Inc., Wellesley, Mass.). The amount of cAMP produced (pmol/well) is calculated based on the counts observed for the samples and cAMP standards, as described in the manufacturer's user manual. Data is analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $EC_{50}$ of the oxotremorine concentration-response curve and the oxotremorine assay concentration as the $K_D$ and [L], respectively.

In this assay, a lower $K_i$ value indicates that the test compound has a higher functional activity at the receptor tested. Exemplified compounds of this invention are expected to have a $K_i$ value of less than about 300 nM for blockade of oxotremorine-inhibition of forskolin-mediated cAMP accumulation in CHO-K1 cells expressing the $hM_2$ receptor.

B. Blockade of Agonist-Mediated [$^{35}$S]GTPγS Binding

In a second functional assay, the functional potency of test compounds is determined by measuring the ability of the compounds to block oxotremorine-stimulated [$^{35}$S]GTPγS binding in CHO-K1 cells expressing the hM$_2$ receptor.

At the time of use, frozen membranes were thawed and then diluted in assay buffer with a final target tissue concentration of 5-10 μg protein per well. The membranes were briefly homogenized using a Polytron PT-2100 tissue disrupter and then added to the assay plates.

The EC$_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 μL, of assay buffer with [$^{35}$S]GTPγS (0.4 nM), 25 μL of oxotremorine (EC$_{90}$) and GDP (3 uM), 25 μL of diluted test compound and 25 μL CHO cell membranes expressing the hM$_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 μL) was added to each well, and each plate was sealed and radioactivity counted on a Topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the K$_i$, using the IC$_{50}$ values of the concentration-response curve for the test compound and the oxotremorine concentration in the assay as the K$_D$ and [L], ligand concentration, respectively.

In this assay, a lower K$_i$ value indicates that the test compound has a higher functional activity at the receptor tested. Exemplified compound of this invention that were tested in this assay typically were found to have a K$_i$ value of less than about 300 nM for blockade of oxotremorine-stimulated [$^{35}$S]GTPγS binding in CHO-K1 cells expressing the hM$_2$ receptor. For example, the compound of Example 1 was found to have a K$_i$ value of less than 10 nM.

C. Blockade of Agonist-Mediated Calcium Release via FLIPR Assays

Muscarinic receptor subtypes (M$_1$, M$_3$ and M$_5$ receptors), which couple to G$_q$ proteins, activate the phospholipase C (PLC) pathway upon agonist binding to the receptor. As a result, activated PLC hydrolyzes phosphatyl inositol diphosphate (PIP$_2$) to diacylglycerol (DAG) and phosphatidyl-1,4,5-triphosphate (IP$_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human M$_1$ and M$_3$, and chimpanzee M$_5$ receptors. Antagonist potency can be determined by the ability of antagonists to inhibit agonist-mediated increases in intracellular calcium.

For FLIPR calcium stimulation assays, CHO cells stably expressing the hM$_1$, hM$_3$ and cM$_5$ receptors are seeded into 96-well FLIPR plates the night before the assay is done. Seeded cells are washed twice by Cellwash (MTX Labsystems, Inc.) with FLIPR buffer (10 mM HEPES, pH 7.4, 2 mM calcium chloride, 2.5 mM probenecid in Hank's Buffered Salt Solution (HBSS) without calcium and magnesium) to remove growth media and leaving 50 μL/well of FLIPR buffer. The cells are then incubated with 50 μL/well of 4 μM FLUO-4AM (a 2× solution was made) for 40 minutes at 37° C., 5% carbon dioxide. Following the dye incubation period, cells are washed two times with FLIPR buffer, leaving a final volume of 50 μL/well.

To determine antagonist potency, the dose-dependent stimulation of intracellular Ca$^{2+}$ release for oxotremorine is first determined so that antagonist potency can later be measured against oxotremorine stimulation at an EC$_{90}$ concentration. Cells are first incubated with compound dilution buffer for 20 minutes, followed by agonist addition, which is performed by the FLIPR. An EC$_{90}$ value for oxotremorine is generated according to the method detailed in the FLIPR measurement and data reduction section below, in conjunction with the formula $EC_F = ((F/100-F)^{\wedge}1/H)*EC_{50}$. An oxotremorine concentration of 3×EC$_F$ is prepared in stimulation plates such that an EC$_{90}$ concentration of oxotremorine is added to each well in the antagonist inhibition assay plates.

The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response. Antagonist K$_i$ values are determined by Prism using the oxotremorine EC$_{50}$ value as the K$_D$ and the oxotremorine EC$_{90}$ for the ligand concentration according to the Cheng-Prusoff equation (Cheng & Prusoff, 1973).

In this assay, a lower K$_i$ value indicates that the test compound has a higher functional activity at the receptor tested. Exemplified compound of this invention are expected to have a K$_i$ value of less than about 300 nM for blockade of agonist-mediated calcium release in CHO cells stably expressing the hM$_1$, hM$_3$ and cM$_5$ receptors.

Assay Test Procedure E

Whole-Cell cAMP Flashplate Assay with a Lung Epithelial Cell Line Endogenously Expressing Human β$_2$ Adrenergic Receptor For the determination of agonist potencies and efficacies (intrinsic activities) in a cell line expressing endogenous levels of the β$_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701-11). Cells were grown to 75-90% confluency in complete, serum-free medium (LHC-9 MEDIUM containing Epinephrine and Retinoic Acid, cat #181-500, Biosource International, Camarillo, Calif.). The day before the assay, medium was switched to LHC-8 (no epinephrine or retinoic acid, cat #141-500, Biosource International, Camarillo, Calif.). cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions. On the day of the assay, cells were rinsed with PBS, lifted by scraping with 5 mM EDTA in PBS, and counted. Cells were pelleted by centrifugation at 1,000 rpm and re-suspended in stimulation buffer pre-warmed to 37° C. at a final concentration of 600,000 cells/mL. Cells were used at a final concentration of 100,000 to 120,000 cells/well in this assay. Test compounds were serially diluted into assay buffer (75 mM Tris/HCl pH 7.4 at 25° C., 12.5 mM MgCl$_2$, 1 mM EDTA, 0.2% BSA) in Beckman Biomek-2000. Test compounds were tested in the assay at 11 different concentrations, ranging from 10 µM to 10 µM. Reactions were incubated for 10 mM at 37° C. and stopped by addition of 100 µL of ice-cold detection buffer. Plates were sealed, incubated over night at 4° C. and counted the next morning in a Topcount scintillation counter (Packard BioScience Co., Meriden, Conn.). The amount of cAMP produced per mL of reaction was calculated based on the counts observed for samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response.

In this assay, a lower $EC_{50}$ value indicates that the test compound has a higher functional activity at the receptor tested. Exemplified compound of this invention that were tested in this assay typically were found to have a $EC_{50}$ value of less than about 300 nM for the $\beta_2$ adrenergic receptor. For example, the compounds of Examples 1 to 3 were found to have $EC_{50}$ values ranging from less than 10 nM to less than 200 nM.

Assay Test Procedure F
Duration of Bronchoprotection in Guinea Pig Models of Acetylcholine-Induced or Histamine-Induced Bronchoconstriction These in vivo assays are used to assess the bronchoprotective effects of test compounds exhibiting both muscarinic receptor antagonist and $\beta_2$ adrenergic receptor agonist activity. To isolate muscarinic antagonist activity in the acetylcholine-induced bronchoconstriction model, the animals are administered propanolol, a compound that blocks $\beta$ receptor activity, prior to the administration of acetylcholine. Duration of bronchoprotection in the histamine-induced bronchoconstriction model reflects $\beta_2$ adrenergic receptor agonist activity.

Groups of 6 male guinea pigs (Duncan-Hartley (HsdPoc: DH) Harlan, Madison, Wis.) weighing between 250 and 350 g are individually identified by cage cards. Throughout the study, animals are allowed access to food and water ad libitum.

Test compounds are administered via inhalation over 10 minutes in a whole-body exposure dosing chamber (R&S Molds, San Carlos, Calif.). The dosing chambers are arranged so that an aerosol is simultaneously delivered to 6 individual chambers from a central manifold. Guinea pigs are exposed to an aerosol of a test compound or vehicle (WFI). These aerosols are generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure is approximately 3 L/minute. The generated aerosols are driven into the chambers by positive pressure. No dilution air is used during the delivery of aerosolized solutions. During the 10 minute nebulization, approximately 1.8 mL of solution is nebulized. This value is measured gravimetrically by comparing pre- and post-nebulization weights of the filled nebulizer.

The bronchoprotective effects of test compounds administered via inhalation are evaluated using whole body plethysmography at 1.5, 24, 48 and 72 hours post-dose.

Forty-five minutes prior to the start of the pulmonary evaluation, each guinea pig is anesthetized with an intramuscular injection of ketamine (43.75 mg/kg), xylazine (3.50 mg/kg) and acepromazine (1.05 mg/kg). After the surgical site is shaved and cleaned with 70% alcohol, a 2-3 cm midline incision of the ventral aspect of the neck is made. Then, the jugular vein is isolated and cannulated with a saline-filled polyethylene catheter (PE-50, Becton Dickinson, Sparks, Md.) to allow for intravenous infusions of acetylcholine (Ach) or histamine in saline. The trachea is then dissected free and cannulated with a 14G teflon tube (#NE-014, Small Parts, Miami Lakes, Fla.). If required, anesthesia is maintained by additional intramuscular injections of the aforementioned anesthetic mixture. The depth of anesthesia is monitored and adjusted if the animal responds to pinching of its paw or if the respiration rate is greater than 100 breaths/minute.

Once the cannulations are completed, the animal is placed into a plethysmograph (#PLY3114, Buxco Electronics, Inc., Sharon, Conn.) and an esophageal pressure cannula (PE-160, Becton Dickinson, Sparks, Md.) is inserted to measure pulmonary driving pressure (pressure). The teflon tracheal tube is attached to the opening of the plethysmograph to allow the guinea pig to breathe room air from outside the chamber. The chamber is then sealed. A heating lamp is used to maintain body temperature and the guinea pig's lungs are inflated 3 times with 4 mL of air using a 10 mL calibration syringe (#5520 Series, Hans Rudolph, Kansas City, Mo.) to ensure that the lower airways do not collapse and that the animal does not suffer from hyperventilation.

Once it is determined that baseline values are within the range of 0.3-0.9 mL/cm $H_2O$ for compliance and within the range of 0.1-0.199 cm $H_2O$/mL per second for resistance, the pulmonary evaluation is initiated. A Buxco pulmonary measurement computer program enabled the collection and derivation of pulmonary values.

Starting this program initiated the experimental protocol and data collection. The changes in volume over time that occur within the plethysmograph with each breath are measured via a Buxco pressure transducer. By integrating this signal over time, a measurement of flow is calculated for each breath. This signal, together with the pulmonary driving pressure changes, which are collected using a Sensym pressure transducer (#TRD4100), is connected via a Buxco (MAX 2270) preamplifier to a data collection interface (#'s SFT3400 and SFT3813). All other pulmonary parameters are derived from these two inputs.

Baseline values are collected for 5 minutes, after which time the guinea pigs are challenged with Ach or histamine. When evaluating the muscarinic antagonist effects, propanolol (5 mg/Kg, iv) (Sigma-Aldrich, St. Louis, Mo.) is administered 15 minutes prior to challenge with Ach. Ach (Sigma-Aldrich, St. Louis, Mo.) (0.1 mg/mL) is infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. Alternatively, bronchoprotection of test compounds is assessed in the acetylcholine challenge model without pretreatment with a beta blocking compound.

When evaluating the $\beta_2$ adrenergic receptor agonist effects of test compounds, histamine (25 µg/mL) (Sigma-Aldrich, St. Louis, Mo.) is infused intravenously for 1 minute from a syringe pump at the following doses and prescribed times from the start of the experiment: 0.5 µg/minute at 5 minutes, 0.9 µg/minute at 10 minutes, 1.9 µg/minute at 15 minutes, 3.8 µg/minute at 20 minutes, 7.5 µg/minute at 25 minutes and 15 µg/minute at 30 minutes. If resistance or compliance does not returned to baseline values at 3 minutes following each Ach or histamine dose, the guinea pig's lungs are inflated 3 times with 4 mL of air from a 10 mL calibration syringe. Recorded pulmonary parameters include respiration frequency (breaths/minute), compliance (mL/cm $H_2O$) and pulmonary resistance (cm $H_2O$/mL per second). Once the pulmonary function measurements are completed at minute 35 of this protocol, the guinea pig is removed from the plethysmograph and euthanized by carbon dioxide asphyxiation.

The data are evaluated in one of two ways:

(a) Pulmonary resistance ($R_L$, cm $H_2O$/mL per second) is calculated from the ratio of "change in pressure" to "the change in flow." The $R_L$ response to ACh (60 μg/min, IH) is computed for the vehicle and the test compound groups. The mean ACh response in vehicle-treated animals, at each pre-treatment time, is calculated and used to compute % inhibition of ACh response, at the corresponding pre-treatment time, at each test compound dose. Inhibition dose-response curves for '$R_L$' are fitted with a four parameter logistic equation using GraphPad Prism, version 3.00 for Windows (GraphPad Software, San Diego, Calif.) to estimate bronchoprotective $ID_{50}$ (dose required to inhibit the ACh (60 μg/min) bronchoconstrictor response by 50%). The equation used is as follows:

$$Y = \text{Min} + (\text{Max} - \text{Min})/(1+10^{((\log ID50 - X)*Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of Ach or histamine needed to cause a doubling of the baseline pulmonary resistance, is calculated using the pulmonary resistance values derived from the flow and the pressure over a range of Ach or histamine challenges using the following equation (derived from the equation used to calculate $PC_{20}$ values (see *Am. Thoracic Soc*, 2000):

$$PD_2 = \text{antilog}\left[\log C_1 + \frac{(\log C_2 - \log C_1)(2R_0 - R_1)}{R_2 - R_1}\right]$$

where:
$C_1$=concentration of Ach or histamine preceding $C_2$
$C_2$=concentration of Ach or histamine resulting in at least a 2-fold increase in pulmonary resistance ($R_L$)
$R_0$=Baseline $R_L$ value
$R_1$=$R_L$ value after $C_1$
$R_2$=$R_L$ value after $C_2$ Statistical analysis of the data is performed using a two tailed-Students t-test. A P-value <0.05 is considered significant.

Exemplified compounds of this invention are expected to produce a dose-dependent bronchoprotective effect against MCh-induced bronchoconstriction and His-induced bronchoconstriction. Generally, test compounds having a potency ($ID_{50}$ at 1.5 h post-dose) of less than about 300 μg/mL for ACh-induced bronchoconstriction and less than about 300 μg/mL for His-induced bronchoconstriction in this assay are generally preferred. Additionally, test compounds having a duration (PD $T_{1/2}$) of brochoprotective activity of at least about 24 hours in this assay are generally preferred.

Assay Test Procedure G
Einthoven Model for Measuring Changes in Ventilation in Guinea Pigs The bronchodilator activity of test compounds is evaluated in an anesthetized guinea pig model (the Einthoven model), which uses ventilation pressure as a surrogate measure of airway resistance. See, for example, Einthoven (1892) *Pfugers Arch*. 51: 367-445; and Mohammed et al. (2000) *Pulm Pharmacol Ther*. 13(6):287-92. In this model, muscarinic antagonist and $\beta_2$ agonist activity is assessed by determining the protective effects against methacholine (MCh) and histamine (His)-induced bronchoconstriction.

This assay is conducted using Duncan-Hartley guinea pigs (Harlan, Indianapolis, Ind.), weighing between 300 and 400 g.

The test compound or vehicle (i.e., sterile water) is dosed by inhalation (IH) over a 10 minute time period in a whole body exposure dosing chamber (R+S Molds, San Carlos, Calif.) using 5 mL of dosing solution. Animals are exposed to an aerosol, which is generated from an LC Star Nebulizer Set (Model 22F51, PARI Respiratory Equipment, Inc. Midlothian, Va.) driven by Bioblend a mixture of gasses (5% $CO_2$; 21% $O_2$; and 74% $N_2$) at a pressure of 22 psi. Pulmonary function is evaluated at various time-points after inhalation dosing.

Forty five minutes prior to the start of pulmonary function evaluation, the guinea pigs are anesthetized with an intramuscular (IM) injection of a mixture of ketamine (13.7 mg/kg/ xylazine (3.5 mg/kg)/acepromazine (1.05 mg/kg). A supplemental dose of this mixture (50% of initial dose) is administered as needed. The jugular vein and carotid artery are isolated and cannulated with saline-filled polyethylene catheters (micro-renathane and PE-50, respectively, Beckton Dickinson, Sparks, Md.). The carotid artery is connected to a pressure transducer to allow the measurement of blood pressure and the jugular vein cannula is used for IV injection of either MCh or His. The trachea is then dissected free and cannulated with a 14 G needle (#NE-014, Small Parts, Miami Lakes, Fla.). Once the cannulations are complete, the guinea pigs are ventilated using a respirator (Model 683, Harvard Apparatus, Inc., MA) set at a stroke volume of 1 mL/100 g body weight but not exceeding 2.5 mL volume, and at a rate of 100 strokes per minute. Ventilation pressure (VP) is measured in the tracheal cannula using a Biopac transducer that is connected to a Biopac (TSD 137C) pre-amplifier. Body temperature is maintained at 37° C. using a heating pad. Prior to initiating data collection, pentobarbital (25 mg/kg) is administered intraperitoneally (IP) to suppress spontaneous breathing and obtain a stable baseline. The changes in VP are recorded on a Biopac Windows data collection interface. Baseline values are collected for at least 5 minutes, after which time guinea pigs are challenged IV non-cumulatively with 2-fold incremental doses of the bronchoconstrictor (MCh or His). When MCh is used as the bronchoconstrictor agent, animals are pre-treated with propranolol (5 mg/kg, IV) to isolate the antimuscarinic effects of the test compound. Changes in VP are recorded using the Acknowledge Data Collection Software (Santa Barbara, Calif.). After the completion of study, the animals are euthanized.

Change in VP is measured in cm of water. Change in VP (cm $H_2O$)=peak pressure (after bronchoconstrictor challenge)-peak baseline pressure. The dose-response curve to MCh or His is fitted to a four parameter logistic equation using GraphPad Prism, version 3.00 for Windows (GraphPad Software, San Diego, Calif.) The equation used is as follows:

$$Y = \text{Min} + (\text{Max} - \text{Min})/(1+10^{((\log ID50 - X)*Hillslope)})$$

where X is the logarithm of dose, Y is the response. Y starts at Min and approaches asymptotically to Max with a sigmoidal shape.

The percent inhibition of the bronchoconstrictor response to a submaximal dose of MCh or His is calculated at each dose of the test compound using the following equation: % Inhibition of response=100-((peak pressure (after bronchoconstrictor challenge, treated)-peak baseline pressure (treated)*100%/(peak pressure (after bronchoconstrictor challenge, water)-peak baseline pressure (water)). Inhibition curves are fitted using the four parameter logistic equation from GraphPad software. $ID_{50}$ (dose required to produce 50% inhibition of the bronchoconstrictor response) and Emax (maximal inhibition) are also estimated wherever appropriate.

The magnitude of bronchoprotection at different time-points after inhalation of the test compound is used to estimate the pharmacodynamic half-life (PD $T_{1/2}$). PD $T_{1/2}$ is determined using a non-linear regression fit using a one-phase exponential decay equation (GraphPad Prism, Version 4.00): Y=Span*exp(-K*X)+Plateau; Starts at Span+Plateau and decays to Plateau with a rate constant K. The PD $T_{1/2}$=0.69/K. Plateau is constrained to 0.

Exemplified compounds of this invention are expected to produce a dose-dependent bronchoprotective effect against MCh-induced bronchoconstriction and His-induced bronchoconstriction. Generally, test compounds having an $ID_{50}$ less than about 300 μg/mL for MCh-induced bronchoconstriction and an $ID_{50}$ less than about 300 μg/mL for His-induced bronchoconstriction at 1.5 hours post-dose in this assay are preferred. Additionally, test compounds having a duration (PD $T_{1/2}$) of brochoprotective activity of at least about 24 hours in this assay are generally preferred.

Assay Test Procedure H
Inhalation Guinea Pig Salivation Assay

Guinea pigs (Charles River, Wilmington, Mass.) weighing 200-350 g are acclimated to the in-house guinea pig colony for at least 3 days following arrival. Test compound or vehicle are dosed via inhalation (LH) over a 10 minute time period in a pie shaped dosing chamber (R+S Molds, San Carlos, Calif.). Test solutions are dissolved in sterile water and delivered using a nebulizer filled with 5.0 mL of dosing solution. Guinea pigs are restrained in the inhalation chamber for 30 minutes. During this time, guinea pigs are restricted to an area of approximately 110 sq. cm. This space is adequate for the animals to turn freely, reposition themselves, and allow for grooming. Following 20 minutes of acclimation, guinea pigs are exposed to an aerosol generated from a LS Star Nebulizer Set (Model 22F51, PART Respiratory Equipment, Inc. Midlothian, Va.) driven by house air at a pressure of 22 psi. Upon completion of nebulization, guinea pigs are evaluated at 1.5, 6, 12, 24, 48, or 72 hrs after treatment.

Guinea pigs are anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals are placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) is inserted in the guinea pig's mouth. Five minutes later, the muscarinic agonist pilocarpine (3.0 mg/kg, s.c.) is administered and the gauze pad is immediately discarded and replaced by a new pre-weighed gauze pad. Saliva is collected for 10 minutes, at which point the gauze pad is weighed and the difference in weight recorded to determine the amount of accumulated saliva (in mg). The mean amount of saliva collected for animals receiving the vehicle and each dose of test compound is calculated. The vehicle group mean is considered to be 100% salivation. Results are calculated using result means (n=3 or greater). Confidence intervals (95%) are calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol*, 1996, 24:243-254.

The mean weight of saliva in vehicle-treated animals, at each pre-treatment time, is calculated and used to compute % inhibition of salivation, at the corresponding pre-treatment time, at each dose. The inhibition dose-response data are fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The equation used is as follows:

$$Y = \text{Min} + (\text{Max} - \text{Min})/(1+10^{((\log ID50 - X) * Hillslope)})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective $ID_{50}$ is used to compute the apparent lung-selectivity index of the test compound. Generally, compounds having an apparent lung-selectivity index greater than about 5 are preferred.

Assay Test Procedure I
Radioligand Competition Binding Assay in Cloned human Dopamine $D2_S$ Receptor In this assay, the binding affinity of test compounds for the human dopamine $D2_S$ receptor in transfected CHO cells is determined using a radioligand binding assay (Grady et al., *Proc. Natl. Acad. Sci. USA* 86:9762 (1989)).

Cell membrane homogenates (5-10 μg protein) were incubated for 60 minutes at 22° C. with 0.3 nM [$^3$H]spiperone in the absence or presence of a test compound in a buffer containing 50 mM Tris-HCl (pH 7.4), 120 mM NaCl, 5 mM KCl, 5 mM $MgCl_2$ and 1 mM EDTA. The test compound was used at a test concentration of 100 nM. Nonspecific binding was determined in the presence of 10 μM (+)-butaclamol.

Following incubation, the samples were filtered rapidly under vacuum through glass fiber filters (GF/B, Packard) presoaked with 0.3% polyethyleneimine and rinsed several times with ice-cold 50 mM Tris-HCl using a 96-sample cell harvester (Unifilter, Packard). The filters were dried, and then counted for radioactivity in a scintillation counter (Topcount, Packard) using a scintillation cocktail (Microscint 0, Packard).

The results were expressed as a percent inhibition of the control radioligand specific binding. Exemplified compounds of the invention tested in this assay were found to have a percent inhibition of greater than about 30%, including greater than about 75%, at a concentration of 100 nM. For example, the compound of Example 1 had a percent inhibition of greater than about 75%; and the compound of Example 2 had a percent inhibition of greater than about 30%.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:
1. A process for preparing a compound of formula I:

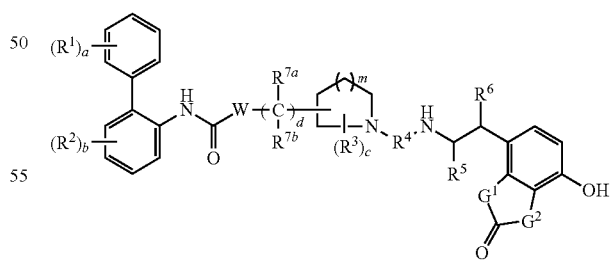

wherein
$G^1$ represents S; and $G^2$ represents NH;
W represents O or $NW^a$; where $W^a$ is hydrogen or (1-4C) alkyl;
each $R^1$ is independently selected from (1-4C)alkyl, (2-4C) alkenyl, (2-4C)alkynyl, (3-6C)cycloalkyl, cyano, halo, $-OR^{1a}$, $-C(O)OR^{1b}$, $-SR^{1c}$, $-S(O)R^{1d}$, $-S(O)_2R^{1e}$ and $-NR^{1f}R^{1g}$; where each of $R^{1a}$, $R^{1b}$, $R^{1c}$, $R^{1d}$, $R^{1e}$, $R^{1f}$ and $R^{1g}$ is independently hydrogen, (1-4C)alkyl or phenyl-(1-4C)alkyl;

each $R^2$ is independently selected from (1-4C)alkyl, (2-4C)alkenyl, (2-4C)alkynyl, (3-6C)cycloalkyl, cyano, halo, —$OR^{2a}$, —$C(O)OR^{2b}$, —$SR^{2c}$, —$S(O)R^{2d}$, —$S(O)_2R^{2e}$ and —$NR^{2f}R^{2g}$; where each of $R^{2a}$, $R^{2b}$, $R^{2c}$, $R^{2d}$, $R^{2e}$, $R^{2f}$ and $R^{2g}$ is independently hydrogen, (1-4C)alkyl or phenyl-(1-4C)alkyl;

each $R^3$ is independently selected from (1-4C)alkyl, (2-4C)alkenyl, (2-4C)alkynyl, (3-6C)cycloalkyl, cyano, halo, —$OR^{3a}$, —$C(O)OR^{3b}$, —$SR^{3c}$, —$S(O)R^{3d}$, —$S(O)_2R^{3e}$ and —$NR^{3f}R^{3g}$; or two $R^3$ groups are joined to form (1-3C)alkylene, (2-3C)alkenylene or oxiran-2,3-diyl; where each of $R^{3a}$, $R^{3b}$, $R^{3c}$, $R^{3d}$, $R^{3e}$, $R^{3f}$ and $R^{3g}$ is independently hydrogen or (1-4C)alkyl;

$R^4$ represents a divalent hydrocarbon group containing from 4 to 28 carbon atoms and optionally containing from 1 to 10 heteroatoms selected independently from halo, oxygen, nitrogen and sulfur, provided that the number of contiguous atoms in the shortest chain between the two nitrogen atoms to which $R^4$ is attached is in the range of from 4 to 16;

$R^5$ represents hydrogen or (1-4C)alkyl;
$R^6$ represents hydrogen or hydroxyl;
each $R^{7a}$ and $R^{7b}$ is independently selected from hydrogen, (1-4C)alkyl, hydroxy and fluoro;
a is 0 or an integer of from 1 to 3;
b is 0 or an integer of from 1 to 3;
c is 0 or an integer of from 1 to 4;
d is 0 or an integer of from 1 to 5; and
m is 0 or an integer of from 1 to 3;
or a pharmaceutically acceptable salt or stereoisomer thereof;
the process comprising:
(a) reacting a compound of formula 1:

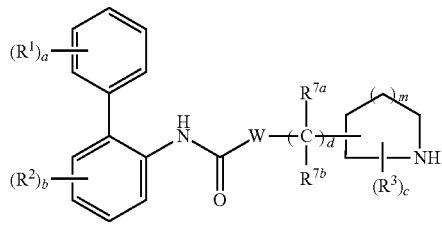

1 with a compound of formula 8:

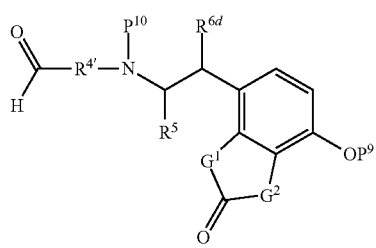

8 or a hydrate thereof, in the presence of a reducing agent, wherein $R^{6d}$ represents hydrogen or $OP^8$, $P^8$ and $P^9$ each independently represent a hydrogen atom or a hydroxyl-protecting group, $P^{10}$ represents a hydrogen atom or an amino-protecting group, and $R^{4'}$ represents a residue that, together with the carbon to which it is attached, affords a group $R^4$ upon completion of the reaction;

(b) reacting a compound of formula 9:

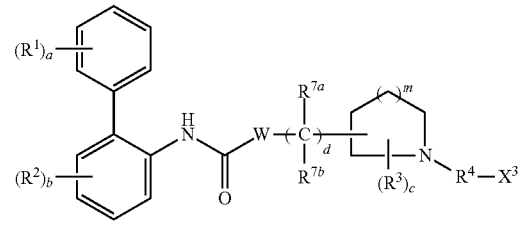

9 wherein $X^3$ represents a leaving group, with a compound of formula 10:

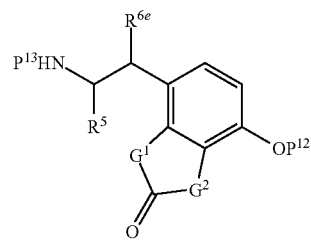

10 wherein $R^{6e}$ represents hydrogen or $OP^{11}$, $P^{11}$ and $P^{12}$ each independently represent a hydrogen atom or a hydroxyl-protecting group, and $P^{13}$ represents a hydrogen atom or an amino-protecting group; or (c) reacting a compound of formula 11:

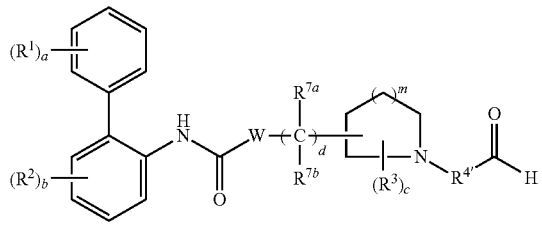

11 or a hydrate thereof; wherein $R^{4'}$ represents a residue that, together with the carbon to which it is attached, affords a group $R^4$ upon completion of the reaction; with a compound of formula 10 in the presence of a reducing agent; and then removing any protecting group $P^8$, $P^9$, $P^{10}$, $P^{11}$, $P^{12}$ or $P^{13}$ to provide a compound of formula I.

2. The process of claim 1, wherein the process further comprises forming a pharmaceutically acceptable salt of the compound of formula I.

3. The process of claim 1, wherein W represents O.

4. The process of claim 1, wherein a, b, and c are each 0, and $R^5$ is hydrogen.

5. The process of claim 1, wherein d is 0.

6. The process of claim 1, wherein d is 1; and $R^{7a}$ and $R^{7b}$ are both hydrogen.

7. The process of claim 1, wherein m is 2.

8. The process of claim 1, wherein $R^6$ is hydrogen.

9. The process of claim 1, wherein $R^6$ is hydroxy.

10. The process of claim 1, wherein $R^4$ is a divalent group of the formula:

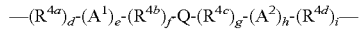

wherein d, e, f, g, h and i are each independently selected from 0 and 1;

$R^{4a}$, $R^{4b}$, $R^{4c}$ and $R^{4d}$ are each independently selected from (1-10C)alkylene, (2-10C)alkenylene and (2-10C)alkynylene, wherein each alkylene, alkenylene or alkynylene group is unsubstituted or substituted with from 1 to 5 substituents independently selected from (1-4C)alkyl, fluoro, hydroxy, phenyl and phenyl-(1-4C) alkyl;

$A^1$ and $A^2$ are each independently selected from (3-7C)cycloalkylene, (6-10C)arylene, —O-(6-10C)arylene, (6-10C)arylene-O—, (2-9C)heteroarylene, —O-(2-9C)heteroarylene, (2-9C)heteroarylene-O— and (3-6C)heterocyclene, wherein each cycloalkylene is unsubstituted or substituted with from 1 to 4 substituents selected independently from (1-4C)alkyl, and each arylene, heteroarylene or heterocyclene group is unsubstituted or substituted with from 1 to 4 substituents independently selected from halo, (1-4C)alkyl, (1-4C)alkoxy, —S-(1-4C)alkyl, —S(O)$_2$-(1-4C)alkyl, —C(O)O(1-4C)alkyl, carboxy, cyano, hydroxy, nitro, trifluoromethyl and trifluoromethoxy;

Q is selected from a bond, —O—, —C(O)O—, —OC(O)—, —S—, —S(O)—, —S(O)$_2$—, —N($Q^a$)C(O)—, —C(O)N($Q^b$)-, —N($Q^c$)S(O)$_2$—, —S(O)$_2$N($Q^d$)-, —N($Q^e$)C(O)N($Q^f$)-, —N($Q^g$)S(O)$_2$N($Q^h$)-, —OC(O)N($Q^i$)-, —N($Q^j$)C(O)O— and —N($Q^k$);

$Q^a$, $Q^b$, $Q^c$, $Q^d$, $Q^e$, $Q^f$, $Q^g$, $Q^h$, $Q^i$, $Q^j$ and $Q^k$ are each independently selected from hydrogen, (1-6C)alkyl, $A^3$ and (1-4C)alkylene-$A^4$, wherein the alkyl group is unsubstituted or substituted with from 1 to 3 substituents independently selected from fluoro, hydroxy and (1-4C)alkoxy; or together with the nitrogen atom and the group $R^{4b}$ or $R^{4c}$ to which they are attached, form a 4-6 membered azacycloalkylene group;

$A^3$ and $A^4$ are each independently selected from (3-6C)cycloalkyl, (6-10C)aryl, (2-9C)heteroaryl and (3-6C)heterocyclyl, wherein each cycloalkyl is unsubstituted or substituted with from 1 to 4 substituents selected independently from (1-4C)alkyl and each aryl, heteroaryl or heterocyclyl group is unsubstituted or substituted with from 1 to 4 substituents independently selected from halo, (1-4C)alkyl and (1-4C)alkoxy.

11. The process of claim 10, wherein $R^4$ is a divalent group of the formula: —($R^{4a}$)$_d$— where $R^{4a}$ is (4-10C)alkylene.

12. The process of claim 10, wherein $R^4$ is —(CH$_2$)$_4$—, —(CH$_2$)$_5$—, —(CH$_2$)$_6$—, —(CH$_2$)$_7$—, —(CH$_2$)$_8$—, —(CH$_2$)$_9$, or —(CH$_2$)$_{10}$—.

13. The process of claim 10, wherein $R^4$ is a divalent group of the formula:

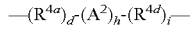

where $R^{4a}$ is (1-10C)alkylene; $A^2$ is (6-10C)arylene or (2-9C)heteroarylene; and $R^{4d}$ is (1-10C)alkylene.

14. The process of claim 10, wherein $R^4$ is a divalent group of the formula:

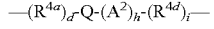

where Q is —O— or —N($Q^k$)-; $Q^k$ is hydrogen or (1-3C)alkyl; $R^{4a}$ is (1-10C)alkylene; $A^2$ is (6-10C)arylene or (2-9C)heteroarylene; and $R^{4d}$ is (1-10C)alkylene.

15. The process of claim 10, wherein Q is —N($Q^a$)C(O)13 or —C(O)N($Q^b$)-.

* * * * *

UNITED STATES PATENT AND TRADEMARK OFFICE
CERTIFICATE OF CORRECTION

| | |
|---|---|
| PATENT NO. | : 8,247,564 B2 |
| APPLICATION NO. | : 12/903365 |
| DATED | : August 21, 2012 |
| INVENTOR(S) | : Mathai Mammen et al. |

It is certified that error appears in the above-identified patent and that said Letters Patent is hereby corrected as shown below:

At Column 97, line 24, insert "-S(O)-(1-4C)alkyl," before "-S(O)$_2$-(1-4C)alkyl,".

At Column 98, line 30, delete "13" after "-N(Q$^a$)C(O)".

Signed and Sealed this
First Day of January, 2013

David J. Kappos
*Director of the United States Patent and Trademark Office*